US012559571B2

(12) United States Patent (10) Patent No.: US 12,559,571 B2
Matsuda et al. (45) Date of Patent: Feb. 24, 2026

(54) ANTIBODIES AND COMPOSITIONS FOR USE IN DETECTING OR CAPTURING A POLYPEPTIDE IN A SAMPLE, AND METHODS FOR DETECTING OR CAPTURING A POLYPEPTIDE IN A SAMPLE

(71) Applicant: Chugai Seiyaku Kabushiki Kaisha, Tokyo (JP)

(72) Inventors: Eriko Matsuda, Kanagawa (JP); Mitsuko Shibuya, Shizuoka (JP); Masanobu Nishidate, Kanagawa (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 1026 days.

(21) Appl. No.: 17/603,684

(22) PCT Filed: Apr. 17, 2020

(86) PCT No.: PCT/JP2020/016813
§ 371 (c)(1),
(2) Date: Oct. 14, 2021

(87) PCT Pub. No.: WO2020/213706
PCT Pub. Date: Oct. 22, 2020

(65) Prior Publication Data
US 2022/0195070 A1 Jun. 23, 2022

(30) Foreign Application Priority Data
Apr. 19, 2019 (JP) ................................. 2019-079740

(51) Int. Cl.
*C07K 16/42* (2006.01)
*C07H 21/00* (2006.01)
*C07K 16/00* (2006.01)

(52) U.S. Cl.
CPC .......... *C07K 16/4283* (2013.01); *C07H 21/00* (2013.01); *C07K 16/00* (2013.01); *C07K 2317/30* (2013.01); *C07K 2317/56* (2013.01); *C07K 2317/92* (2013.01)

(58) Field of Classification Search
CPC ............ C07K 16/4283; C07K 2317/30; C07K 2317/56; C07K 2317/92
See application file for complete search history.

(56) References Cited

U.S. PATENT DOCUMENTS

2015/0210763 A1* 7/2015 Kuramochi ............. A61P 37/08
435/69.6

FOREIGN PATENT DOCUMENTS

| TW | 201925233 A | 7/2019 |
| WO | WO2016098356 A1 | 6/2016 |
| WO | WO2016125495 A1 | 8/2016 |

| WO | WO2017046994 A1 | 3/2017 |
| WO | WO-2017072210 A1 * | 5/2017 | ............ C07K 16/00 |
| WO | WO2018025982 A1 | 2/2018 |
| WO | WO2019112027 A1 | 6/2019 |

OTHER PUBLICATIONS

Li CH, et al. beta-Endorphin omission analogs: dissociation of immunoreactivity from other biological activities. Proc Natl Acad Sci U S A. Jun. 1980;77(6):3211-4. doi: 10.1073/pnas.77.6.3211. PMID: 6251449; PMCID: PMC349584. (Year: 1980).*
Lederman, et al. A single amino acid substitution in a common African allele of the CD4 molecule ablates binding of the monoclonal antibody, OKT4. Mol Immunol. Nov. 1991;28(11):1171-81. doi: 10.1016/0161-5890(91)90003-3. PMID: 1961196. (Year: 1991).*
Abaza MS, et al. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-44. (Year: 1992).*
Colman PM. Effects of amino acid sequence changes on antibody-antigen interactions. Res Immunol. Jan. 1994;145(1):33-6. doi: 10.1016/s0923-2494(94)80039-1. PMID: 7516563. (Year: 1994).*
Bendayan M. Possibilities of false immunocytochemical results generated by the use of monoclonal antibodies: the example of the anti-proinsulin antibody. J Histochem Cytochem. Sep. 1995;43(9):881-6. doi: 10.1177/43.9.7642961. PMID: 7642961. (Year: 1995).*
Van Regenmortel. Mapping Epitope Structure and Activity: From One-Dimensional Prediction to Four-Dimensional Description of Antigenic Specificity. Methods. Jun. 1996;9(3):465-72. doi: 10.1006/meth.1996.0054. PMID: 8812702. (Year: 1996).*
Maeda, A., et al., "Identification of human IgG1 variant with enhanced FcRn binding and without increased binding to rheumatoid factor autoantibody," mAbs, 9(5):844-853 (2017).
Vidarsson, G., et al., "IgG subclasses and allotypes: from structure to effector functions," Front Immunol., 5:520 (2014).
Köhler, G. and Milstein, C., "Continuous cultures of fused cells secreting antibody of predefined specificity," Nature, 256:495-497 (1975).
Lagassé, H. A., et al., "Recent advances in (therapeutic protein) drug development," F1000Research, 6(F1000 Faculty Rev):113 (2017).
Mimoto, F., et al., "Fc Engineering to Improve the Function of Therapeutic Antibodies," Curr Pharm Biotechnol., 17:1298-1314 (2016).

(Continued)

*Primary Examiner* — Maher M Haddad
*Assistant Examiner* — Alec Jon Peters
(74) *Attorney, Agent, or Firm* — Nixon & Vanderhye P.C.

(57) ABSTRACT

Provided herein is an antibody to detect and/or capture a polypeptide comprising a modified IgG heavy chain constant region that is derived from any one of constant regions in human naturally occurring IgGs or that is derived from a chimeric constant region obtained from at least two selected from the constant regions in human naturally occurring IgGs, a composition comprising the antibody for use in detecting or capturing a polypeptide in a sample, and a method for detecting or capturing a polypeptide in a sample using the antibody.

9 Claims, 8 Drawing Sheets

Specification includes a Sequence Listing.

(56)        References Cited

OTHER PUBLICATIONS

Reichert, J. M., "Monoclonal Antibodies as Innovative Therapeutics," Curr Pharm Biotechnol., 9:423-430 (2008).

Yu, X.-Q., et al., "Safety, Tolerability, and Pharmacokinetics of MEDI4893, an Investigational, Extended-Half-Life, Anti-*Staphylococcus aureus* Alpha-Toxin Human Monoclonal Antibody, in Healthy Adults," Antimicrob Agents Chemother., 61(1):e01020-16 (2017).

U.S. Appl. No. 14/377,556, 371(c) Date Aug. 8, 2014, Kuramochi et al.

GenBank, "*Homo sapiens* immunoglobulin gamma-1 heavy chain constant region (IGHG1) gene, partial cds," Accession No. J00228. 1, Dec. 2, 1998.

GenBank, "Human Ig germline H-chain G-E-A region B: gamma-4 constant region, 3' end," Accession No. K01316.1, Jul. 26, 2016.

* cited by examiner

Fig. 1

```
SG115            1 ASTKGPSVFPLAPSSKSTSGGTAALGCLVKDYFPEPVTVSWNSGALTSGVHTFPAVLQSS 60
SG115v1          1 ............................................................ 60
SG115v2          1 ............................................................ 60
G1m              1 ............................................................ 60
IGHG1_01(J00228) 1 ............................................................ 60
G4d              1 ...........C.R...ES......................................... 60
IGHG4_01(K01316) 1 ...........C.R...ES......................................... 60

SG115           61 GLYSLSSVVTVPSSSLGTQTYICNVNHKPSNTKVDKKVEPKSCDKTHTCPPCPAPELLRG 120
SG115v1         61 ............................................................ 120
SG115v2         61 .........................................................LG. 120
G1m             61 .........................................................LG. 120
IGHG1_01(J00228) 61 .........................................................LG. 120
G4d             61 ..................K..T...D...........R..S.---YGPP........FLG. 117
IGHG4_01(K01316) 61 ..................K..T...D...........R..S.---YGPP..S.....FLG. 117

SG115          121 PKVFLFPPKPKDTLMISRTPEVTCVVVDVSHEDPEVKFNWYVDGVEVHNAKTKPREEQYN 180
SG115v1        121 ............................................................ 180
SG115v2        121 .S.......................................................... 180
G1m            121 .S.......................................................... 180
IGHG1_01(J00228) 121 .S.......................................................... 180
G4d            118 .S.................................Q.....Q...............F. 177
IGHG4_01(K01316) 118 .S.................................Q.....Q...............F. 177

SG115          181 STYRVVSVLTVLHQDWLNGKEYKCKVSNKGLPSSIEKTISKAKGQPREPQVYTLPPSREE 240
SG115v1        181 ............................................................ 240
SG115v2        181 ............................................................ 240
G1m            181 ...............................A..AP........................ 240
IGHG1_01(J00228) 181 ...............................A..AP.......................D. 240
G4d            178 .........................................................Q.. 237
IGHG4_01(K01316) 178 .........................................................Q.. 237

SG115          241 MTKNQVSLTCLVKGFYPSDIAVEWESNGQPENNYKTTPPVLDSDGSFFLYSKLTVDKSRW 300
SG115v1        241 ............................................................ 300
SG115v2        241 ............................................................ 300
G1m            241 ............................................................ 300
IGHG1_01(J00228) 241 L........................................................... 300
G4d            238 ........................................................R... 297
IGHG4_01(K01316) 238 ........................................................R... 297

SG115          301 QQGNVFSCSVLHEALHAHYTRKELSLSP--  (SEQ ID NO: 1)      328
SG115v1        301 ..........M.....N...Q.S.....--  (SEQ ID NO: 2)      328
SG115v2        301 ......................---      (SEQ ID NO: 3)      328
G1m            301 ..........M.....N...Q.S.....--  (SEQ ID NO: 4)      328
IGHG1_01(J00228) 301 ..........M.....N...Q.S.....GK  (SEQ ID NO: 119)    330
G4d            298 .E........M.....N...Q.S....L--  (SEQ ID NO: 5)      325
IGHG4_01(K01316) 298 .E........M.....N...Q.S....LGK  (SEQ ID NO: 120)    327
```

A scheme of Fc-Mutated Antibody detection assay

A

B

A scheme of antigen detection assay

A
POD substrate
Anti-mouse-POD
Mouse Anti Fc-Mutation Antibody
Anti-hC5 Antibody
hC5     hC5
Rabbit anti-hC5 antibody B
POD substrate
Anti-rabbit-HRP
Rabbit Anti Fc-Mutation Antibody
Anti-IL-8 Antibody
IL-8     IL-8
Mouse anti-IL-8 antibody
Biotin
Streptavidin A scheme of IL-8 Simoa® assay (a)

(b)

1

ANTIBODIES AND COMPOSITIONS FOR USE IN DETECTING OR CAPTURING A POLYPEPTIDE IN A SAMPLE, AND METHODS FOR DETECTING OR CAPTURING A POLYPEPTIDE IN A SAMPLE

CROSS-REFERENCE TO RELATED APPLICATIONS

This application is a U.S. National Phase of PCT Application No. PCT/JP2020/016813, filed Apr. 17, 2020, which claims the benefit of Japanese Patent Application No. 2019-079740, filed Apr. 19, 2019, each of which is incorporated herein by reference in its entirety.

REFERENCE TO SEQUENCE LISTING SUBMITTED ELECTRONICALLY

The content of the electronically submitted sequence listing (Name: 6663_0182 Sequence_Listing.txt; Size: 91,308 bytes; and Date of Creation: Aug. 12, 2025) is incorporated herein by reference in its entirety.

TECHNICAL FIELD

The present invention relates to antibodies and compositions for use in detecting or capturing a polypeptide in a sample, and methods for detecting or capturing a polypeptide in a sample.

BACKGROUND ART

Hybridoma technology has enabled the production of monoclonal antibodies and this monoclonal antibody technology has been widely used in many scientific fields (NPL1). After this technological achievement, further efforts were made in the field of therapeutic and diagnostic antibodies. 30 years have passed since the first US approval of monoclonal antibody therapy (NPL2). More than 30 antibodies have been approved by the FDA and a significant number of candidates are under clinical and pre-clinical evaluation. So far, monoclonal antibodies have remained the standard therapeutic molecules and are used in various disease areas such as cancer, autoimmune diseases, respiratory diseases, infectious diseases, and neural diseases (NPL3).

In order to increase the merit of therapeutic antibodies, many different types of engineered Fc modifications to improve functions such as those for antibody-dependent cell-mediated cytotoxicity enhancement, complement dependent cytotoxicity enhancement, antibody half-life extension, antigen clearance modulation, and facilitation of heavy chain heterodimerization, were identified (NPL4).

Antibodies that specifically bind to engineered Fc regions but not to a wild-type Fc have been reported (NPL5, PTL1). It was proven that antibodies against engineered Fc regions are quite useful for various purposes.

CITATION LIST

Patent Literature

[PTL1] WO2017072210A1

2

Non Patent Literature

[NPL1] Kohler, G. et al., Nature 256:495-497 (1975)
[NPL2] Reichert, J. M. et al., Curr. Pharm. Biotechnol. 9:423-430 (2008)
[NPL3] Lagasse HAD et al. F1000Research 2017, 6 (F1000 Faculty Rev): 113
[NPL4] Mimoto et al., Curr. Pharm. Biotechnol. 17:1298-1314 (2016)
[NPL5] Yu et al., Antimicrob Agents Chemother. 61 (2016)

SUMMARY OF INVENTION

We have provided some antibodies comprising a modified IgG heavy chain constant region that is derived from any one of constant regions in human naturally occurring IgGs or that is derived from a chimeric constant region obtained from at least two selected from the constant regions in human naturally occurring IgGs. The antibodies include, for example, satralizumab, nemolizumab, emicizumab, SKY59 (Crovalimab), AMY109, and GYM329. For example, the modified IgG heavy chain constant region in one of them comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438 and Glu at position 440 (all positions according to the EU numbering system). The present invention provides antibodies that specifically bind to, detect, and/or capture a polypeptide comprising the modified IgG heavy chain constant region or an epitope in it, compositions comprising the antibody, and methods of using the antibody. Specifically, the present invention relates to [1] to below.

[1] An isolated antibody which specifically binds to a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

[2] The antibody of [1], wherein the antibody substantially does not bind to said any one of constant regions in human naturally occurring IgGs and the chimeric constant region obtained from at least two selected from the constant regions in human naturally occurring IgGs.

[3] The antibody of [1] or [2], wherein the constant regions in human naturally occurring IgGs are an IgG1 constant region consisting of the amino acid sequence of SEQ ID NO: 106, an IgG2 constant region consisting of the amino acid sequence of SEQ ID NO: 107, an IgG3 constant region consisting of the amino acid sequence of SEQ ID NO: 108, and an IgG4 constant region consisting of the amino acid sequence of SEQ ID NO: 109.

[4] The antibody of any one of [1] to [3], wherein said modified heavy chain constant region is derived from a chimeric constant region obtained from constant regions in human naturally occurring IgG1 and IgG4.

[5] The antibody of any one of [1] to [4], wherein the modified IgG heavy chain constant region comprises at least one amino acid selected from the group consisting of Arg at position 235, Arg at position 236, Lys at position 239, Leu at position 428, Ala at position 434, Arg at position 438, and Glu at position 440 (all positions according to the EU numbering system).

[6] The antibody of any one of [1] to [5], wherein the modified IgG heavy chain constant region comprises at least one amino acid selected from the group consisting of Arg at position 235, Arg at position 236, and Lys at position 239 (all positions according to the EU numbering system).

[7] The antibody of any one of [1] to [6], wherein the modified IgG heavy chain constant region comprises Arg at position 235, and either or both of Arg at position 236 and Lys at position 239 (all positions according to the EU numbering system).

[8] The antibody of any one of [1] to [7], which binds to the part consisting of the amino acid sequence RRGPK (SEQ ID NO: 104) or RRGPS (SEQ ID NO: 117) in the modified IgG heavy chain constant region.

[9] The antibody of any one of [1] to [8], which comprises any one of following (a) to (f):

(a) variable regions that comprise
HVR-H1 comprising the amino acid sequence of SEQ ID NO: 33,
HVR-H2 comprising the amino acid sequence of SEQ ID NO: 45,
HVR-H3 comprising the amino acid sequence of SEQ ID NO: 57,
HVR-L1 comprising the amino acid sequence of SEQ ID NO: 69,
HVR-L2 comprising the amino acid sequence of SEQ ID NO: 81, and
HVR-L3 comprising the amino acid sequence of SEQ ID NO: 93;

(b) variable regions that comprise
HVR-H1 comprising the amino acid sequence of SEQ ID NO: 34,
HVR-H2 comprising the amino acid sequence of SEQ ID NO: 46,
HVR-H3 comprising the amino acid sequence of SEQ ID NO: 58,
HVR-L1 comprising the amino acid sequence of SEQ ID NO: 70,
HVR-L2 comprising the amino acid sequence of SEQ ID NO: 82, and
HVR-L3 comprising the amino acid sequence of SEQ ID NO: 94;

(c) variable regions that comprise
HVR-H1 comprising the amino acid sequence of SEQ ID NO: 37,
HVR-H2 comprising the amino acid sequence of SEQ ID NO: 49,
HVR-H3 comprising the amino acid sequence of SEQ ID NO: 61,
HVR-L1 comprising the amino acid sequence of SEQ ID NO: 73,
HVR-L2 comprising the amino acid sequence of SEQ ID NO: 85, and
HVR-L3 comprising the amino acid sequence of SEQ ID NO: 97;

(d) variable regions that comprise
HVR-H1 comprising the amino acid sequence of SEQ ID NO: 38,
HVR-H2 comprising the amino acid sequence of SEQ ID NO: 50,
HVR-H3 comprising the amino acid sequence of SEQ ID NO: 62, HVR-L1 comprising the amino acid sequence of SEQ ID NO: 74,
HVR-L2 comprising the amino acid sequence of SEQ ID NO: 86, and
HVR-L3 comprising the amino acid sequence of SEQ ID NO: 98;

(e) variable regions that comprise
HVR-H1 comprising the amino acid sequence of SEQ ID NO: 39,
HVR-H2 comprising the amino acid sequence of SEQ ID NO: 51,
HVR-H3 comprising the amino acid sequence of SEQ ID NO: 63,
HVR-L1 comprising the amino acid sequence of SEQ ID NO: 75,
HVR-L2 comprising the amino acid sequence of SEQ ID NO: 87, and
HVR-L3 comprising the amino acid sequence of SEQ ID NO: 99; and (f) variable regions that comprise
HVR-H1 comprising the amino acid sequence of SEQ ID NO: 41,
HVR-H2 comprising the amino acid sequence of SEQ ID NO: 53,
HVR-H3 comprising the amino acid sequence of SEQ ID NO: 65,
HVR-L1 comprising the amino acid sequence of SEQ ID NO: 77,
HVR-L2 comprising the amino acid sequence of SEQ ID NO: 89, and
HVR-L3 comprising the amino acid sequence of SEQ ID NO: 101.

[10] The antibody of any one of [1] to [5], wherein the modified IgG heavy chain constant region comprises at least one selected from the group consisting of Leu at position 428, Ala at position 434, Arg at position 438, and Glu at position 440 (all positions according to the EU numbering system).

[11] The antibody of any one of [1] to [5] and [10], wherein the modified IgG heavy chain constant region comprises Leu at position 428, Ala at position 434, Arg at position 438, and Glu at position 440, and optionally threonine at position 436 (all positions according to the EU numbering system).

[12] The antibody of any one of [1] to [5], [10], and [11], which binds to the part consisting of the amino acid sequence LHEALHAHYTRKE (SEQ ID NO: 105) or LHEALHAHTTRKE (SEQ ID NO: 118) in the modified IgG heavy chain constant region.

[13] The antibody of any one of [1] to [5] and to [12], which comprises any one of following (g) to (1):

(g) variable regions that comprise
HVR-H1 comprising the amino acid sequence of SEQ ID NO: 32,
HVR-H2 comprising the amino acid sequence of SEQ ID NO: 44,
HVR-H3 comprising the amino acid sequence of SEQ ID NO: 56,
HVR-L1 comprising the amino acid sequence of SEQ ID NO: 68,
HVR-L2 comprising the amino acid sequence of SEQ ID NO: 80, and
HVR-L3 comprising the amino acid sequence of SEQ ID NO: 92;

(h) variable regions that comprise
HVR-H1 comprising the amino acid sequence of SEQ ID NO: 35, HVR-H2 comprising the amino acid sequence of SEQ ID NO: 47, HVR-H3 comprising the amino acid sequence of SEQ ID NO: 59, HVR-L1 comprising the amino acid sequence of SEQ ID NO: 71, HVR-L2 comprising the amino acid sequence of SEQ ID NO: 83, and HVR-L3 comprising the amino acid sequence of SEQ ID NO: 95;

(i) variable regions that comprise

HVR-H1 comprising the amino acid sequence of SEQ ID NO: 36,

HVR-H2 comprising the amino acid sequence of SEQ ID NO: 48,

HVR-H3 comprising the amino acid sequence of SEQ ID NO: 60,

HVR-L1 comprising the amino acid sequence of SEQ ID NO: 72,

HVR-L2 comprising the amino acid sequence of SEQ ID NO: 84, and

HVR-L3 comprising the amino acid sequence of SEQ ID NO: 96;

(j) variable regions that comprise

HVR-H1 comprising the amino acid sequence of SEQ ID NO: 40,

HVR-H2 comprising the amino acid sequence of SEQ ID NO: 52,

HVR-H3 comprising the amino acid sequence of SEQ ID NO: 64,

HVR-L1 comprising the amino acid sequence of SEQ ID NO: 76,

HVR-L2 comprising the amino acid sequence of SEQ ID NO: 88, and

HVR-L3 comprising the amino acid sequence of SEQ ID NO: 100;

(k) variable regions that comprise

HVR-H1 comprising the amino acid sequence of SEQ ID NO: 42,

HVR-H2 comprising the amino acid sequence of SEQ ID NO: 54,

HVR-H3 comprising the amino acid sequence of SEQ ID NO: 66,

HVR-L1 comprising the amino acid sequence of SEQ ID NO: 78,

HVR-L2 comprising the amino acid sequence of SEQ ID NO: 90, and

HVR-L3 comprising the amino acid sequence of SEQ ID NO: 102; and (l) variable regions that comprise HVR-H1 comprising the amino acid sequence of SEQ ID NO: 43, HVR-H2 comprising the amino acid sequence of SEQ ID NO: 55, HVR-H3 comprising the amino acid sequence of SEQ ID NO: 67, HVR-L1 comprising the amino acid sequence of SEQ ID NO: 79, HVR-L2 comprising the amino acid sequence of SEQ ID NO: 91, and HVR-L3 comprising the amino acid sequence of SEQ ID NO: 103.

[14] An isolated antibody which binds to the same epitope as the antibody of any one of [1] to [13].

[15] An isolated antibody which specifically binds to a modified IgG heavy chain constant region, wherein binding of the antibody to the modified IgG heavy chain constant region competes with the antibody of any one of [1] to [14], wherein the modified IgG heavy chain constant region is derived from any one of constant regions in human naturally occurring IgGs or is derived from a chimeric constant region obtained from at least two selected from the constant regions in human naturally occurring IgGs, and comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

[16] A composition for use in detecting or capturing a polypeptide in a sample, wherein the composition comprises the antibody of any one of [1] to [15].

[17] The composition of [16], wherein the polypeptide comprises a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

[18] The composition of [16], wherein the polypeptide comprises any one of the amino acid sequence consisting of RRGPK (SEQ ID NO: 104), the amino acid sequence consisting of RRGPS (SEQ ID NO: 117), the amino acid sequence consisting of LHEAL-HAHYTRKE (SEQ ID NO: 105), and the amino acid sequence consisting of LHEALHAHTTRKE (SEQ ID NO: 118).

[19] The composition of [18], wherein the polypeptide comprises a modified IgG heavy chain constant region that comprises any one of the amino acid sequence consisting of RRGPK (SEQ ID NO: 104), the amino acid sequence consisting of RRGPS (SEQ ID NO: 117), the amino acid sequence consisting of LHEAL-HAHYTRKE (SEQ ID NO: 105), and the amino acid sequence consisting of LHEALHAHTTRKE (SEQ ID NO: 118).

[20] A method for detecting or capturing a polypeptide in a sample, wherein the method comprises contacting the sample with the antibody of any one of [1] to or with the composition of any one of to [19].

[21] The method of [20], wherein the polypeptide comprises a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

[22] The method of [20], wherein the polypeptide comprises any one of the amino acid sequence consisting of RRGPK (SEQ ID NO: 104), the amino acid sequence consisting of RRGPS (SEQ ID NO: 117), the amino acid sequence consisting of LHEALHAHYTRKE (SEQ ID NO: 105), and the amino acid sequence consisting of LHEALHAHTTRKE (SEQ ID NO: 118).

[23] The method of [22], wherein the polypeptide comprises a modified IgG heavy chain constant region that comprises any one of the amino acid sequence consisting of RRGPK (SEQ ID NO: 104), the amino acid sequence consisting of RRGPS (SEQ ID NO: 117), the amino acid sequence consisting of LHEAL-HAHYTRKE (SEQ ID NO: 105), and the amino acid sequence consisting of LHEALHAHTTRKE (SEQ ID NO: 118).

[24] A method for measuring concentration of a first antibody in a sample, wherein the first antibody can bind to a first epitope of an antigen, wherein the sample comprises the first antibody and the antigen, and wherein the method comprises (A) contacting the sample with a plate or beads on which a second antibody is immobilized, (B) contacting a solution that comprises the antigen and does not comprise the first antibody and the second antibody with the plate or the beads after (A), and (C) detecting the antigen that is captured on the plate or the beads via the second antibody and the first antibody by using a third antibody after (B), wherein the first antibody comprises a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system), the second antibody is the antibody of any one of [1] to [15], and the third antibody can bind to a second epitope of the antigen which is different from the first epitope and has an IgG heavy chain constant region whose amino acid sequence is different from those of the first antibody and the second antibody.

[25] A method for measuring concentration of an antigen in a sample, wherein the sample comprises the antigen and a first antibody that can bind to a first epitope of the antigen, wherein the method comprises (D) contacting the sample with a plate or beads on which a third antibody is immobilized, (E) contacting a solution that comprises the first antibody and does not comprise the antigen and the third antibody with the plate or the beads after (D), and (F) detecting the first antibody that is captured on the plate or the beads via the third antibody and the antigen by using a second antibody, wherein the first antibody comprises a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system), the second antibody is the antibody of any one of [1] to and has an IgG heavy chain constant region whose amino acid sequence is different from those of the first antibody and the third antibody, and the third antibody can bind to a second epitope of the antigen which is different from the first epitope.

BRIEF DESCRIPTION OF DRAWINGS

FIG. 1 illustrates sequence alignment of 5 modified IgG heavy chain constant regions (SG115 (SEQ ID NO:1), SG115v1 (SEQ ID NO:2), SG115v2 (SEQ ID NO:3), G1m (SEQ ID NO:4), and G4d (SEQ ID NO:5) described in Example 2. Human IgG CH germline sequences, namely IGHG1_01 (J00228) (SEQ ID NO:119) and IGHG4_01 (K01316) (SEQ ID NO:120), are also aligned for comparison. A dot indicates the same amino acid as SG115 at the position.

FIG. 2-1 and FIG. 2-2 illustrate the binding of 12 Anti-SG115 Antibodies to 5 modified IgG heavy chain constant regions (SG115, SG115v1, SG115v2, G1m, and G4d) in ELISA. SKA0009, SKA0016, SKA0046, SKA0052, SKA0054, and SKA0127 showed selective binding to SG115v1, while SKA0001, SKA0027, SKA0028, SKA0117, SKA0141, and SKA0171 showed selective binding to SG115v2, as described in Example 2.

FIG. 2-2 is a continuation of FIG. 2-1.

DESCRIPTION OF EMBODIMENTS

I. Definition

Figures 1, 2:
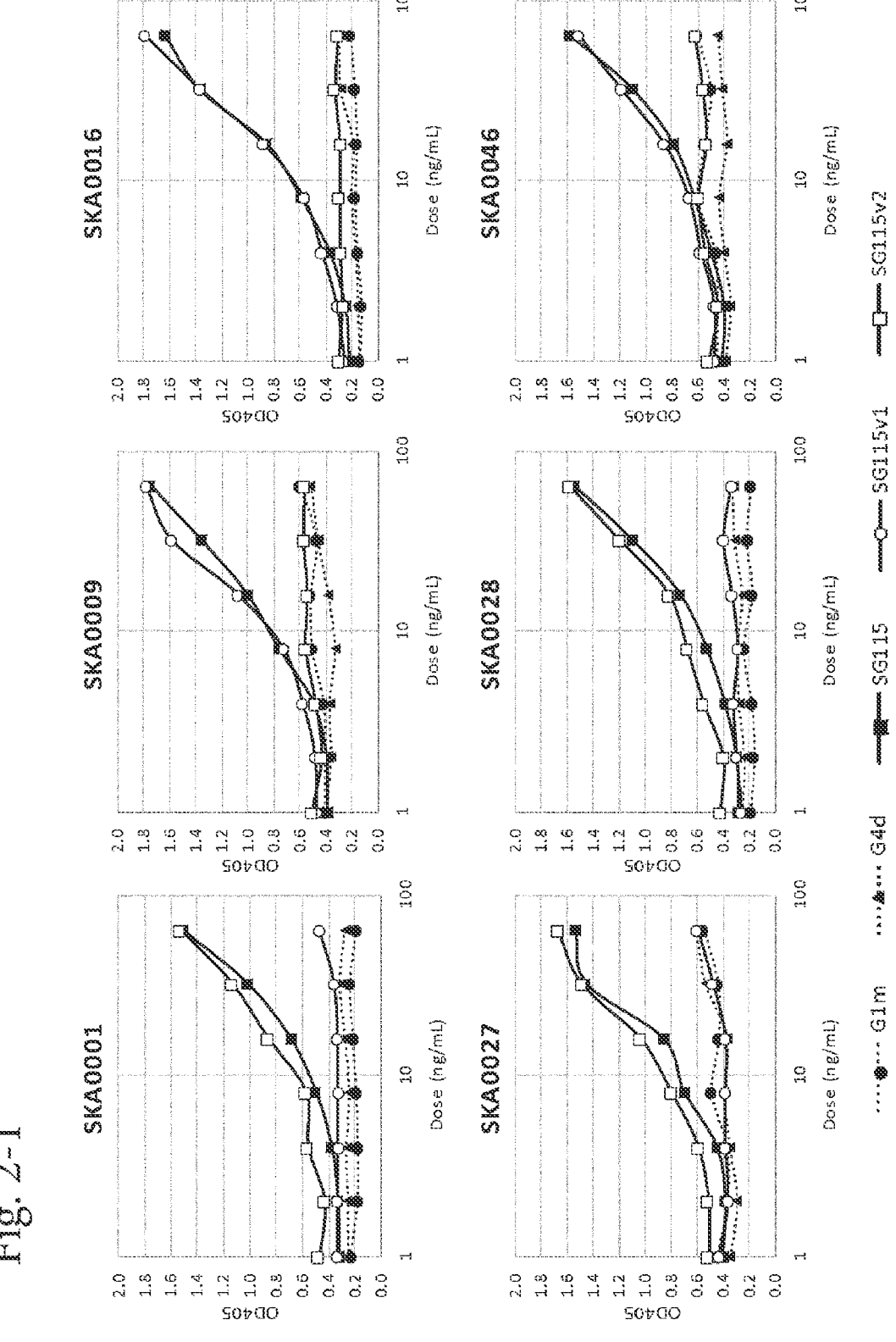
Figure 2:
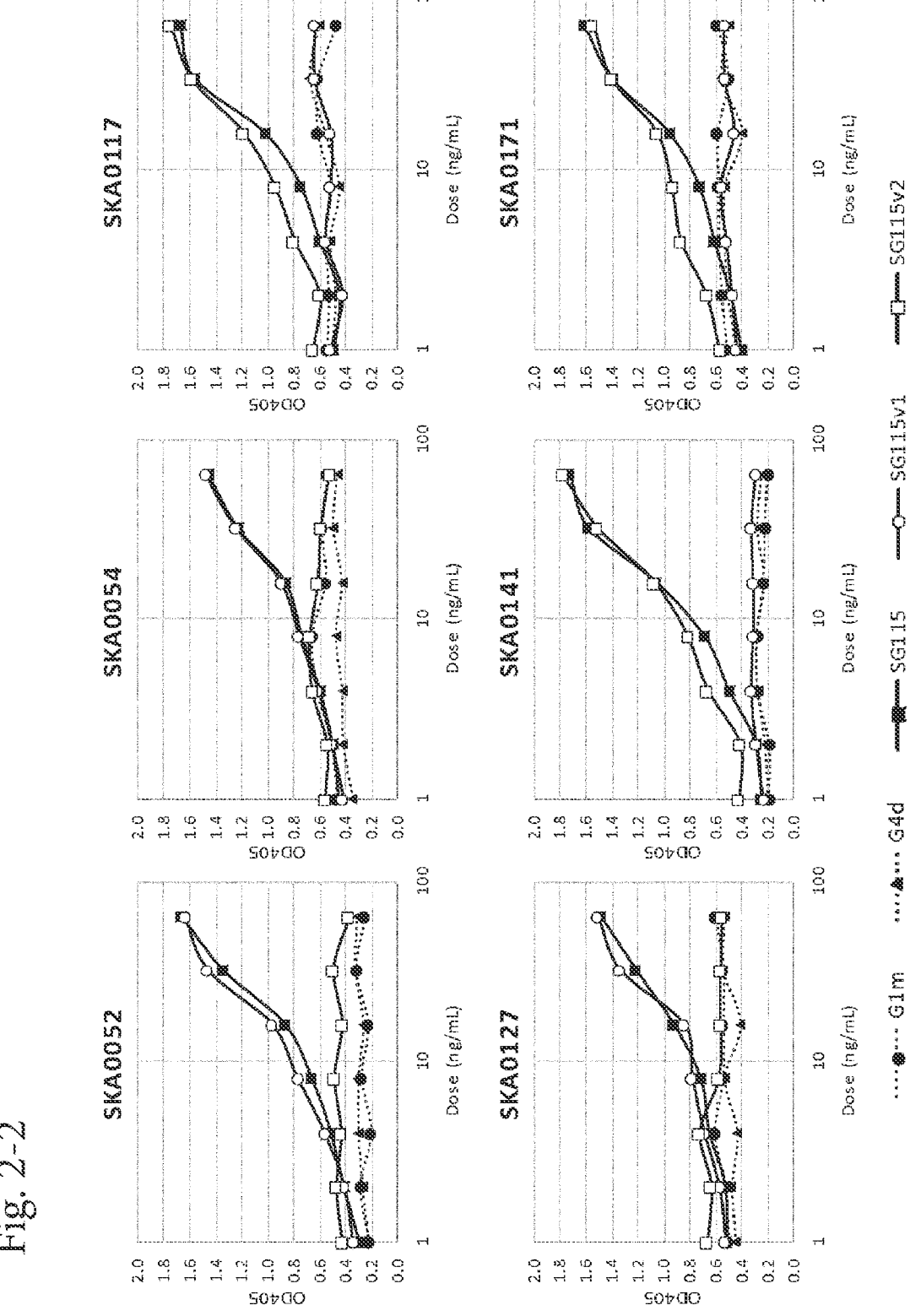

"Affinity" refers to the strength of the sum total of noncovalent interactions between a single binding site of a molecule (e.g., an antibody) and its binding partner (e.g., an antigen). Unless indicated otherwise, as used herein, "binding affinity" or "binding activity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "an isolated antibody which specifically binds to a modified IgG heavy chain constant region that is derived from any one of constant regions in human naturally occurring IgGs or that is derived from a chimeric constant region obtained from at least two selected from the constant regions in human naturally occurring IgGs" refers to an antibody that is capable of binding to a specific type of modified IgG heavy chain constant region with sufficient affinity such that the antibody is useful as a detection, capturing, or diagnostic agent in targeting the modified IgG heavy chain constant region. In one embodiment, for an antibody that specifically binds to the modified IgG heavy chain constant region, the extent of binding of the antibody to a non-modified human IgG heavy chain constant region is less than about 10% of the binding of the modified IgG heavy chain constant region as measured, e.g., by a radioimmunoassay (RIA). In certain embodiments, an antibody that binds to the modified IgG heavy chain constant region has a dissociation constant (Kd) of 1 micro M or less, 100 nM or less, 10 nM or less, 1 nM or less, 0.1 nM or less, 0.01 nM or less, or 0.001 nM or less (e.g., $10^{-8}$ M or less, e.g. from $10^{-8}$ M to $10^{-13}$ M, e.g., from $10^{-9}$ M to $10^{-13}$ M). In certain embodiments, an antibody that binds to the modified IgG heavy chain constant region binds to an epitope in the modified IgG heavy chain constant region.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called alpha, delta, epsilon, gamma, and mu, respectively.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "constant region" herein is a region in an antibody corresponding to any one of an IgG1 constant region consisting of the amino acid sequence of SEQ ID NO: 106, an IgG2 constant region consisting of the amino acid sequence of SEQ ID NO: 107, an IgG3 constant region consisting of the amino acid sequence of SEQ ID NO: 108, and an IgG4 constant region consisting of the amino acid sequence of SEQ ID NO: 109. The constant region consists of a CH1 region (positions 118 to 215 according to the EU numbering system), a hinge region (positions 216 to 230 according to the EU numbering system), a CH2 region (positions 231 to 340 according to the EU numbering system), and a CH3 region (positions 341 to 446 according to the EU numbering system).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W. H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2 (L2)-FR3-H3 (L3)-FR4.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, J. Mol. Biol. 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

II. Antibody

An antibody in the present invention is an isolated antibody which specifically binds to a modified IgG heavy chain constant region.

In one embodiment, the antibody substantially does not bind to constant regions in human naturally occurring IgGs and a chimeric constant region obtained from at least two selected from the constant regions in human naturally occurring IgGs. In this embodiment, a binding activity of the antibody to said constant regions in human naturally occurring IgGs and the chimeric IgG consisting of at least two IgGs selected from the human naturally occurring IgGs is below the detection limit in an enzyme-linked immunoassay. On the other hand, a binding activity of the antibody to the modified IgG heavy chain constant region is detectable in an enzyme-linked immunoassay.

In a further aspect of the invention, the antibody is a monoclonal antibody, including a chimeric, humanized or human antibody. In one embodiment, the antibody is an antibody fragment, e.g., a Fv, Fab, Fab', scFv, diabody, or F(ab')2 fragment. In another embodiment, the antibody is a full length antibody, e.g., an intact IgG1, IgG2, IgG3 and IgG4 antibodies, or other antibody class or isotype as defined herein.

A. Modified IgG Heavy Chain Constant Region

In one embodiment, the modified IgG heavy chain constant region is derived from any one of constant regions in human naturally occurring IgGs or is derived from a chimeric constant region obtained from at least two selected from the constant regions in human naturally occurring IgGs. The constant regions in human naturally occurring IgGs are an IgG1 constant region consisting of the amino acid sequence of SEQ ID NO: 106, an IgG2 constant region consisting of the amino acid sequence of SEQ ID NO: 107, an IgG3 constant region consisting of the amino acid sequence of SEQ ID NO: 108, and an IgG4 constant region consisting of the amino acid sequence of SEQ ID NO: 109.

In one embodiment, the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

In further embodiment, the modified IgG heavy chain constant region can be derived from a chimeric constant region obtained from constant regions in human naturally occurring IgG1 and IgG4. In preferred embodiment, the constant region is derived from a chimeric constant region obtained from constant regions in human naturally occurring IgG1 and IgG4.

In preferred embodiment, the modified IgG heavy chain constant region comprises at least one amino acid selected from the group consisting of Arg at position 235, Arg at position 236, Lys at position 239, Leu at position 428, Ala at position 434, Arg at position 438, and Glu at position 440 (all positions according to the EU numbering system).

In one embodiment, the modified IgG heavy chain constant region may form a dimer, such as a heavy chain constant region in a naturally occurring IgG, or may form a halfmer, such as a heavy chain constant region in the monomeric Fc reported in Ishino, T. et al., J. Biol. Chem. 288:16529-37 (2013).

In one embodiment, when the modified IgG heavy chain constant region is in a human modified IgG heavy chain, the human modified IgG heavy chain is selected from the group consisting of human modified IgG1, IgG2, IgG3, and IgG4 heavy chains, and their chimeric IgG heavy chain. In a preferred embodiment, the human IgG heavy chain is a human IgG1 heavy chain, human IgG4 heavy chain, or their chimeric IgG heavy chain.

B. Exemplary Antibodies that Specifically Recognize the Modifications Unique to a CH2 Region of the Modified IgG Heavy Chain Constant Region Arg at position 235, Arg at position 236, and Lys at position 239 (all positions according to the EU numbering system) are those which specifically exist in CH2 region of SG115 and SG115v1 used in the Examples. Thus, the modified IgG heavy chain constant region in exemplary antibodies here preferably comprises at least a region corresponding to a CH2 region of any one of constant regions in human naturally occurring IgGs or a chimeric constant region obtained from at least two selected from the constant regions in human naturally occurring IgGs.

In one embodiment, the modified IgG heavy chain constant region comprises at least one amino acid selected from the group consisting of Arg at position 235, Arg at position 236, and Lys at position 239 (all positions according to the EU numbering system). In this embodiment, the modified IgG heavy chain constant region comprises Arg at position 235, and either or both of Arg at position 236 and Lys at position 239 (all positions according to the EU numbering system).

In preferred embodiment, the modified IgG heavy chain constant region comprises all of these three mutations, or Arg at position 235 and Arg at position 236 (both positions according to the EU numbering system). In that case, the antibody binds to the part consisting of the amino acid sequence RRGPK (SEQ ID NO: 104) or RRGPS (SEQ ID NO: 117) in the modified IgG heavy chain constant region.

In one aspect where the antibody specifically binds to the modified IgG heavy chain constant region that comprises at least one amino acid selected from the group consisting of Arg at position 235, Arg at position 236, and Lys at position 239 (all positions according to the EU numbering system), the modified IgG heavy chain constant region that comprises Arg at position 235, and either or both of Arg at position 236 and Lys at position 239 (all positions according to the EU numbering system), or the part consisting of the amino acid sequence RRGPK (SEQ ID NO: 104) or RRGPS (SEQ ID NO: 117) in the modified IgG heavy chain constant region, the invention provides an antibody comprising at least one, two, three, four, five, or six HVRs selected from (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; (iii) HVR-H3 comprising the amino acid sequence of SEQ ID NO: 57, 58, 61, 62, 63 or 65; (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101.

In another aspect, the invention provides an antibody comprising at least one, at least two, or all three VH HVR sequences selected from (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; and (iii) HVR-H3 comprising the amino acid sequence of SEQ ID NO: 57, 58, 61, 62, 63 or 65. In one embodiment, the antibody comprises HVR-H3 comprising the amino acid sequence of SEQ ID NO: 57, 58, 61, 62, 63 or 65. In another embodiment, the antibody comprises HVR-H3 comprising the amino acid sequence of SEQ ID NO: 57, 58, 61, 62, 63 or 65 and HVR-L3 comprising the amino acid sequence of SEQ ID NO: 93, 94, 97, 98, 99 or 101. In a further embodiment, the antibody comprises HVR-H3 comprising the amino acid sequence of SEQ ID NO: 57, 58, 61, 62, 63 or 65, HVR-L3 comprising the amino acid sequence of SEQ ID NO: 93, 94, 97, 98, 99 or 101, and HVR-H2 comprising the amino acid sequence of SEQ ID NO: 45, 46, 49, 50, 51 or 53. In a further embodiment, the antibody comprises (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; and (iii) HVR-H3 comprising the amino acid sequence of SEQ ID NO: 57, 58, 61, 62, 63 or 65.

In another aspect, the invention provides an antibody comprising at least one, at least two, or all three VL HVR sequences selected from (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101. In one embodiment, the antibody comprises (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101.

In another aspect, an antibody of the invention comprises (I) a VH domain comprising at least one, at least two, or all three VH HVR sequences selected from (i) HVR-H1 comprising the amino acid sequence of SEQ ID NO: 33, 34, 37, 38, 39 or 41, (ii) HVR-H2 comprising the amino acid sequence of SEQ ID NO: 45, 46, 49, 50, 51 or 53, and (iii) HVR-H3 comprising the amino acid sequence of SEQ ID NO: 57, 58, 61, 62, 63 or 65; and (II) a VL domain comprising at least one, at least two, or all three VL HVR sequences selected from (iv) HVR-L1 comprising the amino acid sequence of SEQ ID NO: 69, 70, 73, 74, 75 or 77, (v) HVR-L2 comprising the amino acid sequence of SEQ ID NO: 81, 82, 85, 86, 87 or 89, and (vi) HVR-L3 comprising the amino acid sequence of SEQ ID NO: 93, 94, 97, 98, 99 or 101.

In another aspect, the invention provides an antibody comprising (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; (iii) HVR-H3 comprising the amino acid sequence of SEQ ID NO: 57, 58, 61, 62, 63 or 65; (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence selected from SEQ ID NO: 93, 94, 97, 98, 99 or 101.

In another aspect, an antibody described herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 9, 10, 13, 14, 15 or 17. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody described herein comprising that sequence retains the ability to bind to a first modified IgG heavy chain constant region.

In certain embodiments, a total of 1 to 10 amino acids have been substituted, inserted and/or deleted in SEQ ID NO: 9, 10, 13, 14, 15 or 17. In certain embodiments, substitutions, insertions, or deletions occur in regions outside the HVRs (i.e., in the FRs). Optionally, the antibody comprises the VH sequence in SEQ ID NO: 9, 10, 13, 14, 15 or 17, including post-translational modifications of that sequence. In a particular embodiment, the VH comprises one, two or three HVRs selected from: (i) HVR-H1 comprising the amino acid sequence of SEQ ID NO: 33, 34, 37, 38, 39 or 41, (ii) HVR-H2 comprising the amino acid sequence of SEQ ID NO: 45, 46, 49, 50, 51 or 53, and (iii) HVR-H3 comprising the amino acid sequence of SEQ ID NO: 57, 58, 61, 62, 63 or 65. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 21, 22, 25, 26, 27 or 29. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to a first modified IgG heavy chain constant region. In certain embodiments, a total of 1 to 10 amino acids have been substituted, inserted and/or deleted in SEQ ID NO: 21, 22, 25, 26, 27 or 29. In certain embodiments, the substitutions, insertions, or deletions occur in regions outside the HVRs (i.e., in the FRs). Optionally, the antibody comprises the VL sequence in SEQ ID NO: 21, 22, 25, 26, 27 or 29, including post-translational modifications of that sequence. In a particular embodiment, the VL comprises one, two or three HVRs selected from (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a VH as in any of the embodiments provided above, and a VL as in any of the embodiments provided above. In one embodiment, the antibody comprises the VH and VL sequences in SEQ ID NO: 9, 10, 13, 14, 15 or 17 and SEQ ID NO: 21, 22, 25, 26, 27 or 29, respectively, including post-translational modifications of those sequences. Post-translational modifications include but are not limited to a modification of glutamine or glutamate in N-terminal of heavy chain or light chain to pyroglutamic acid by pyroglutamylation.

In one aspect, an antibody is provided, wherein the antibody competes for binding to the first modified IgG heavy chain constant region with an antibody which comprises: (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; (iii) HVR-H3 comprising the amino acid sequence of SEQ ID NO: 57, 58, 61, 62, 63 or 65; (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101.

In one aspect, an antibody is provided, wherein the antibody binds to the same epitope as an antibody which comprises: (i) HVR-H1 comprising the amino acid sequence of SEQ ID NO: 33, 34, 37, 38, 39 or 41; (ii) HVR-H2 comprising the amino acid sequence of SEQ ID NO: 45, 46, 49, 50, 51 or 53; (iii) HVR-H3 comprising the amino acid sequence of SEQ ID NO: 57, 58, 61, 62, 63 or 65; (iv) HVR-L1 comprising the amino acid sequence of SEQ ID NO: 69, 70, 73, 74, 75 or 77; (v) HVR-L2 comprising the amino acid sequence of SEQ ID NO: 81, 82, 85, 86, 87 or 89; and (vi) HVR-L3 comprising the amino acid sequence of SEQ ID NO: 93, 94, 97, 98, 99 or 101.

In specific embodiments where the antibody specifically binds to the modified IgG heavy chain constant region that comprises at least one amino acid selected from the group consisting of Arg at position 235, Arg at position 236, and Lys at position 239 (all positions according to the EU numbering system), the modified IgG heavy chain constant region that comprises Arg at position 235, and either or both of Arg at position 236 and Lys at position 239 (all positions according to the EU numbering system), or the part consisting of the amino acid sequence RRGPK (SEQ ID NO: 104) or RRGPS (SEQ ID NO: 117) in the modified IgG heavy chain constant region, the antibody comprises any one of following (a) to (f):

(a) variable regions that comprise
 HVR-H1 comprising the amino acid sequence of SEQ ID NO: 33,
 HVR-H2 comprising the amino acid sequence of SEQ ID NO: 45,
 HVR-H3 comprising the amino acid sequence of SEQ ID NO: 57,
 HVR-L1 comprising the amino acid sequence of SEQ ID NO: 69,
 HVR-L2 comprising the amino acid sequence of SEQ ID NO: 81, and
 HVR-L3 comprising the amino acid sequence of SEQ ID NO: 93;

(b) variable regions that comprise
 HVR-H1 comprising the amino acid sequence of SEQ ID NO: 34,
 HVR-H2 comprising the amino acid sequence of SEQ ID NO: 46,
 HVR-H3 comprising the amino acid sequence of SEQ ID NO: 58,
 HVR-L1 comprising the amino acid sequence of SEQ ID NO: 70,
 HVR-L2 comprising the amino acid sequence of SEQ ID NO: 82, and
 HVR-L3 comprising the amino acid sequence of SEQ ID NO: 94;

(c) variable regions that comprise
 HVR-H1 comprising the amino acid sequence of SEQ ID NO: 37,
 HVR-H2 comprising the amino acid sequence of SEQ ID NO: 49,
 HVR-H3 comprising the amino acid sequence of SEQ ID NO: 61,
 HVR-L1 comprising the amino acid sequence of SEQ ID NO: 73,
 HVR-L2 comprising the amino acid sequence of SEQ ID NO: 85, and
 HVR-L3 comprising the amino acid sequence of SEQ ID NO: 97;

(d) variable regions that comprise

HVR-H1 comprising the amino acid sequence of SEQ ID NO: 38,

HVR-H2 comprising the amino acid sequence of SEQ ID NO: 50,

HVR-H3 comprising the amino acid sequence of SEQ ID NO: 62,

HVR-L1 comprising the amino acid sequence of SEQ ID NO: 74,

HVR-L2 comprising the amino acid sequence of SEQ ID NO: 86, and

HVR-L3 comprising the amino acid sequence of SEQ ID NO: 98;

(e) variable regions that comprise

HVR-H1 comprising the amino acid sequence of SEQ ID NO: 39,

HVR-H2 comprising the amino acid sequence of SEQ ID NO: 51,

HVR-H3 comprising the amino acid sequence of SEQ ID NO: 63,

HVR-L1 comprising the amino acid sequence of SEQ ID NO: 75,

HVR-L2 comprising the amino acid sequence of SEQ ID NO: 87, and

HVR-L3 comprising the amino acid sequence of SEQ ID NO: 99; and (f) variable regions that comprise HVR-H1 comprising the amino acid sequence of SEQ ID NO: 41, HVR-H2 comprising the amino acid sequence of SEQ ID NO: 53, HVR-H3 comprising the amino acid sequence of SEQ ID NO: 65, HVR-L1 comprising the amino acid sequence of SEQ ID NO: 77, HVR-L2 comprising the amino acid sequence of SEQ ID NO: 89, and HVR-L3 comprising the amino acid sequence of SEQ ID NO: 101.

C. Exemplary Antibodies that Specifically Recognize the Modifications Unique to a CH3 Region of the Modified IgG Heavy Chain Constant Region Leu at position 428, Ala at position 434, Arg at position 438, and Glu at position 440 (all positions according to the EU numbering system) are those which specifically exist in CH3 region of SG115 and SG115v2 used in the Examples. Thus, the modified IgG heavy chain constant region in exemplary antibodies here preferably comprises at least a region corresponding to a CH3 region of any one of constant regions in human naturally occurring IgGs or a chimeric constant region obtained from at least two selected from the constant regions in human naturally occurring IgGs.

In one embodiment, the modified IgG heavy chain constant region comprises at least one selected from the group consisting of Leu at position 428, Ala at position 434, Arg at position 438, and Glu at position 440 (all positions according to the EU numbering system). In this embodiment, the modified IgG heavy chain constant region comprises Leu at position 428, Ala at position 434, Arg at position 438, and Glu at position 440, and optionally threonine at position 436 (all positions according to the EU numbering system).

In preferred embodiment, the modified IgG heavy chain constant region comprises all of these mutations. In that case, the antibody binds to the part consisting of the amino acid sequence LHEALHAHYTRKE (SEQ ID NO: 105) or LHEALHAHTTRKE (SEQ ID NO: 118) in the modified IgG heavy chain constant region.

In one aspect where the antibody specifically binds to the modified IgG heavy chain constant region that comprises at least one selected from the group consisting of Leu at position 428, Ala at position 434, Arg at position 438, and Glu at position 440 (all positions according to the EU numbering system), the modified IgG heavy chain constant region that comprises Leu at position 428, Ala at position 434, Arg at position 438, and Glu at position 440 (all positions according to the EU numbering system), or the part consisting of the amino acid sequence LHEALHAHYTRKE (SEQ ID NO: 105) or LHEALHAHTTRKE (SEQ ID NO: 118) in the modified IgG heavy chain constant region, the invention provides an antibody comprising at least one, two, three, four, five, or six HVRs selected from (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; (iii) HVR-H3 comprising the amino acid sequence of SEQ ID NO: 56, 59, 60, 64, 66 or 67; (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103.

In one aspect, the invention provides an antibody comprising at least one, at least two, or all three VH HVR sequences selected from (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; and (iii) HVR-H3 comprising the amino acid sequence of SEQ ID NO: 56, 59, 60, 64, 66 or 67. In one embodiment, the antibody comprises HVR-H3 comprising the amino acid sequence of SEQ ID NO: 56, 59, 60, 64, 66 or 67. In another embodiment, the antibody comprises HVR-H3 comprising the amino acid sequence of SEQ ID NO: 56, 59, 60, 64, 66 or 67 and HVR-L3 comprising the amino acid sequence of SEQ ID NO: 92, 95, 96, 100, 102 or 103. In a further embodiment, the antibody comprises HVR-H3 comprising the amino acid sequence of SEQ ID NO: 56, 59, 60, 64, 66 or 67, HVR-L3 comprising the amino acid sequence of SEQ ID NO: 92, 95, 96, 100, 102 or 103, and HVR-H2 comprising the amino acid sequence of SEQ ID NO: 44, 47, 48, 52, 54 or 55. In a further embodiment, the antibody comprises (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; and (iii) HVR-H3 comprising the amino acid sequence of SEQ ID NO: 56, 59, 60, 64, 66 or 67.

In another aspect, the invention provides an antibody comprising at least one, at least two, or all three VL HVR sequences selected from (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103. In one embodiment, the antibody comprises (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103.

In another aspect, an antibody of the invention comprises (I) a VH domain comprising at least one, at least two, or all three VH HVR sequences selected from (i) HVR-H1 comprising the amino acid sequence of SEQ ID NO: 32, 35, 36, 40, 42 or 43, (ii) HVR-H2 comprising the amino acid sequence of SEQ ID NO: 44, 47, 48, 52, 54 or 55, and (iii) HVR-H3 comprising the amino acid sequence of SEQ ID NO: 56, 59, 60, 64, 66 or 67; and (II) a VL domain comprising at least one, at least two, or all three VL HVR sequences selected from (iv) HVR-L1 comprising the amino acid sequence of SEQ ID NO: 68, 71, 72, 76, 78 or 79, (v) HVR-L2 comprising the amino acid sequence of SEQ ID NO: 80, 83, 84, 88, 90 or 91, and (vi) HVR-L3 comprising the amino acid sequence of SEQ ID NO: 92, 95, 96, 100, 102 or 103.

In another aspect, the invention provides an antibody comprising (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; (iii) HVR-H3 comprising the amino acid sequence of SEQ ID NO: 56, 59, 60, 64, 66 or 67; (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence selected from SEQ ID NO: 92, 95, 96, 100, 102 or 103.

In another aspect, an antibody described herein comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8, 11, 12, 16, 18 or 19. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody described herein comprising that sequence retains the ability to bind to a first modified IgG heavy chain constant region. In certain embodiments, a total of 1 to 10 amino acids have been substituted, inserted and/or deleted in SEQ ID NO: 8, 11, 12, 16, 18 or 19. In certain embodiments, substitutions, insertions, or deletions occur in regions outside the HVRs (i.e., in the FRs). Optionally, the antibody comprises the VH sequence in SEQ ID NO: 8, 11, 12, 16, 18 or 19, including post-translational modifications of that sequence. In a particular embodiment, the VH comprises one, two or three HVRs selected from: (i) HVR-H1 comprising the amino acid sequence of SEQ ID NO: 32, 35, 36, 40, 42 or 43, (ii) HVR-H2 comprising the amino acid sequence of SEQ ID NO: 44, 47, 48, 52, 54 or 55, and (iii) HVR-H3 comprising the amino acid sequence of SEQ ID NO: 56, 59, 60, 64, 66 or 67. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 20, 23, 24, 28, 30 or 31. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an antibody comprising that sequence retains the ability to bind to a first modified IgG heavy chain constant region. In certain embodiments, a total of 1 to 10 amino acids have been substituted, inserted and/or deleted in SEQ ID NO: 20, 23, 24, 28, 30 or 31. In certain embodiments, the substitutions, insertions, or deletions occur in regions outside the HVRs (i.e., in the FRs). Optionally, the antibody comprises the VL sequence in SEQ ID NO: 20, 23, 24, 28, 30 or 31, including post-translational modifications of that sequence. In a particular embodiment, the VL comprises one, two or three HVRs selected from (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103. Post-translational modifications include but are not limited to a modification of glutamine or glutamate in N-terminal of heavy chain or light chain to pyroglutamic acid by pyroglutamylation.

In another aspect, an antibody is provided, wherein the antibody comprises a VH as in any of the embodiments provided above, and a VL as in any of the embodiments provided above. In one embodiment, the antibody comprises the VH and VL sequences in SEQ ID NO: 8, 11, 12, 16, 18 or 19 and SEQ ID NO: 20, 23, 24, 28, 30 or 31, respectively, including post-translational modifications of those sequences. Post-translational modifications include but are not limited to a modification of glutamine or glutamate in N-terminal of heavy chain or light chain to pyroglutamic acid by pyroglutamylation.

In one aspect, an antibody is provided, wherein the antibody competes for binding to the first modified IgG heavy chain constant region with an antibody which comprises: (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; (iii) HVR-H3 comprising the amino acid sequence of SEQ ID NO: 56, 59, 60, 64, 66 or 67; (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103.

In one aspect, an antibody is provided, wherein the antibody binds to the same epitope as an antibody which comprises: (i) HVR-H1 comprising the amino acid sequence of SEQ ID NO: 32, 35, 36, 40, 42 or 43; (ii) HVR-H2 comprising the amino acid sequence of SEQ ID NO: 44, 47, 48, 52, 54 or 55; (iii) HVR-H3 comprising the amino acid sequence of SEQ ID NO: 56, 59, 60, 64, 66 or 67; (iv) HVR-L1 comprising the amino acid sequence of SEQ ID NO: 68, 71, 72, 76, 78 or 79; (v) HVR-L2 comprising the amino acid sequence of SEQ ID NO: 80, 83, 84, 88, 90 or 91; and (vi) HVR-L3 comprising the amino acid sequence of SEQ ID NO: 92, 95, 96, 100, 102 or 103.

In specific embodiments where the antibody specifically binds to the modified IgG heavy chain constant region that comprises at least one selected from the group consisting of Leu at position 428, Ala at position 434, Arg at position 438, and Glu at position 440 (all positions according to the EU numbering system), the modified IgG heavy chain constant region that comprises Leu at position 428, Ala at position 434, Arg at position 438, and Glu at position 440 (all positions according to the EU numbering system), or the part consisting of the amino acid sequence LHEALHAHYTRKE (SEQ ID NO: 105) or LHEALHAHTTRKE (SEQ ID NO: 118) in the modified IgG heavy chain constant region, the antibody comprises any one of following (g) to (1):

(g) variable regions that comprise

HVR-H1 comprising the amino acid sequence of SEQ ID NO: 32,

HVR-H2 comprising the amino acid sequence of SEQ ID NO: 44,

HVR-H3 comprising the amino acid sequence of SEQ ID NO: 56,

HVR-L1 comprising the amino acid sequence of SEQ ID NO: 68,

HVR-L2 comprising the amino acid sequence of SEQ ID NO: 80, and

HVR-L3 comprising the amino acid sequence of SEQ ID NO: 92;

(h) variable regions that comprise

HVR-H1 comprising the amino acid sequence of SEQ ID NO: 35,

HVR-H2 comprising the amino acid sequence of SEQ ID NO: 47,

HVR-H3 comprising the amino acid sequence of SEQ ID NO: 59,

HVR-L1 comprising the amino acid sequence of SEQ ID NO: 71,

HVR-L2 comprising the amino acid sequence of SEQ ID NO: 83, and

HVR-L3 comprising the amino acid sequence of SEQ ID NO: 95;

(i) variable regions that comprise

HVR-H1 comprising the amino acid sequence of SEQ ID NO: 36,

HVR-H2 comprising the amino acid sequence of SEQ ID NO: 48,

HVR-H3 comprising the amino acid sequence of SEQ ID NO: 60,

HVR-L1 comprising the amino acid sequence of SEQ ID NO: 72,

HVR-L2 comprising the amino acid sequence of SEQ ID NO: 84, and

HVR-L3 comprising the amino acid sequence of SEQ ID NO: 96;

(j) variable regions that comprise

HVR-H1 comprising the amino acid sequence of SEQ ID NO: 40,

HVR-H2 comprising the amino acid sequence of SEQ ID NO: 52,

HVR-H3 comprising the amino acid sequence of SEQ ID NO: 64,

HVR-L1 comprising the amino acid sequence of SEQ ID NO: 76,

HVR-L2 comprising the amino acid sequence of SEQ ID NO: 88, and

HVR-L3 comprising the amino acid sequence of SEQ ID NO: 100;

(k) variable regions that comprise

HVR-H1 comprising the amino acid sequence of SEQ ID NO: 42,

HVR-H2 comprising the amino acid sequence of SEQ ID NO: 54,

HVR-H3 comprising the amino acid sequence of SEQ ID NO: 66,

HVR-L1 comprising the amino acid sequence of SEQ ID NO: 78,

HVR-L2 comprising the amino acid sequence of SEQ ID NO: 90, and

HVR-L3 comprising the amino acid sequence of SEQ ID NO: 102; and (1) variable regions that comprise HVR-H1 comprising the amino acid sequence of SEQ ID NO: 43, HVR-H2 comprising the amino acid sequence of SEQ ID NO: 55, HVR-H3 comprising the amino acid sequence of SEQ ID NO: 67, HVR-L1 comprising the amino acid sequence of SEQ ID NO: 79, HVR-L2 comprising the amino acid sequence of SEQ ID NO: 91, and HVR-L3 comprising the amino acid sequence of SEQ ID NO: 103.

D. Other Embodiments

In one embodiment, the antibody in the present invention encompasses an antibody which binds to the same epitope as any one of the antibodies mentioned in the above sections, "A. Modified IgG heavy chain constant region" to "C. Exemplary antibodies that specifically recognize the modifications unique to a CH3 region of the modified IgG heavy chain constant region".

In one embodiment, the antibody in the present invention encompasses an antibody which specifically binds to a modified IgG heavy chain constant region, wherein binding of the antibody to the modified IgG heavy chain constant region competes with the antibodies mentioned in the above sections, "A. Modified IgG heavy chain constant region" to "C. Exemplary antibodies that specifically recognize the modifications unique to a CH3 region of the modified IgG heavy chain constant region". In the embodiment, the modified IgG heavy chain constant region is derived from any one of constant regions in human naturally occurring IgGs or is derived from a chimeric constant region obtained from at least two selected from the constant regions in human naturally occurring IgGs. The modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system). In the embodiment, specific antibodies referred to herein are the same as those in the above sections.

E. Recombinant Methods and Compositions

Antibodies may be produced using recombinant methods and compositions, e.g., as described in U.S. Pat. No. 4,816, 567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an antibody described herein is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody described herein, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

F. Assays

Antibodies provided herein may be identified, screened for, or characterized for their physical/chemical properties and/or biological activities by various assays known in the art.

G. Binding assays and other assays

In one aspect, an antibody of the invention is tested for its antigen binding activity, e.g., by known methods such as ELISA, Western blot, etc.

In another aspect, competition assays may be used to identify an antibody that competes with any one of antibodies used in the Examples (SKA0001, SKA0009, SKA0016, SKA0027, SKA0028, SKA0046, SKA0052, SKA0054, KA0117, SKA0127, SKA0141, and SKA0171) for binding to a modified IgG heavy chain constant region that is derived from any one of constant regions in human naturally occurring IgGs or that is derived from a chimeric constant region obtained from at least two selected from the constant regions in human naturally occurring IgGs, wherein the modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system). In certain embodiments, such a competing antibody may bind to the same epitope (e.g., a linear or a conformational epitope) as the epitope(s) to which any one of antibodies used in the Examples (SKA0001, SKA0009, SKA0016, SKA0027, SKA0028, SKA0046, SKA0052, SKA0054, KA0117, SKA0127, SKA0141, and SKA0171) binds. Detailed exemplary methods for mapping an epitope to which an antibody binds are provided in Morris (1996) "Epitope Mapping Protocols," in Methods in Molecular Biology vol. 66 (Humana Press, Totowa, NJ).

In an exemplary competition assay, an immobilized modified IgG heavy chain constant region is incubated in a solution comprising a labeled antibody that binds to the modified IgG heavy chain constant region and an unlabeled antibody that is being tested for its ability to compete with the labeled antibody for binding to the immobilized modified IgG heavy chain constant region. The unlabeled antibody can be present in a B-cell or hybridoma supernatant. As a control, the immobilized modified IgG heavy chain constant region is incubated in a solution comprising the labeled antibody but not comprising the unlabeled antibody. After incubation under conditions permissive for binding of the labeled antibody to the immobilized modified IgG heavy chain constant region, excess unbound antibody is removed, and the amount of label associated with the immobilized modified IgG heavy chain constant region is measured. If the amount of label associated with the immobilized modified IgG heavy chain constant region is substantially reduced in the test sample relative to the control sample, then that indicates that the unlabeled antibody is competing with the labeled antibody for binding to the immobilized modified IgG heavy chain constant region. See Harlow and Lane (1988) Antibodies: A Laboratory Manual ch. 14 (Cold Spring Harbor Laboratory, Cold Spring Harbor, NY).

III. Composition

In one aspect, a composition in the present invention is a composition for use in detecting or capturing a polypeptide in a sample. The composition comprises any one of the antibodies described in "II. Antibody".

In another aspect, a composition in the present invention is a composition for use in treating or preventing a disease. When the antibody is used for treatment or prevention of any disease, the composition can be or include cells that express any one of the antibodies described in "II. Antibody" or fragments thereof, which specifically bind to a modified IgG heavy chain constant region.

In a preferred embodiment, the polypeptide in the sample comprises a modified IgG heavy chain constant region that is derived from any one of constant regions in human naturally occurring IgGs or that is derived from a chimeric constant region of at least two selected from the constant regions in human naturally occurring IgGs. The modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system). Specific antibodies referred to herein are the same as those described in "II. Antibody".

In another preferred embodiment, the polypeptide comprises any one of the amino acid sequence consisting of RRGPK (SEQ ID NO: 104), the amino acid sequence consisting RRGPS (SEQ ID NO: 117), the amino acid sequence consisting LHEALHAHYTRKE (SEQ ID NO: 105), and the amino acid sequence consisting LHEAL-HAHTTRKE (SEQ ID NO: 118). The polypeptide detected or captured by the composition is not particularly limited in terms of its structure, as long as the polypeptide comprises any one or more of these amino acid sequences. The polypeptide preferably comprises a modified IgG heavy chain constant region that comprises any one or more of the amino acid sequences.

In one embodiment, the polypeptide detected or captured by the composition may be an antibody such as a human IgG1, IgG2, IgG3, or IgG4 molecule, an antibody fragment, a fusion protein, or a polypeptide of any other form comprising the modified IgG heavy chain constant region or an epitope in it.

In the case that the polypeptide comprises the modified IgG heavy chain constant region, the modified IgG heavy chain constant region may comprise other amino acid substitutions or modifications as long as it comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

IV. Method

In one aspect, a method in the present invention is a method for detecting or capturing a polypeptide in a sample. The method comprises contacting a sample with any one of the antibodies described in "II. Antibody" or with any one of the compositions described in "III. Composition".

In a preferred embodiment, the polypeptide comprises a modified IgG heavy chain constant region. The modified IgG heavy chain constant region is derived from any one of constant regions in human naturally occurring IgGs or is derived from a chimeric constant region of at least two selected from the constant regions in human naturally occurring IgGs. The modified IgG heavy chain constant region comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

In another preferred embodiment, the polypeptide comprises any one of the amino acid sequence consisting of RRGPK (SEQ ID NO: 104), the amino acid sequence consisting of RRGPS (SEQ ID NO: 117), the amino acid sequence consisting of LHEALHAHYTRKE (SEQ ID NO: 105), and the amino acid sequence consisting of LHEAL-HAHTTRKE (SEQ ID NO: 118). The polypeptide detected or captured by the method is not particularly limited in terms of its structure, as long as the polypeptide comprises one or more of these amino acid sequences. The polypeptide preferably comprises a modified IgG heavy chain constant region that comprises one or more of these amino acid sequences.

In one embodiment, the polypeptide detected or captured by the method may be an antibody such as a human IgG1, IgG2, IgG3, or IgG4 molecule, an antibody fragment, a fusion protein, or a polypeptide of any other form comprising the modified IgG heavy chain constant region or an epitope in it.

In the case that the polypeptide comprises the modified IgG heavy chain constant region, the modified IgG heavy chain constant region may comprise other amino acid substitutions or modifications as long as it comprises at least one amino acid selected from the group consisting of Arg at position 235, Arg at position 236, Lys at position 239, Gly at position 327, Ser at position 330, Ser at position 331, Leu at position 428, Ala at position 434, Arg at position 438, and Glu at position 440 (all positions according to the EU numbering system).

Figure 3:
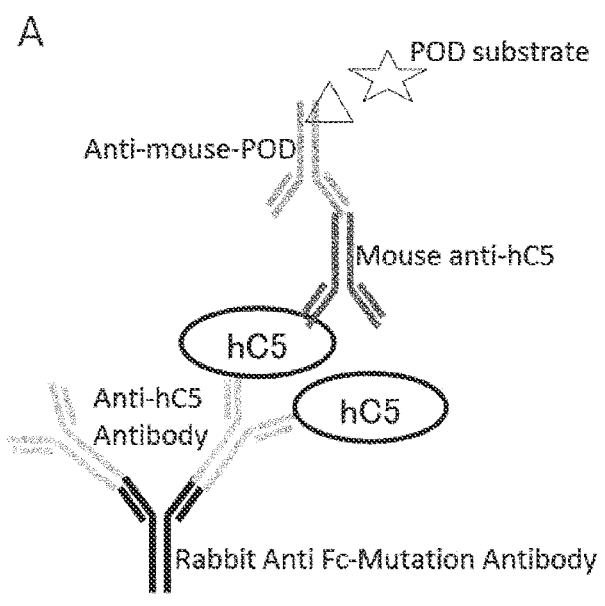
FIG. 3 illustrates a scheme of Fc-Mutated Antibody detection assay.
Figure 3:
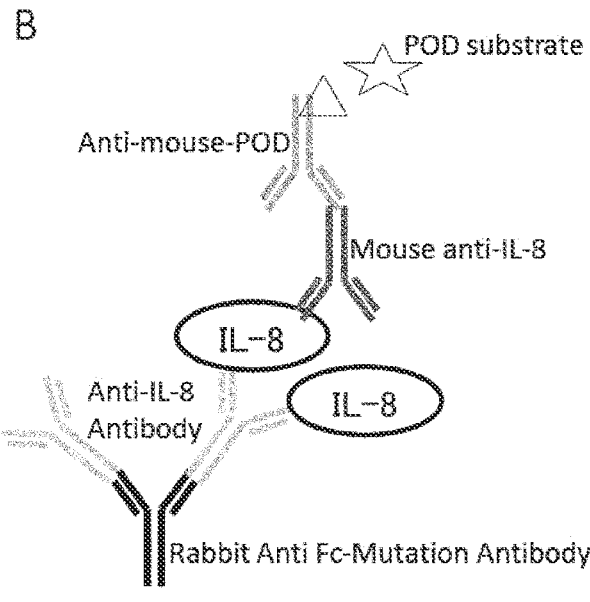

A method by ELISA is illustrated in FIG. 3 as a specific embodiment of the method. "Rabbit Anti Fc-Mutation Antibody" corresponds to one of the antibodies described in "II. Antibody", and "Anti-hC5 Antibody" in FIG. 3A and "Anti-IL-8 Antibody" in FIG. 3B correspond to the the polypeptide comprising the modified IgG heavy chain constant region. Rabbit Anti Fc-Mutation Antibody immobilized on a plate captures Anti-hC5 Antibody in FIG. 3A and Anti-IL-8 Antibody in FIG. 3B in a sample. And then hC5 (human complement 5) as an antigen of Anti-hC5 Antibody, "Mouse anti-hC5" that binds to a different epitope from the epitope to which Anti-hC5 Antibody binds, and Anti-mouse-POD are reacted in this order in FIG. 3A. In FIG. 3B, IL-8 as an antigen of Anti-IL-8 Antibody, "Mouse anti-IL-8" that binds to a different epitope from the epitope to which Anti-IL-8 Antibody binds, and Anti-mouse-POD are reacted in this order. Finally, POD substrate is added on the plate and its luminescent is measured. In this embodiment, when there is a certain amount of the polypeptide comprising the modified IgG heavy chain constant region in a sample, luminescence is detected by a luminometer.

Figure 4:
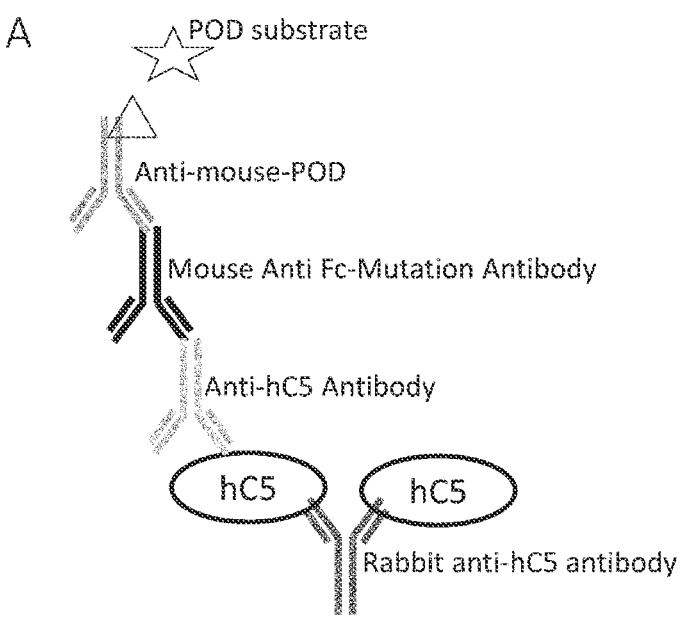
FIG. 4 illustrates a scheme of antigen detection assay.
Figure 4:
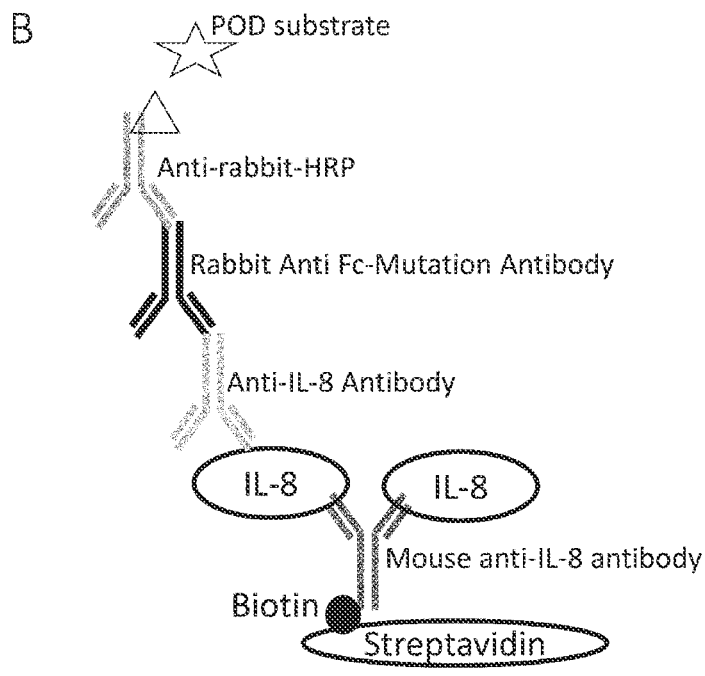

In another embodiment, the antibodies described in "II. Antibody" can be applied for detecting an antigen, such as hC5 and IL-8 as shown in FIG. 4. In this embodiment, "Mouse Anti Fc-Mutation Antibody" and "Rabbit Anti Fc-Mutation Antibody" correspond to one of the antibodies described in "II. Antibody", and "Anti-hC5 Antibody" in FIG. 4A and "Anti-IL-8 Antibody" in FIG. 4B correspond to the polypeptide comprising the modified IgG heavy chain constant region. Rabbit anti-hC5 antibody immobilized on a plate captures hC5 in a sample in FIG. 4A. Mouse anti-IL-8 antibody immobilized on a plate captures IL-8 in a sample in FIG. 4B. And then Anti-hC5 Antibody, Mouse Anti Fc-Mutation Antibody, and Anti-mouse-POD are reacted in this order in FIG. 4A. In FIG. 4B, Anti-IL-8 Antibody, Rabbit Anti Fc-Mutation Antibody, and Anti-rabbit-HRP are reacted in this order. Finally POD (peroxidase), e.g. HRP (Horseradish peroxidase), substrate is added on the plate and its luminescent is measured. In this embodiment, when there is a certain amount of hC5 or IL-8 in a sample, luminescence is detected by a luminometer.

Figure 5:
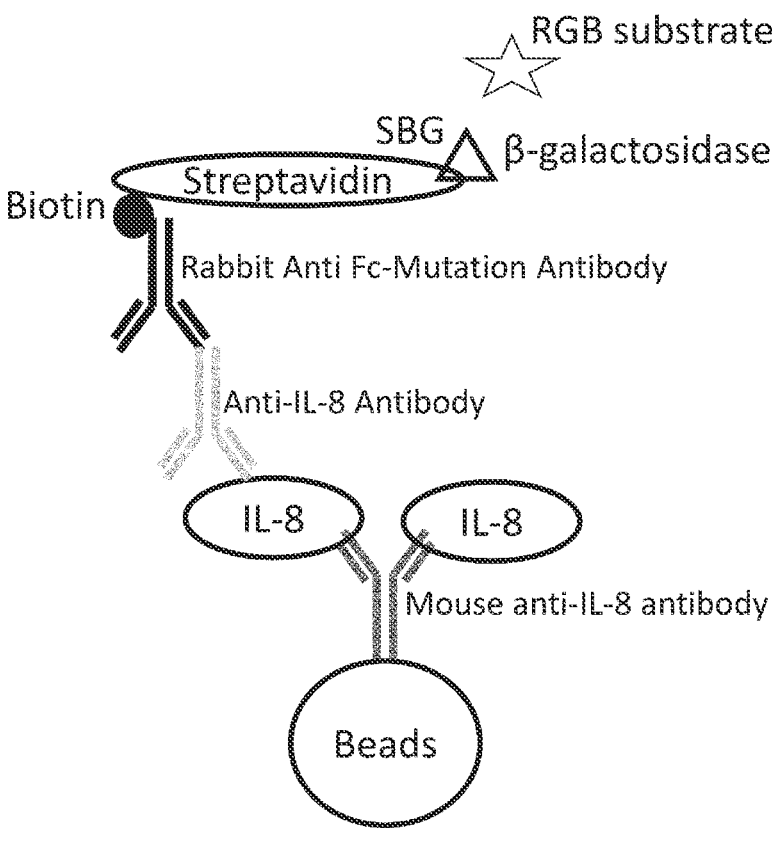
FIG. 5 illustrates a scheme of Simoa (registered trademark) assay.

The above embodiments related to ELISA methods can be replaced by Simoa (registered trademark) assay. In one embodiment of the assay, the antibodies described in "II. Antibody" can be applied for detecting an antigen, such as IL-8 as shown in FIG. 5. In this embodiment, "Rabbit Anti Fc-Mutation Antibody" corresponds to one of the antibodies described in "II. Antibody", and "Anti-IL-8 Antibody" corresponds to the the polypeptide comprising the modified IgG heavy chain constant region. Mouse anti-IL-8 antibody immobilized on beads captures IL-8 in sample. And then Anti-IL-8 Antibody, Biotinylated Anti Fc-Mutation Antibody, and streptavidin-beta-galactosidase (SBG (Quanterix Corporation)) are reacted in this order. Finally, substrate of beta-galactocidase (RGB) is added in the reactant and its luminescence is measured.

Example 1

Preparation of an Antibody Comprising Constant Regions that Comprise Multiple Mutations in an Fc Region Antibody Expression and Purification The antibody comprising constant regions that comprise multiple mutations in an Fc region was expressed by FreeStyle293 expression system. The used constant region (SEQ ID NO: 1) is referred to as SG115 in WO2016098356A1. The harvested cell culture fluid (HCCF) was purified with rProtein A resin (MabSelect SuRe, GE) and Size exclusion chromatography (SEC, Superdex200 pg, GE). In SEC process, we exchanged the buffer to 20 mmol/L Histidine, 150 mmol/L Arginine-Aspartic acid, pH6.0. Finally, the antibody was concentrated to 143 mg/mL using UF (ultrafiltration).

Papain Digestion

For papain digestion, we used Pierce Fab Preparation Kit (Pierce, Cat. No. 44985). The papain digestion process was as described below.

The antibody concentration was adjusted to 8.0 mg/mL with digestion buffer.

0.5 mL of the antibody solution was added to a spin column tube containing the equilibrated papain resin. The top cap and the bottom plug were placed on the spin column.

The digestion reaction solution was incubated on a rotator for 15 hours at 37 degrees C.

After the incubation, the bottom cap was removed and the spin column was placed into a microcentrifuge tube. The column was centrifuged at 5000×g for one minute.

The resin was washed with 0.5 mL of Dulbecco's PBS (−). The spin column was placed into a microcentrifuge tube. The column was centrifuged at 5000×g for one minute.

The solution of step 4 and 5 was mixed as a digested fraction. The total volume was 1.0 mL from one column.

Purification of Fc Fragment

Papain-digested sample was purified with rProtein A resin (MabSelect SuRe, GE) and size exclusion chromatography (SEC, Superdex200 pg, GE). In the SEC process, we removed whole IgG (non-digested molecule) and exchanged the buffer to Dulbecco's PBS (−).

Example 2

Generation of Antibodies that Recognize the Mutations in SG115

Antibodies that recognize the mutations in SG115, referred to as "Anti-SG115 Antibodies", were prepared, selected, and assayed as described below.

Ten week old NZW rabbits were immunized intradermally with Fc fragment of SG115 (50-100 microgram/dose/rabbit). The dose was repeated 5 times over a 2-month period, and then the blood was collected from the immunized rabbits. Antigen-specific B-cells were sorted with cell sorter and then plated and cultured according to the procedure described in WO2016098356A1. After cultivation, B-cell culture supernatants were collected for further analysis and pellets were cryopreserved.

Ability to bind to SG115 was evaluated by ELISA using the B cell culture supernatants. We tested the binding to 5 kinds of modified IgG heavy chain constant regions in order to evaluate the binding specificity: SG115 (SEQ ID NO: 1), SG115v1 (SEQ ID NO: 2), SG115v2 (SEQ ID NO: 3), G1m (SEQ ID NO: 4), and G4d (SEQ ID NO: 5). The sequence alignment of these 5 constant regions is shown in FIG. 1.

A total of 10,560 B-cell lines were screened for the binding to 5 types of modified IgG heavy chain constant regions, and 186 lines were selected and designated as SKA0001-SKA0186, which bound to SG115 but did not to G1m and G4d, and also bound to SG115v1 and/or SG115v2. RNA of the selected lines was purified from cryopreserved cell pellets using ZR-96 Quick-RNA kits (ZYMO RESEARCH, Cat No. R1053). DNA encoding antibody heavy chain variable regions in the selected lines was amplified by reverse transcription PCR and recombined with DNA encoding rbIgGv2 heavy chain constant region (SEQ ID NO: 6). DNA encoding antibody light chain variable regions was amplified by reverse transcription PCR and recombined with DNA encoding rbIgk light chain constant region (SEQ ID NO: 7). The antibodies were expressed in FreeStyle™ 293-F Cells (Invitrogen) and purified from culture supernatant. Through further evaluation, 12 clones were selected based on the binding ability and specificity in ELISA, and sequence variety of heavy chain CDR3. Of these clones, 6 clones (SKA0009, SKA0016, SKA0046, SKA0052, SKA0054 and SKA0127) showed selective binding to SG115v1 but not to SG115v2, while the other 6 clones (SKA0001, SKA0027, SKA0028, SKA0117, SKA0141 and SKA0171) showed selective binding to SG115v2 but not to SG115v1 (FIGS. 2-1 and 2-2). The VH and VL sequences of these 12 antibodies are listed in Table 1.

TABLE 1

| Antibody | Binding | SEQ ID NO. | | | | | | | |
|---|---|---|---|---|---|---|---|---|---|
| Name | Selectivity | VH | HCDR1 | HCDR2 | HCDR3 | VL | LCDR1 | LCDR2 | LCDR3 |
| SKA0001 | SG115v2 | 8 | 32 | 44 | 56 | 20 | 68 | 80 | 92 |
| SKA0009 | SG115v1 | 9 | 33 | 45 | 57 | 21 | 69 | 81 | 93 |
| SKA0016 | SG115v1 | 10 | 34 | 46 | 58 | 22 | 70 | 82 | 94 |
| SKA0027 | SG115v2 | 11 | 35 | 47 | 59 | 23 | 71 | 83 | 95 |
| SKA0028 | SG115v2 | 12 | 36 | 48 | 60 | 24 | 72 | 84 | 96 |
| SKA0046 | SG115v1 | 13 | 37 | 49 | 61 | 25 | 73 | 85 | 97 |
| SKA0052 | SG115v1 | 14 | 38 | 50 | 62 | 26 | 74 | 86 | 98 |
| SKA0054 | SG115v1 | 15 | 39 | 51 | 63 | 27 | 75 | 87 | 99 |
| SKA0117 | SG115v2 | 16 | 40 | 52 | 64 | 28 | 76 | 88 | 100 |
| SKA0127 | SG115v1 | 17 | 41 | 53 | 65 | 29 | 77 | 89 | 101 |
| SKA0141 | SG115v2 | 18 | 42 | 54 | 66 | 30 | 78 | 90 | 102 |
| SKA0171 | SG115v2 | 19 | 43 | 55 | 67 | 31 | 79 | 91 | 103 |

Example 3

Detection of SG115 in Sample by Anti-SG115 Antibodies

For detection of an antibody comprising an Fc region comprising all or part of the mutations in the Fc region of candidates from each epitope type (total 6 candidates) were selected for selectivity test (Table 2). That is, SKA0009, SKA0052, and SKA0127 were selected as antibodies specifically binding to SG115v1, and SKA0117, SKA0141, and SKA0171 were selected as antibodies specifically binding to SG115v2.

TABLE 2

| Epitope type | Antibody name | Incubation period (min) | OD (Blank) | OD (Anti-hC5 Antibody spiked) | Signal to noise ratio | Selected antibodies |
|---|---|---|---|---|---|---|
| SG115v2 | SKA0001 | 18 | 0.032 | 0.079 | 2.5 | — |
| SG115v1 | SKA0009 | 9 | 0.028 | 0.089 | 3.2 | Selected |
| SG115v1 | SKA0016 | 16 | 0.030 | 0.076 | 2.5 | — |
| SG115v2 | SKA0027 | 9 | 0.027 | 0.093 | 3.4 | — |
| SG115v2 | SKA0028 | 16 | 0.030 | 0.091 | 3.0 | — |
| SG115v1 | SKA0046 | 21 | 0.032 | 0.075 | 2.3 | — |
| SG115v1 | SKA0052 | 11 | 0.027 | 0.098 | 3.7 | Selected |
| SG115v1 | SKA0054 | 19 | 0.030 | 0.077 | 2.6 | — |
| SG115v2 | SKA0117 | 9 | 0.027 | 0.112 | 4.1 | Selected |
| SG115v1 | SKA0127 | 14 | 0.028 | 0.078 | 2.8 | Selected |
| SG115v2 | SKA0141 | 8 | 0.026 | 0.109 | 4.2 | Selected |
| SG115v2 | SKA0171 | 8 | 0.027 | 0.106 | 4.0 | Selected |

SG115 (hereinafter also referred to as "Fc-Mutated Antibody" or "Fc-Mutated Antibodies") in biological sample, effectiveness of the above 12 monoclonal antibodies (hereinafter also referred to as "Anti Fc-Mutation Antibody" or "Anti Fc-Mutation Antibodies") was evaluated. A specific anti-human C5 antibody comprising SG115 was used as a model of Fc-Mutated Antibody in EXAMPLEs 3-5, which is hereinafter referred to as "Anti-hC5 Antibody".

Assay Procedures

Each well of ninety six-well immunoplate was coated with a rabbit Anti Fc-Mutation Antibody and blocked with blocking buffer. Diluted serum samples were added to each well of the plate. Recombinant human C5 was added to each well of the plate. Mouse Anti-hC5 Antibody was added followed by the addition of anti-mouse-POD (Jackson ImmunoResearch Inc.). Finally, POD substrate was added to each well of the plate and OD was measured. The plate was washed between the steps.

Reactivity Test for Antibody Selection

Twelve of the Anti Fc-Mutation Antibodies were tested. Anti-hC5 Antibody comprising SG115 was diluted with pooled human serum and measured using 12 candidates of rabbit Anti Fc-Mutation Antibodies. Signal to noise ratio was calculated. Measured OD is tabulated in Table 2. Three Selectivity Test for Antibody Selection Ten individual sera with or without spiked Anti-hC5 Antibody and calibration curve samples were measured using the 6 candidate antibodies as capture reagents. Without spiked Anti-hC5 Antibody, measured concentrations of all individual samples were below limit of quantitation (BLQ) in any given rabbit Anti Fc-Mutation Antibodies. With spiked Anti-hC5 Antibody, relative error (RE) of measured concentrations of all individual samples were within +/−20% in any given rabbit Anti Fc-Mutation Antibodies (Table 3).

TABLE 3

| Antibody name | Nominal Anti-hC5 Antibody concentration: 0 ng/mL Measured concentration range in serum (ng/mL) | Nominal Anti-hC5 Antibody concentration: 100 ng/mL | |
|---|---|---|---|
| | | Measured concentration range in serum (ng/mL) | RE range (%) |
| SKA0009 | All individual samples were BLQ | 88.5 to 95.9 | −11.5to −4.1 |
| SKA0052 | All individual samples were BLQ | 93.3 to 99.2 | −6.7to −0.8 |
| SKA0127 | All individual samples were BLQ | 90.4 to 99.2 | −9.6to −0.8 |

TABLE 3-continued

| Antibody name | Nominal Anti-hC5 Antibody concentration: 0 ng/mL Measured concentration range in serum (ng/mL) | Nominal Anti-hC5 Antibody concentration: 100 ng/mL | |
| --- | --- | --- | --- |
| | | Measured concentration range in serum (ng/mL) | RE range (%) |
| SKA0141 | All individual samples were BLQ | 91.5 to 97.0 | −8.5 to −3.0 |
| SKA0171 | All individual samples were BLQ | 90.5 to 97.2 | −9.5 to −2.8 |
| SKA0117 | All individual samples were BLQ | 87.5 to 97.8 | −12.5 to −2.2 |

BLQ: Below the limit of quantitation

Selected Antibody

According to the results from reactivity test and selectivity test, SKA0141 which had the highest signal to noise ratio was selected.

Example 4

Evaluation of the method to measure Anti-hC5 Antibody in human serum (Fc-Mutated Antibody detection assay)

Assay Procedures

Ninety six well immunoplate was coated with the rabbit Anti Fc-Mutation Antibody (SKA0141) and blocked with blocking buffer. Diluted serum samples including Anti-hC5 Antibody were added to each well of the plate. Recombinant human C5 was added to each well of the plate. Mouse anti-hC5 monoclonal antibody was added followed by the addition of anti-mouse-POD (Jackson ImmunoResearch Inc.). Finally, POD substrate was added to each well of the plate and OD was measured. The plate was washed between the steps.

Method Evaluation

Reproducibility was tested. Intra-batch accuracy (RE) and precision (CV) were −16.3% to −5.1% and 1.6% to 4.4% respectively (Table 4). Inter-batch accuracy (RE) and precision (CV) were −10.1% to −4.0% and 2.7% to 6.9% respectively (Table 5).

TABLE 4

| | Measured concentration in serum (ng/mL) | | | | |
| --- | --- | --- | --- | --- | --- |
| | 50 ng/mL | 100 ng/mL | 400 ng/mL | 2560 ng/mL | 3200 ng/mL |
| | 47.7 | 97.2 | 385 | 2179 | 2642 |
| | 46.4 | 94.3 | 383 | 2337 | 2698 |
| | 46.6 | 93.3 | 372 | 2176 | 2702 |
| | 48.2 | 97.7 | 383 | 2177 | 2676 |
| | 47.1 | 93.1 | 380 | 2359 | 2759 |
| | 46.2 | 93.3 | 377 | 2084 | 2504 |
| | 47.1 | 97.0 | 387 | 2137 | 2606 |
| | 46.2 | 93.6 | 364 | 2261 | 2850 |
| Mean | 46.9 | 94.9 | 379 | 2214 | 2680 |
| CV (%) | 1.6 | 2.1 | 2.0 | 4.4 | 3.8 |
| RE (%) | −6.2 | −5.1 | −5.3 | −13.5 | −16.3 |
| n | 8 | 8 | 8 | 8 | 8 |

TABLE 5

| | Measured concentration in serum (ng/mL) | | | | |
| --- | --- | --- | --- | --- | --- |
| Assay run | 50 ng/mL | 100 ng/mL | 400 ng/mL | 2560 ng/mL | 3200 ng/mL |
| 1 | 47.7 | 97.2 | 385 | 2179 | 2642 |
| | 46.4 | 94.3 | 383 | 2337 | 2698 |

TABLE 5-continued

| | Measured concentration in serum (ng/mL) | | | | |
| --- | --- | --- | --- | --- | --- |
| Assay run | 50 ng/mL | 100 ng/mL | 400 ng/mL | 2560 ng/mL | 3200 ng/mL |
| | 46.6 | 93.3 | 372 | 2176 | 2702 |
| | 48.2 | 97.7 | 383 | 2177 | 2676 |
| | 47.1 | 93.1 | 380 | 2359 | 2759 |
| | 46.2 | 93.3 | 377 | 2084 | 2504 |
| | 47.1 | 97.0 | 387 | 2137 | 2606 |
| | 46.2 | 93.6 | 364 | 2261 | 2850 |
| 2 | 46.9 | 96.8 | 392 | 2215 | 2727 |
| | 46.6 | 98.7 | 401 | 2392 | 2967 |
| | 45.7 | 101 | 412 | 2315 | 3201 |
| | 47.7 | 104 | 411 | 2428 | 2992 |
| | 50.3 | 98.4 | 411 | 2650 | 3180 |
| | 50.3 | 104 | 408 | 2361 | 2975 |
| 3 | 48.3 | 93.0 | 374 | 2372 | 2938 |
| | 47.2 | 93.3 | 359 | 2412 | 3034 |
| | 48.0 | 92.7 | 376 | 2393 | 3060 |
| | 48.3 | 92.4 | 371 | 2371 | 3065 |
| | 45.4 | 91.8 | 376 | 2558 | 2992 |
| | 47.5 | 93.0 | 359 | 2345 | 2955 |
| Mean | 47.4 | 95.9 | 384 | 2326 | 2876 |
| CV (%) | 2.7 | 3.9 | 4.4 | 6.0 | 6.9 |
| RE (%) | −5.3 | −4.1 | −4.0 | −9.1 | −10.1 |
| n | 20 | 20 | 20 | 20 | 20 |

Selectivity was tested. Without spiked Anti-hC5 Antibody, measured concentrations of all individual samples were BLQ. With spiked Anti-hC5 Antibody, RE of measured concentrations of all individual samples were −15.2% to 2.2% (Table 6).

TABLE 6

| Individual No. | Measured concentration in serum (ng/mL) | | | | |
| --- | --- | --- | --- | --- | --- |
| | 0 ng/mL | 50.0 ng/mL | RE (%) | 3200 ng/mL | RE (%) |
| 1 | BLQ | 44.1 | −11.8 | 2855 | −10.8 |
| 2 | BLQ | 43.1 | −13.7 | 2935 | −8.3 |
| 3 | BLQ | 42.4 | −15.2 | 3024 | −5.5 |
| 4 | BLQ | 43.1 | −13.7 | 2995 | −6.4 |
| 5 | BLQ | 42.6 | −14.7 | 2927 | −8.5 |
| 6 | BLQ | 43.9 | −12.3 | 3010 | −5.9 |
| 7 | BLQ | 43.9 | −12.3 | 2987 | −6.6 |
| 8 | BLQ | 46.3 | −7.4 | 2981 | −6.8 |
| 9 | BLQ | 44.8 | −10.3 | 3091 | −3.4 |
| 10 | BLQ | 43.6 | −12.8 | 3270 | 2.2 |

Dilution linearity was tested. One milligram per milliliter of Anti-hC5 Antibody could be measured in dilution factor 50,000-fold and prozone effect was not observed. (Table 7).

TABLE 7

| Nominal concentration in serum (ng/mL) | Dilution factor | Concentration in assay sample (ng/mL) | Measured concentration in assay sample (ng/mL) | Mean measured concentration in assay sample (ng/mL) | RE (%) | CV (%) |
|---|---|---|---|---|---|---|
| 1,000,000 | 50 | 20,000 | ALQ<br>ALQ<br>ALQ | — | — | — |
| | 500 | 2,000 | ALQ<br>ALQ<br>ALQ | — | — | — |
| | 5000 | 200 | ALQ<br>ALQ<br>ALQ | — | — | — |
| | 50,000 | 20 | 19.0<br>18.2<br>18.2 | 18.5 | −7.6 | 2.7 |

ALQ: Above limit of quantitation

Interference from C5 was tested. Interference from C5 [20] was not observed (Table 8).

TABLE 8

| Nominal Anti–hC5 Antibody concentration in serum (ng/mL) | Spiked hC5 concentration in serum (μg/mL) | Measured Anti–hC5 Antibody concentration in serum (ng/mL) | RE (%) |
|---|---|---|---|
| 2560 | 500 | 2405 | −6.1 |
| 2560 | 50.0 | 2396 | −6.4 |
| 2560 | 0 | 2376 | −7.2 |
| 400 | 500 | 403 | 0.8 |
| 400 | 50.0 | 419 | 4.8 |
| 400 | 0 | 398 | −0.5 |
| 100 | 500 | 102 | 1.7 |
| 100 | 50.0 | 102 | 2.4 |
| 100 | 0 | 95.0 | −5.0 |

A method to measure an Fc-Mutated Antibody in human serum using an Anti Fc-Mutation Antibody was established. The scheme of this assay is illustrated in FIG. 3.

Example 5

We also tried to establish an assay for detecting an antigen that is recognized by an Fc-Mutated Antibody in a biological sample. Anti-hC5 Antibody was also used as a model of [25] Fc-Mutated Antibody in this evaluation.
Evaluation of the Method to Measure C5 in Human Serum (Antigen Detection Assay) Assay Procedures Ninety six well immunoplate was coated with rabbit ant-hC5 monoclonal antibody and blocked with blocking [30] buffer. Diluted serum samples were added to each well of the plate. Anti-hC5 Antibody was added to each well of the plate. The mouse Anti Fc-Mutation Antibody which was obtained by substitution of the Fc region in SKA0141 to mouse Fc region was added to each well of the plate followed by the addition of anti-mouse-POD (Jackson [35] ImmunoResearch Inc.). Finally, POD substrate was added to each well of the plate and OD was measured. The plate was washed between the steps.
Method Evaluation Reproducibility was tested. Intra-batch accuracy (RE) and [40] precision (CV) were-8.2% to 4.2% and 2.3% to 6.2% respectively (Table 9). Inter-batch accuracy (RE) and precision (CV) were −6.8% to 1.3% and 3.5% to 6.2% respectively (Table 10).

TABLE 9

| | Measured concentration in serum (μg/mL) | | | | |
|---|---|---|---|---|---|
| | 3.25 μg/mL* | 6.50 μg/mL* | 89.1 μg/mL† | 154 μg/mL‡ | 208 μg/mL* |
| | 3.10 | 6.31 | 97.1 | 171 | 198 |
| | 3.45 | 6.53 | 95.1 | 152 | 196 |
| | 3.10 | 6.36 | 92.3 | 153 | 193 |
| | 3.31 | 6.36 | 91.1 | 149 | 188 |
| | 3.10 | 6.25 | 91.5 | 148 | 187 |
| | 2.96 | 6.08 | 89.7 | 144 | 185 |
| Mean | 3.17 | 6.32 | 92.8 | 153 | 191 |
| CV (%) | 5.6 | 2.3 | 3 | 6.2 | 2.8 |
| RE (%) | −2.5 | −2.8 | 4.2 | −0.6 | −8.2 |
| n | 6 | 6 | 6 | 6 | 6 |

*Recombinant human C5 was spiked in C5 depleted serum.

†Pooled human serum (endogenous human C5). The concentration was mean measured concentration in inter batch reproducibility test.

‡Recombinant human C5 was spiked in pooled human serum. The concentration was endogenous human C5 concentration (89.1 μg/mL) + spiked recombinant human C5 concentration (65.0 μg/mL).

TABLE 10

| | Measured concentration in serum (ug/mL) | | | | |
|---|---|---|---|---|---|
| Assay run | 3.25 ug/mL* | 6.50 ug/mL* | 89.1 ug/mL† | 154 pg/mL‡ | 208 ug/mL* |
| 1 | 3.10 | 6.31 | 97.1 | 171 | 198 |
| | 3.45 | 6.53 | 95.1 | 152 | 196 |
| | 3.10 | 6.36 | 92.3 | 153 | 193 |
| | 3.31 | 6.36 | 91.1 | 149 | 188 |
| | 3.10 | 6.25 | 91.5 | 148 | 187 |
| | 2.96 | 6.08 | 89.7 | 144 | 185 |
| 2 | 3.07 | 6.17 | 87.7 | 160 | 206 |
| | 3.15 | 6.23 | 88.9 | 161 | 205 |
| | 2.84 | 5.92 | 86.6 | 159 | 203 |
| | 2.92 | 5.85 | 81.8 | 157 | 206 |
| | 3.31 | 5.92 | 85.8 | 151 | 196 |
| | 2.84 | 6.11 | 83.7 | 155 | 201 |
| 3 | 2.86 | 6.72 | 91.2 | 159 | 201 |
| | 3.08 | 6.2 | 90.9 | 157 | 206 |
| | 2.86 | 6.14 | 89.6 | 157 | 197 |
| | 2.86 | 6.03 | 86.7 | 160 | 208 |
| | 2.86 | 5.85 | 87.2 | 159 | 196 |
| | 2.86 | 5.73 | 87.6 | 156 | 201 |
| Mean | 3.03 | 6.15 | 89.1 | 156 | 199 |
| CV (%) | 6.20 | 4.1 | 4.2 | 3.9 | 3.5 |
| RE (%) | −6.8 | −5.4 | — | 1.3 | −4.3 |
| n | 18 | 18 | 18 | 18 | 18 |

*Recombinant human C5 was spiked in C5 depleted serum.
†Pooled human serum (endogenous human C5). The concentration was mean measured concentration in inter batch reproducibility test.
‡Recombinant human C5 was spiked in pooled human serum. The concentration was endogenous human C5 concentration (89.1 μg/mL) + spiked recombinant human C5 concentration (65.0 ug/mL).

Parallelism was tested. Ten individual sera were serially diluted from 325-fold to 2600-fold and measured. In any dilution factors, measured concentrations were recovered (Table 11).

TABLE 11

| Individual human serum No. | Dilution factor | Measured Concentration in serum (μg/mL) |
|---|---|---|
| 1 | 325 | 73.3 |
| | 650 | 75.1 |
| | 1300 | 74.3 |
| | 2600 | 74.7 |
| 2 | 325 | 88.5 |
| | 650 | 90.5 |
| | 1300 | 92.0 |
| | 2600 | 90.4 |
| 3 | 325 | 59.1 |
| | 650 | 57.7 |
| | 1300 | 57.9 |
| | 2600 | 59.4 |
| 4 | 325 | 86.2 |
| | 650 | 89.3 |
| | 1300 | 88.1 |
| | 2600 | 89.6 |
| 5 | 325 | 76.5 |
| | 650 | 77.6 |
| | 1300 | 76.7 |
| | 2600 | 76.8 |
| 6 | 325 | 78.2 |
| | 650 | 83.0 |
| | 1300 | 84.3 |
| | 2600 | 84.0 |
| 7 | 325 | 56.2 |
| | 650 | 56.0 |
| | 1300 | 54.5 |
| | 2600 | 54.2 |
| 8 | 325 | 63.9 |
| | 650 | 65.8 |
| | 1300 | 66.1 |
| | 2600 | 66.4 |

TABLE 11-continued

| Individual human serum No. | Dilution factor | Measured Concentration in serum (μg/mL) |
|---|---|---|
| 9 | 325 | 65.2 |
| | 650 | 64.8 |
| | 1300 | 65.0 |
| | 2600 | 66.7 |
| 10 | 325 | 89.4 |
| | 650 | 94.3 |
| | 1300 | 95.5 |
| | 2600 | 96.7 |

Dilution linearity was tested. One thousand one hundred and thirty microgram per milliliter of C5 could be measured in dilution factor of 26,000-fold and prozone effect was not observed. (Table 12).

TABLE 12

| Nominal Concentration in serum (μg/mL) | Dilution Factor | Measured concentration in diluted sample (μg/mL) | Mean measured concentration in serum sapmple (μg/mL) | RE (%) |
|---|---|---|---|---|
| 1130 | 650 | ALQ | — | — |
| | | ALQ | — | — |
| | | ALQ | — | — |
| 1130 | 2080 | ALQ | — | — |
| | | ALQ | — | — |
| | | ALQ | — | — |
| 1130 | 26,000 | 0.0439 | 1140 | 0.9 |
| | | 0.0421 | 1090 | −3.5 |
| | | 0.0414 | 1080 | −4.4 |

ALQ: Above limit of quantitation

Interference from Anti-hC5 Antibody was tested. Interference from Anti-hC5 Antibody was not observed (Table 13).

TABLE 13

| hC5 nominal concentration (μg/mL) | Spiked Anti–hC5 Antibody concentration (μg/mL) | Measured C5 concentration in serum (μg/mL) | RE (%) |
|---|---|---|---|
| 6.5 | 0 | 6.14 | −5.5 |
| | 6.50 | 5.41 | −16.8 |
| | 65.0 | 5.57 | −14.3 |
| | 650 | 5.80 | −10.8 |
| 87.3 | 0 | 91.3 | 4.6 |
| | 6.50 | 92.6 | 6.1 |
| | 65.0 | 93.7 | 7.3 |
| | 650 | 104 | 19.1 |
| 154 | 0 | 149 | −3.2 |
| | 6.50 | 150 | −2.6 |
| | 65.0 | 153 | −0.6 |
| | 650 | 167 | 8.4 |

A method to measure an antigen in human serum using an Anti Fc-Mutation Antibody was established. The scheme of this assay is illustrated in FIG. 4.

Example 6

Evaluation of the Method to Measure Anti-IL-8 Antibody in Human Plasma (Fc-Mutated Antibody Detection Assay)

Assay Procedures

A specific anti-human IL-8 antibody that comprises a modified IgG heavy chain constant region comprising part of the mutations in the Fc region of SG115 (SEQ ID NO: 110) was used as a model of Fc-Mutated Antibody in EXAMPLEs 6-8, which is hereinafter referred to as "Anti-IL-8 Antibody".

Ninety six well immunoplate was coated with one of rabbit Anti Fc-Mutation Antibodies (SKA0117) and blocked with blocking buffer. Diluted plasma samples were added to each well of the plate. Recombinant human IL-8 (SEQ ID NO: 111) was added to each well of the plate. Mouse anti-IL-8 monoclonal antibody (a heavy chain variable region, SEQ ID NO: 112; a light chain variable region, SEQ ID NO: 113; a heavy chain constant region, SEQ ID NO: 114; a light chain constant region, SEQ ID NO: 115) was added followed by the addition of anti-mouse-POD (Jackson ImmunoResearch Inc.). Finally, POD substrate was added to each well of the plate and OD was measured. The plate was washed between the steps.

Method Evaluation

Reproducibility was tested. Anti-IL-8 Antibody of known concentration (50.0 ng/ML (REP-LL), 100 ng/ML (REP-L), 400 ng/ML (REP-M), 2400 ng/ML (REP-H), and 3200 ng/ml (REP-UL)) was measured. Intra-batch accuracy (RE) and precision (CV) were −14.2% to −9.7% and 4.9% to 7.3% respectively (Table 14).

TABLE 14

| | Run ID | REP-LL 50.0 ng/mL | % RE | REP-L 100 ng/mL | % RE | REP-M 400 ng/mL | % RE | REP-H 2400 ng/mL | % RE | REP-UL 3200 ng/mL | % RE |
|---|---|---|---|---|---|---|---|---|---|---|---|
| | 2 | 47.3 | −5.4 | 93.0 | −7.0 | 368 | −8.0 | 2340 | −2.5 | 3080 | −3.8 |
| | | 47.6 | −4.8 | 96.5 | −3.5 | 401 | 0.3 | 2100 | −12.5 | 2850 | −10.9 |
| | | 43.9 | −12.2 | 91.2 | −8.8 | 352 | −12.0 | 2040 | −15.0 | 2830 | −11.6 |
| | | 45.6 | −8.8 | 89.1 | −10.9 | 354 | −11.5 | 1950 | −18.8 | 2680 | −16.3 |
| | | 42.2 | −15.6 | 83.5 | −16.5 | 340 | −15.0 | 1990 | −17.1 | 2910 | −9.1 |
| | | 43.2 | −13.6 | 88.4 | −11.6 | 344 | −14.0 | 1930 | −19.6 | 2690 | −15.9 |
| Mean | | 45.0 | | 90.3 | | 360 | | 2060 | | 2840 | |
| % CV | | 4.9 | | 4.9 | | 6.2 | | 7.3 | | 5.2 | |
| % RE | | −10.0 | | −9.7 | | −10.0 | | −14.2 | | −11.3 | |
| % Total Error | | 14.9 | | 14.6 | | 16.2 | | 21.5 | | 16.5 | |
| n | | 6 | | 6 | | 6 | | 6 | | 6 | |

Inter-batch accuracy (RE) and precision (CV) were −10.3% to −6.6% and 7.0% to 10.1% respectively (Table 15).

TABLE 15

| | Run ID | REP-LL 50.0 ng/mL | % RE | REP-L 100 ng/mL | % RE | REP-M 400 ng/mL | % RE | REP-H 2400 ng/mL | % RE | REP-UL 3200 ng/mL | % RE |
|---|---|---|---|---|---|---|---|---|---|---|---|
| | 5 | 47.3 | −5.4 | 93.0 | −7.0 | 368 | −8.0 | 2340 | −2.5 | 3080 | −3.8 |
| | | 47.6 | −4.8 | 96.5 | −3.5 | 401 | 0.3 | 2100 | −12.5 | 2850 | −10.9 |
| | | 43.9 | −12.2 | 91.2 | −8.8 | 352 | −12.0 | 2040 | −15.0 | 2830 | −11.6 |
| | 3 | 42.3 | −15.4 | 89.9 | −10.1 | 359 | −10.3 | 2370 | −1.3 | 3190 | −0.3 |
| | | 41.1 | −17.8 | 90.5 | −9.5 | 361 | −9.8 | 2290 | −4.6 | 3090 | −3.4 |
| | | 42.3 | −15.4 | 91.4 | −8.6 | 367 | −8.3 | 2250 | −6.3 | 2980 | −6.9 |
| | 4 | 44.8 | −10.4 | 81.8 | −18.2 | 326 | −18.5 | 2450 | 2.1 | 3600 | 12.5 |
| | | 45.7 | −8.6 | 81.1 | −18.9 | 310 | −22.5 | 2160 | −10.0 | 2880 | −10.0 |
| | | 44.4 | −11.2 | 82.0 | −18.0 | 322 | −19.5 | 2310 | −3.8 | 2950 | −7.8 |
| | 6 | 49.8 | −0.4 | 92.8 | −7.2 | 379 | −5.3 | 2450 | 2.1 | 3310 | 3.4 |
| | | 49.2 | −1.6 | 96.9 | −3.1 | 385 | −3.8 | 2310 | −3.8 | 2870 | −10.3 |
| | | 48.5 | −3.0 | 96.6 | −3.4 | 399 | −0.3 | 2390 | −0.4 | 3080 | −3.8 |

TABLE 15-continued

| Run ID | REP-LL 50.0 ng/mL | % RE | REP-L 100 ng/mL | % RE | REP-M 400 ng/mL | % RE | REP-H 2400 ng/mL | % RE | REP-UL 3200 ng/mL | % RE |
|---|---|---|---|---|---|---|---|---|---|---|
| 7 | 51.2 | 2.4 | 99.5 | −0.5 | 388 | −3.0 | 2290 | −4.6 | 3020 | −5.6 |
|  | 52.3 | 4.6 | 105 | 5.0 | 405 | 1.3 | 2310 | −3.8 | 2940 | −8.1 |
|  | 52.3 | 4.6 | 100 | 0.0 | 406 | 1.5 | 2140 | −10.8 | 2920 | −8.8 |
| 8 | 43.3 | −13.4 | 84.1 | −15.9 | 316 | −21.0 | 2150 | −10.4 | 2960 | −7.5 |
|  | 44.2 | −11.6 | 79.5 | −20.5 | 299 | −25.3 | 1850 | −22.9 | 2690 | −15.9 |
|  | 44.2 | −11.6 | 82.3 | −17.7 | 313 | −21.8 | 2100 | −12.5 | 2600 | −18.8 |
| Mean | 46.4 |  | 90.8 |  | 359 |  | 2240 |  | 2990 |  |
| % CV | 7.6 |  | 8.3 |  | 10.1 |  | 7.0 |  | 7.6 |  |
| % RE | −7.2 |  | −9.2 |  | −10.3 |  | −6.7 |  | −6.6 |  |
| % Total Error | 14.8 |  | 17.5 |  | 20.3 |  | 13.6 |  | 14.1 |  |
| n | 18 |  | 18 |  | 18 |  | 18 |  | 18 |  |

Selectivity was tested. Without spiked Anti-IL-8 Antibody (SEL-O or SEL-EM-O), measured concentrations of all individual samples were BLQ. With spiked Anti-IL-8 Antibody (50.0 ng/ml (SEL-LL or SEL-EM-LL)), RE of measured concentrations of all individual samples were −23.2% to −4.3% (Table 16).

Interference from IL-8 was tested. IL-8 up to 50.0 ng/ml did not interfere with the assay at Anti-IL-8 Antibody concentration of 2400 ng/ml, and IL-8 up to 1.00 ng/ml did not interfere with the assay at Anti-IL-8 Antibody concentration of 50.0 ng/ml (Table 18).

TABLE 16

| Run ID | Individual human plasma No. | SEL−0 or SEL−EM−0 0.00 ng/mL | % RE | SEL−LL or SEL−EM−LL 50.0 ng/mL | % RE |
|---|---|---|---|---|---|
| 1 | No. 1 | BLQ* | —— | 46.5 | −7.0 |
|  | No. 2 | BLQ* | — | 42.6 | −14.8 |
|  | No. 3 | BLQ* | — | 42.6 | −14.8 |
|  | No. 4 | BLQ* | — | 43.6 | −12.8 |
|  | No. 5 | BLQ* | — | 40.7 | −18.6 |
|  | No. 6 | BLQ* | — | 44.1 | −11.8 |
|  | No. 7 | BLQ* | — | 47.0 | −6.0 |
|  | No. 8 | BLQ* | — | 47.6 | −4.8 |
|  | No. 9 | BLQ* | — | 43.4 | −13.2 |
|  | No. 10 | BLQ* | — | 43.1 | −13.8 |
|  | No. 1 of endometriosis donors | BLQ* | — | 39.9 | −20.2 |
|  | No. 2 of endometriosis donors | BLQ* | — | 38.4 | −23.2 |
|  | No. 3 of endometriosis donors | BLQ* | — | 39.4 | −21.2 |
|  | No. 4 of endometriosis donors | BLQ* | — | 44.9 | −10.2 |

*Below the lower limit of quantification

Dilution linearity was tested. One point six milligram per milliliter of Anti-IL-8 Antibody could be measured in dilution factor of 10,000-fold and prozone effect was not observed (Table 17).

TABLE 17

| Sample name | Conc. in plasma (ng/mL) | Dilution Factor (including MRD) | Conc. in assay well (ng/mL) | Measured value (ng/mL) | Mean (ng/mL) | % RE | % CV |
|---|---|---|---|---|---|---|---|
| DIL-10000 | 1,600,000 | 500,000 | 3.20 | 1,490,000 | 1,530,000 | −4.4 | 2.3 |
|  |  |  |  | 1,560,000 |  |  |  |
|  |  |  |  | 1,530,000 |  |  |  |
| DIL-1000 | 1,600,000 | 50,000 | 32.0 | 1,520,000 | 1,530,000 | −4.4 | 4.6 |
|  |  |  |  | 1,610,000 |  |  |  |
|  |  |  |  | 1,470,000 |  |  |  |
| DIL-100 | 1,600,000 | 5,000 | 320 | ALQ* | — | — | — |
|  |  |  |  | ALQ* |  |  |  |
|  |  |  |  | ALQ* |  |  |  |
| DIL-10 | 1,600,000 | 500 | 3200 | ALQ* | — | — | — |
|  |  |  |  | ALQ* |  |  |  |
|  |  |  |  | ALQ* |  |  |  |

Quantification range: 1.00 ng/mL~64.0 ng/mL in assay well
*Above the upper limit of quantification

TABLE 18

| Sample name | Anti-IL-8 Antibody conc. in plasma (ng/mL) | IL-8 conc. in plasma (ng/mL) | Measured value (ng/mL) | % RE | Mean (% RE) |
|---|---|---|---|---|---|
| IntH-H | 2400 | 200 | 3490 | 45.4 | 3570 (48.8) |
|  |  |  | 3640 | 51.7 |  |
| IntM-H | 2400 | 100 | 2990 | 24.6 | 2990 (24.6) |
|  |  |  | 2980 | 24.2 |  |
| IntL-H | 2400 | 50.0 | 2660 | 10.8 | 2610 (8.8) |
|  |  |  | 2550 | 6.3 |  |
| H-Cnt | 2400 | 0 | 2070 | −13.8 | 2060 (−14.2) |
|  |  |  | 2040 | −15.0 |  |
| IntH-LL | 50.0 | 10.0 | 70.4 | 40.8 | 72.6 (45.2) |
|  |  |  | 74.8 | 49.6 |  |
| IntM-LL | 50.0 | 5.00 | 64.0 | 28.0 | 64.7 (29.4) |
|  |  |  | 65.3 | 30.6 |  |
| IntL-LL | 50.0 | 1.00 | 56.6 | 13.2 | 55.9 (11.8) |
|  |  |  | 55.2 | 10.4 |  |
| LL-Cnt | 50.0 | 0 | 49.2 | −1.6 | 48.2 (−3.6) |
|  |  |  | 47.2 | −5.6 |  |

The effectiveness of the method to measure Anti-IL-8 Antibody in plasma was confirmed.

Example 7

Evaluation of the Method to Measure IL-8 in Human Plasma Using ELISA (Antigen Detection Assay)

Assay Procedures

Ninety six well streptavidin immunoplate was coated with biotinylated mouse ant-IL-8 monoclonal antibody after blocked with blocking buffer. Anti-IL-8 Antibody was added to diluted plasma samples in 96 well polypropylene plate (reaction solution). After incubation, reaction solution was transferred to each well of the streptavidin plate. One of rabbit Anti Fc-Mutation Antibodies (SKA0001) was added followed by the addition of anti-rabbit-HRP (Southern Bio-technology Associates Inc.). Finally, POD substrate was added to each well of the plate and OD was measured. The streptavidin plate was washed between the steps.

Method Evaluation

Reproducibility was tested. Intra-batch accuracy (RE) and precision (CV) were-6.4% to −1.9% and 1.5% to 2.9% respectively (Table 19).

TABLE 19

| Sample name | Spiked concentration (pg/mL) | Converted value (pg/mL) | Mean (pg/mL) | CV (%) | RE (0/0) |
|---|---|---|---|---|---|
| R5 | 100 | 91.6 | 93.6 | 1.5 | −6.4 |
|  |  | 93.7 |  |  |  |
|  |  | 94.5 |  |  |  |
|  |  | 95.0 |  |  |  |
|  |  | 94.5 |  |  |  |
|  |  | 92.2 |  |  |  |
| R4 | 200 | 234 | 225 | 2.1 | — |
|  |  | 223 |  |  |  |
|  |  | 220 |  |  |  |
|  |  | 224 |  |  |  |
|  |  | 224 |  |  |  |
|  |  | 227 |  |  |  |
| R3 | 400 | 420 | 429 | 2.5 | — |
|  |  | 424 |  |  |  |
|  |  | 449 |  |  |  |
|  |  | 424 |  |  |  |
|  |  | 426 |  |  |  |
|  |  | 434 |  |  |  |
| R2 | 2560 | 2460 | 2470 | 1.5 | — |
|  |  | 2490 |  |  |  |
|  |  | 2510 |  |  |  |
|  |  | 2460 |  |  |  |
|  |  | 2510 |  |  |  |
|  |  | 2420 |  |  |  |
| R1 | 3200 | 3120 | 3140 | 2.9 | −1.9 |
|  |  | 3250 |  |  |  |
|  |  | 3170 |  |  |  |
|  |  | 3140 |  |  |  |
|  |  | 3180 |  |  |  |
|  |  | 2980 |  |  |  |

Converted values out of the quantitation range (below 100 pg/mL in plasma, above 3200 pg/mL plasma) were included in the calculation.

The result of intra-day reproducibility was used as the result of inter-day reproducibility 1st Assay.

CV: Coefficient of variation

RE: Relative error

Inter-batch accuracy (RE) and precision (CV) were −8.0% to 2.1% and 3.0% to 5.2% respectively (Table 20).

TABLE 20

| Batch No. | R5 100 Converted value (pg/mL) | R5 Mean (pg/mL) | R5 CV (%) | R5 RE (%) | R4 200 Converted value (pg/mL) | R4 Mean (pg/mL) | R4 CV (%) | R3 400 Converted value (pg/mL) | R3 Mean (pg/mL) | R3 CV (%) | R2 2560 Converted value (pg/mL) | R2 Mean (pg/mL) | R2 CV (%) | R1 3200 Converted value (pg/mL) | R1 Mean (pg/mL) | R1 CV (%) | R1 RE (%) |
|---|---|---|---|---|---|---|---|---|---|---|---|---|---|---|---|---|---|
| 190619 (1st run) | 91.6 | 93.6 | 1.5 | −6.4 | 234 | 225 | 2.1 | 420 | 429 | 2.5 | 2460 | 2470 | 1.5 | 3120 | 3140 | 2.9 | −1.9 |
|  | 93.7 |  |  |  | 223 |  |  | 424 |  |  | 2490 |  |  | 3250 |  |  |  |
|  | 94.5 |  |  |  | 220 |  |  | 449 |  |  | 2510 |  |  | 3170 |  |  |  |
|  | 95.0 |  |  |  | 224 |  |  | 424 |  |  | 2460 |  |  | 3140 |  |  |  |
|  | 94.5 |  |  |  | 224 |  |  | 426 |  |  | 2510 |  |  | 3180 |  |  |  |
|  | 92.2 |  |  |  | 227 |  |  | 434 |  |  | 2420 |  |  | 2980 |  |  |  |

TABLE 20-continued

| | Sample name | | | | | | | | | | | | | | | | | |
| | R5 | | | | R4 | | | R3 | | | R2 | | | R1 | | | |
| | Spiked concentration (pg/mL) | | | | | | | | | | | | | | | | | |
| | 100 | | | | 200 | | | 400 | | | 2560 | | | 3200 | | | |
| Batch No. | Converted value (pg/mL) | Mean (pg/mL) | CV (%) | RE (%) | Converted value (pg/mL) | Mean (pg/mL) | CV (%) | Converted value (pg/mL) | Mean (pg/mL) | CV (%) | Converted value (pg/mL) | Mean (pg/mL) | CV (%) | Converted value (pg/mL) | Mean (pg/mL) | CV (%) | RE (%) |
|---|---|---|---|---|---|---|---|---|---|---|---|---|---|---|---|---|---|
| 190620 (2nd run) | 90.8 | 92.5 | 3.7 | −7.5 | 233 | 235 | 2.1 | 435 | 418 | 3.4 | 2660 | 2610 | 2.6 | 3080 | 3290 | 5.7 | 2.7 |
| | 93.5 | | | | 229 | | | 421 | | | 2650 | | | 3360 | | | |
| | 94.1 | | | | 238 | | | 415 | | | 2620 | | | 3020 | | | |
| | 94.1 | | | | 233 | | | 394 | | | 2580 | | | 3390 | | | |
| | 96.1 | | | | 235 | | | 416 | | | 2660 | | | 3460 | | | |
| | 86.5 | | | | 244 | | | 429 | | | 2480 | | | 3410 | | | |
| 190621 (3rd run) | 87.1 | 89.9 | 2.1 | −10.1 | 237 | 226 | 3.3 | 428 | 414 | 3.6 | 2440 | 2520 | 4.2 | 3140 | 3370 | 4.1 | 5.4 |
| | 91.7 | | | | 224 | | | 411 | | | 2390 | | | 3340 | | | |
| | 88.6 | | | | 225 | | | 406 | | | 2590 | | | 3440 | | | |
| | 90.2 | | | | 231 | | | 391 | | | 2600 | | | 3470 | | | |
| | 89.6 | | | | 216 | | | 416 | | | 2640 | | | 3530 | | | |
| | 92.2 | | | | 224 | | | 432 | | | 2460 | | | 3310 | | | |
| n = 18 | — | 92.0 | 3.0 | −8.0 | — | 229 | 3.1 | — | 421 | 3.4 | — | 2530 | 3.6 | — | 3270 | 5.2 | 2.1 |

Converted values out of the quantitation range (below 100 pg/mL in plasma, above 3200 pg/mL in plasma) were included in the calculation.
The result of intra-day reproducibility was used as the result of inter-day reproducibility 1st Assay.
CV: Coefficient of variation
RE: Relative error Dilution linearity was tested. One microgram per milliliter of IL-8 (spiked) could be measured in dilution factor 20,000-fold and prozone effect was not observed (Table 21).

TABLE 21

Spiked concentration in pooled human plasma: 1000 ng/mL

| Sample name | Dilution factor | Measured value (pg/mL) | Converted value (pg/mL) | Mean (pg/mL) | CV (%) | RE (%) |
|---|---|---|---|---|---|---|
| DL1 | 5 | ALQ | — | — | — | — |
| | | ALQ | — | | | |
| | | ALQ | — | | | |
| DL2 | 400 | ALQ | — | — | — | — |
| | | ALQ | — | | | |
| | | ALQ | — | | | |

TABLE 21-continued

Spiked concentration in pooled human plasma: 1000 ng/mL

| Sample name | Dilution factor | Measured value (pg/mL) | Converted value (pg/mL) | Mean (pg/mL) | CV (%) | RE (%) |
|---|---|---|---|---|---|---|
| DL3 | 2500 | 368 | 921,000 | 954,000 | 3.1 | −4.6 |
| | | 385 | 961,000 | | | |
| | | 391 | 978,000 | | | |
| DL4 | 20,000 | 47.7 | 954,000 | 948,000 | 0.8 | −5.2 |
| | | 47.0 | 939,000 | | | |
| | | 47.6 | 951,000 | | | |

ALQ: Above upper limit of quantitation (>640 pg/mL)
CV: Coefficient of variation
RE: Relative error Interference from Anti-IL-8 Antibody was tested. Interference from Anti-IL-8 Antibody (100 micro-g/mL in plasma) was not observed (Table 22).

TABLE 22

Batch No.190702

| Sample name | IL–8 spiked concentration in plasma (pg/mL) | Anti–IL–8 Antibody spiked concentration in plasma (μg/mL) | Anti Fc–Mutation Antibody spiked concentration in plasma (μg/mL) | Converted value (pg/mL) | % difference |
|---|---|---|---|---|---|
| IS1 | 400 | 100 | 100 | 2040 | 381.6 |
| IS2 | 400 | 100 | 10.0 | 628 | 48.2 |
| IS3 | 400 | 100 | 1.00 | 449 | 5.9 |
| IS4 | 400 | 100 | 0 | 428 | 0.8 |
| IS5 | 400 | 10.0 | 100 | 2990 | 606.4 |
| IS6 | 400 | 10.0 | 10.0 | 632 | 49.1 |
| IS7 | 400 | 10.0 | 1.00 | 452 | 6.6 |
| IS8 | 400 | 10.0 | 0 | 432 | 1.8 |
| IS9 | 400 | 0 | 100 | 2060 | 386.8 |
| IS10 | 400 | 0 | 10.0 | 618 | 45.9 |
| IS11 | 400 | 0 | 1.00 | 449 | 5.8 |
| IS12 | 400 | 0 | 0 | 424 | NA |
| IS13 | 100 | 100 | 100 | 1610 | 1358.5 |
| IS14 | 100 | 100 | 10.0 | 301 | 171.8 |

TABLE 22-continued

| | Batch No.190702 | | | | |
| --- | --- | --- | --- | --- | --- |
| Sample name | IL–8 spiked concentration in plasma (pg/mL) | Anti–IL–8 Antibody spiked concentration in plasma (µg/mL) | Anti Fc–Mutation Antibody spiked concentration in plasma (µg/mL) | Converted value (pg/mL) | % difference |
| IS15 | 100 | 100 | 1.00 | 132 | 19.5 |
| IS16 | 100 | 100 | 0 | 113 | 2.1 |
| IS17 | 100 | 10.0 | 100 | 1840 | 1563.8 |
| IS18 | 100 | 10.0 | 10.0 | 291 | 162.7 |
| IS19 | 100 | 10.0 | 1.00 | 133 | 20.0 |
| IS20 | 100 | 10.0 | 0 | 114 | 3.2 |
| IS21 | 100 | 0 | 100 | 1680 | 1419.5 |
| IS22 | 100 | 0 | 10.0 | 303 | 174.3 |
| IS23 | 100 | 0 | 1.00 | 131 | 18.1 |
| IS24 | 100 | 0 | 0 | 111 | NA |
| IS25 | 0 | 100 | 100 | 1480 | NA |
| IS26 | 0 | 100 | 10.0 | 182 | NA |
| IS27 | 0 | 100 | 1.00 | 21.6 | NA |
| IS28 | 0 | 100 | 0 | 1.63 | NA |
| IS29 | 0 | 10.0 | 100 | 1620 | NA |
| IS30 | 0 | 10.0 | 10.0 | 198 | NA |
| IS31 | 0 | 10.0 | 1.00 | 17.2 | NA |
| IS32 | 0 | 10.0 | 0 | ND | NA |
| IS33 | 0 | 0 | 100 | 1440 | NA |
| IS34 | 0 | 0 | 10.0 | 189 | NA |
| IS35 | 0 | 0 | 1.00 | 18.4 | NA |
| IS36 | 0 | 0 | 0 | ND | NA |

%difference = (converted value of IS added sample-converted value of IS free sample) / converted value of IS free sample × 100
IS: Interference substance
ND: Not detected
Underline: Below lower limit of quantitation (<100 pg/mL in plasma)
NA: Not applicable The effectiveness of the method to measure IL-8 in human plasma using ELISA was confirmed.

Example 8

Evaluation of the Method to Measure IL-8 in Human Plasma Using Simoa (Registered Trademark) (Simoa (Registered Trademark) Assay)
Assay Procedures
Assay was conducted automatically by using Simoa (registered trademark) system (Quanterix Corporation). Diluted samples, Anti-IL-8 Antibody, and mouse anti-IL-8 mono-clonal antibody coated on beads were mixed. The beads were loaded into microwell of an array disk. Biotinylated Anti Fc-Mutation Antibody (SKA0028) was added to the disk followed by the addition of streptavidin-beta-galacto-sidase, SBG (Quanterix Corporation). Finally, substrate of beta-galactocidases, RGB, was added and fluorescent intensity was measured.

Method Evaluation
Reproducibility was tested. Intra-batch precision (CV) were 1.3% to 14.3% (Table 23).

TABLE 23

| Plasma batch No. Run ID | PLA021B020C009 1 | PLA021A020C011 1 | PLA022C100E001 3 | PLA022A100E001 3 | PLA021A050000 1 | B061631P 1 | B061633P 1 |
| --- | --- | --- | --- | --- | --- | --- | --- |
| Measured | 0.0734 | 0.0760 | 0.147 | 0.322 | 1.04 | 2.56 | 3.92 |
| value | 0.102 | 0.0982 | 0.156 | 0.324 | 1.07 | 2.57 | 3.78 |
| (pg/mL) | 0.0910 | 0.0854 | 0.147 | 0.344 | 1.16 | 2.54 | 4.14 |
| | 0.100 | 0.114 | 0.154 | 0.322 | 1.19 | 2.51 | 4.06 |
| | 0.0778 | 0.0864 | 0.143 | 0.270 | 1.13 | 2.53 | 3.97 |
| | 0.0925 | 0.0950 | 0.145 | 0.307 | 1.10 | 2.60 | 4.07 |
| % CV | 13.0 | 14.3 | 3.6 | 7.9 | 4.9 | 1.3 | 3.2 |
| n | 6 | 6 | 6 | 6 | 6 | 6 | 6 |

Inter-batch precision (CV) were 8.6% to 24.7% respectively (Table 24).

TABLE 24-1

| | Run ID | Measured value (pg/mL) | Run ID | Measured value (pg/mL) | Run ID | Measured value (pg/mL) | Run ID | Measured value (pg/mL) |
|---|---|---|---|---|---|---|---|---|
| Plasma batch No. | PLA021B020C009 | | PLA021A020C011 | | PLA022C100E001 | | PLA022A100E001 | |
| | 1 | 0.0734 | 1 | 0.0760 | 3 | 0.147 | 3 | 0.322 |
| | | 0.102 | | 0.0982 | | 0.156 | | 0.324 |
| | | 0.0910 | | 0.0854 | | 0.147 | | 0.344 |
| | 4 | 0.0577 | 4 | 0.0465 | 4 | 0.124 | 4 | 0.232 |
| | | 0.0702 | | 0.0421 | | 0.119 | | 0.251 |
| | | 0.0445 | | 0.0743 | | 0.147 | | 0.264 |
| | 5 | 0.0459 | 6 | 0.0844 | 5 | 0.148 | 5 | 0.315 |
| | | 0.0614 | | 0.0663 | | 0.131 | | 0.285 |
| | | 0.0687 | | 0.0683 | | 0.128 | | 0.283 |
| | 7 | 0.0766 | 7 | 0.0543 | 7 | 0.133 | 7 | 0.305 |
| | | 0.0712 | | 0.0534 | | 0.152 | | 0.317 |
| | | 0.0737 | | 0.0716 | | 0.136 | | 0.353 |
| Mean Measured value (pg/mL) | 0.0697 | | 0.0684 | | 0.139 | | 0.300 | |
| % CV | 23.7 | | 24.7 | | 8.6 | | 12.4 | |
| n | 12 | | 12 | | 12 | | 12 | |
| Dilution factor | 20 | | 20 | | 20 | | 20 | |
| Endogenous IL-8 concentration in plasma (pg/mL) | 1.39 | | 1.37 | | 2.78 | | 5.99 | |

| | Run ID | Measured value | Run ID | Measured value | Run ID | Measured value |
|---|---|---|---|---|---|---|
| Plasma batch No. | PLA021A050000 | | B061631P | | B061633P | |
| | 1 | 1.04 | 1 | 2.56 | 1 | 3.92 |
| | | 1.07 | | 2.57 | | 3.78 |
| | | 1.16 | | 2.54 | | 4.14 |
| | 4 | 0.933 | 4 | 2.13 | 4 | 3.59 |
| | | 0.943 | | 2.26 | | 3.35 |
| | | 1.00 | | 2.01 | | 3.46 |
| | 5 | 0.878 | 5 | 1.95 | 5 | 3.09 |
| | | 0.909 | | 1.95 | | 3.17 |
| | | 0.862 | | 1.94 | | 3.33 |
| | 7 | 1.00 | 7 | 2.19 | 7 | 3.54 |
| | | 1.06 | | 2.16 | | 3.41 |
| | | 0.99 | | 2.11 | | 2.95 |
| Mean Measured value (pg/mL) | 0.986 | | 2.20 | | 3.48 | |
| % CV | 8.8 | | 11.0 | | 9.9 | |
| n | 12 | | 12 | | 12 | |
| Dilution factor | 20 | | 20 | | 20 | |
| Endogenous IL-8 concentration in plasma (pg/mL) | 19.7 | | 44.0 | | 69.6 | |

Parallelism was tested. Three individual plasmas were serially diluted from 20-fold to 40-fold and measured. In any dilution factors, measured concentrations were recovered (Table 25).

TABLE 25

| Plasma batch No. | Measured value (pg/mL) | Dilution factor | Endogenous IL-8 concentration in plasma (pg/mL) | % Diff |
|---|---|---|---|---|
| PLA021A010BB228 | 0.423 | 20 | 8.46 | 0.0 |
| | 0.285 | 30 | 8.56 | 1.2 |
| | 0.203 | 40 | 8.11 | -4.2 |
| PLA021A010D012 | 0.757 | 20 | 15.1 | 0.0 |
| | 0.543 | 30 | 16.3 | 7.8 |
| | 0.432 | 40 | 17.3 | 14.2 |

TABLE 25-continued

| Plasma batch No. | Measured value (pg/mL) | Dilution factor | Endogenous IL-8 concentration in plasma (pg/mL) | % Diff |
|---|---|---|---|---|
| PLA021A050000 | 0.332 | 20 | 6.64 | 0.0 |
| | 0.215 | 30 | 6.46 | -2.8 |
| | 0.202 | 40 | 8.06 | 21.4 |

Dilution linearity was tested. Three point four eight microgram per milliliter of IL-8 could be measured in dilution factor 50,000-fold and prozone effect was not observed. (Table 26).

TABLE 26

| Sample name | Measured value (pg/mL) | Dilution factor | IL-8 concentration in plasma (pg/mL) | Mean IL-8 concentration in plasma (pg/mL) | Theoretical concentration (pg/mL) | % RE | % CV |
|---|---|---|---|---|---|---|---|
| DIL-50 | ALQ | 50 | — | — | — | — | — |
|  | ALQ |  | — |  |  |  |  |
|  | ALQ |  | — |  |  |  |  |
| DIL-25,000 | 3.92 | 25,000 | 97,963.49 | 97444.76 | 100,005.99* | −2.6 | 0.9 |
|  | 3.86 |  | 96,424.67 |  |  |  |  |
|  | 3.92 |  | 97,946.10 |  |  |  |  |
| DIL-50,000 | 1.89 | 50,000 | 94,466.88 | 98160.95 |  | −1.8 | 3.8 |
|  | 1.96 |  | 98,008.77 |  |  |  |  |
|  | 2.04 |  | 10,2007.21 |  |  |  |  |

—: Not applicable

*: Theoretical concentration was calculated considering concentration of the endogenous IL-8 in the plasma (batch No. PLA022A100E001) determined in between-run precision.

Interference from Anti-IL-8 Antibody was tested. Interference from Anti-IL-8 Antibody (100 micro-g/mL in plasma) was not observed (Table 27).

TABLE 27

| Sample name | Anti-IL-8 Antibody conc. in plasma (μg/mL) | Measured value (pg/mL) | Dilution factor | Endogenous IL-8 concentration in plasma (pg/mL) | % Int |
|---|---|---|---|---|---|
| INT0 | 0 | 0.358 | 20 | 7.17 | 0.0 |
| INT1 | 1.00 | 0.353 |  | 7.06 | −1.6 |
| INT2 | 10.0 | 0.359 |  | 7.19 | 0.3 |
| INT3 | 30.0 | 0.371 |  | 7.42 | 3.4 |
| INT4 | 60.0 | 0.364 |  | 7.28 | 1.5 |
| INT5 | 100 | 0.368 |  | 7.36 | 2.7 |

The effectiveness of the method to measure IL-8 in human plasma using Simoa (registered trademark) assay was confirmed.

Example 9

Evaluation of Affinity of Anti Fc-Mutation Antibodies that Show Selective Binding to SG115v1 Against Anti-hC5 Antibody.

$K_D$ value of Anti Fc-Mutation Antibodies that show selective binding to SG115v1 (SKA0009, SKA0016, SKA0046, SKA0052, SKA0054, and SKA0127) against Anti-hC5 Antibody at pH 7.4 was determined at 25 degrees C. using Biacore T200 instrument (GE Healthcare).

Mouse anti-rabbit IgG (Fc) antibody (hereinafter called anti-rabbit IgG) (Abbexa) was immobilized onto flow cell (FC) 1 and 2 of a CM5 sensor chip using an amine coupling kit (GE Healthcare). For the immobilization of anti-rabbit IgG, HBS-EP+, pH7.4 (GE Healthcare) buffer was used as running buffer. After the immobilization, running buffer was changed to phosphate pH7.4 buffer (50 mM phosphate buffer containing 150 mM NaCl and 0.05 w/v % P-20, pH 7.4). Each Anti Fc-Mutation Antibody was captured onto FC2 of the sensor chip by anti-rabbit IgG. The amount of Anti Fc-Mutation Antibody to be captured was adjusted so that the number of resonance units (RU) was 100. Anti-hC5 Antibody was injected at 0, 50, 100, 200, 400, and 800 nM at 10 micro L/min. Sensor surface was regenerated after each cycle with 10 mM Glycine-HCl, pH2.0, which was injected at a flow rate of 30 micro L/min. $K_D$ values were obtained using Biacore T200 Evaluation software, version 2.0 (GE Healthcare). Association rate (ka), dissociation rate (kd), and dissociation constant ($K_D$) are shown in Table 28.

TABLE 28

| Ligand | ka (1/Ms) | kd (1/s) | $K_D$ (M) |
|---|---|---|---|
| SKA0009 | $7.69 \times 10^4$ | $*1.41 \times 10^{-6}$ | $*1.84 \times 10^{-11}$ |
| SKA0016 | $3.09 \times 10^4$ | $*5.90 \times 10^{-7}$ | $*1.91 \times 10^{-11}$ |
| SKA0046 | $8.85 \times 10^4$ | $5.17 \times 10^{-5}$ | $*5.85 \times 10^{-10}$ |
| SKA0052 | $1.08 \times 10^5$ | $1.96 \times 10^{-4}$ | $1.81 \times 10^{-9}$ |
| SKA0054 | $2.73 \times 10^4$ | $1.97 \times 10^{-4}$ | $7.22 \times 10^{-9}$ |
| SKA0127 | $7.18 \times 10^4$ | $2.54 \times 10^{-4}$ | $3.54 \times 10^{-9}$ |

*: the data reliability might be low due to slow dissociation rate

Example 10

Evaluation of Affinity of Anti Fc-Mutation Antibodies that Show Selective Binding to SG115v1 Against Anti-IL-8 Antibody.

To confirm the binding ability of Anti Fc-Mutation Antibodies that show selective binding to SG115v1, $K_D$ values of Anti Fc-Mutation Antibodies against Anti-IL-8 Antibody at pH 7.4 were determined at 25 degrees C. using Biacore T200 instrument (GE Healthcare). Sequence of Fc region of Anti-IL-8 Antibody has high similarity to that of Anti-hC5 Antibody.

Anti-rabbit IgG (Abbexa) was immobilized onto FC1 and 2 of a CM5 sensor chip using an amine coupling kit (GE Healthcare). For the immobilization of anti-rabbit IgG, HBS-EP+, pH7.4 (GE Healthcare) buffer was used as running buffer. After the immobilization, running buffer was changed to Phosphate pH7.4 buffer (50 mM phosphate buffer containing 150 mM NaCl and 0.05 w/v % P-20, pH 7.4). Each Anti Fc-Mutation Antibody was captured onto FC2 of the sensor chip by anti-rabbit IgG. The amount of Anti Fc-Mutation Antibody to be captured was adjusted so that the number of resonance units (RU) was 100. Anti-IL-8 Antibody was injected at 0, 100, 400, and 800 nM at 10 micro L/min. Sensor surface was regenerated after each cycle with 10 mM Glycine-HCl, pH2.0, which was injected at a flow rate of 30 micro L/min. $K_D$ values were obtained using Biacore T200 Evaluation software, version 2.0 (GE Healthcare).

ka, kd, and $K_D$ are listed in Table 29. While the amino acid at position 239 according to the EU numbering system in Anti-hC5 Antibody was mutated from Ser to Lys, the amino acid at the corresponding position in Anti-IL-8 Antibody was not mutated. In such situation, Anti Fc-Mutation Antibodies could bind to Anti-IL-8 Antibody. It means that the two mutations in SG115v1 which both Anti-hC5 Antibody and Anti-IL-8 Antibody commonly have, i.e. L235R and G236R (both positions are according to the EU numbering system), are essential for selective binding of Anti Fc-Mutation Antibodies to SG115v1.

TABLE 29

| Ligand | ka (1/Ms) | kd (1/s) | KD (M) |
|---|---|---|---|
| SKA0009 | $2.50 \times 10^4$ | $9.04 \times 10^{-4}$ | $3.62 \times 10^{-8}$ |
| SKA0016 | $1.18 \times 10^4$ | $7.10 \times 10^{-4}$ | $6.00 \times 10^{-8}$ |
| SKA0046 | $4.20 \times 10^4$ | $2.09 \times 10^{-3}$ | $4.96 \times 10^{-8}$ |
| SKA0052 | $9.17 \times 10^4$ | $4.31 \times 10^{-3}$ | $4.70 \times 10^{-8}$ |
| SKA0054 | $9.98 \times 10^3$ | $9.66 \times 10^{-4}$ | $9.68 \times 10^{-8}$ |
| SKA0127 | $1.77 \times 10^4$ | $8.04 \times 10^{-4}$ | $4.54 \times 10^{-8}$ |

*: the data reliability might be low due to slow dissociation rate

Example 11

Evaluation of Affinity of Anti Fc-Mutation Antibodies that Show Selective Binding to SG115v2 Against Anti-DENV E Protein Antibody $K_D$ value of Anti Fc-Mutation Antibodies that show selective binding to SG115v2 (SKA0001, SKA0027, SKA0028, SKA0117, SKA0141, and SKA0171) against an anti-DENV E protein antibody comprising a modified IgG heavy chain constant region (SEQ ID NO: 116) as Fc-Mutated Antibody at pH 7.4 was determined at 25 degrees C. using Biacore T200 instrument (GE Healthcare). Anti-rabbit IgG was immobilized onto FC 3 and 4 of a CM5 sensor chip using an amine coupling kit (GE Healthcare). For the immobilization of anti-rabbit IgG, HBS-EP+, pH7.4 (GE Healthcare) buffer was used as running buffer. After the immobilization, running buffer was changed to phosphate pH7.4 buffer. Each antibody was captured onto FC4 of the sensor chip by anti-rabbit IgG. The amount of Anti Fc-Mutation Antibody to be captured was adjusted so that the number of resonance units (RU) was 100. The anti-DENV E protein antibody was injected at 0, 12.5, 50, and 400 nM at 10 micro L/min. Sensor surface was regenerated each cycle with 10 mM Glycine-HCl, pH2.0, which was injected at a flow rate of 30 micro L/min. $K_D$ values were obtained using Biacore T200 Evaluation software, version 2.0 (GE Healthcare). ka, kd, and $K_D$ are shown in Table 30.

TABLE 30

| Ligand | ka (1/Ms) | kd (1/s) | $K_D$ (M) |
|---|---|---|---|
| SKA0001 | $4.44 \times 10^4$ | *$1.23 \times 10^{-7}$ | *$2.78 \times 10^{-12}$ |
| SKA0027 | $1.90 \times 10^5$ | $1.91 \times 10^{-4}$ | $1.00 \times 10^{-9}$ |
| SKA0028 | $1.16 \times 10^5$ | $7.27 \times 10^{-5}$ | *$6.26 \times 10^{-10}$ |
| SKA0117 | $1.26 \times 10^5$ | *$3.46 \times 10^{-8}$ | *$2.75 \times 10^{-13}$ |

TABLE 30-continued

| Ligand | ka (1/Ms) | kd (1/s) | $K_D$ (M) |
|---|---|---|---|
| SKA0141 | $2.67 \times 10^5$ | $1.35 \times 10^{-3}$ | $5.04 \times 10^{-9}$ |
| SKA0171 | $1.02 \times 10^6$ | $1.49 \times 10^{-3}$ | $1.45 \times 10^{-9}$ |

*: the data reliability might be low due to slow dissociation rate

Example 12

Evaluation of Affinity of Anti-hC5 Antibody Against Human C5 Using SKA0016 and SKA0117 as Capture Molecules.

$K_D$ value of Anti-hC5 Antibody against human C5 at pH 7.4 was determined at 37 degrees C. using Biacore T200 instrument (GE Healthcare). SKA0016 was immobilized onto FC1 and 2, and SKA0117 was immobilized onto FC3 and 4 of a CM5 sensor chip using an amine coupling kit (GE Healthcare). For the immobilization of SKA0016 and SKA0117, HBS-EP+, pH7.4 (GE Healthcare) buffer was used as running buffer. After the immobilization, running buffer was changed to phosphate pH7.4 buffer. Anti-hC5 Antibody was captured onto FC2 and FC4 of the sensor chip by SKA0016 and SKA0117. The amount of Anti-hC5 antibody to be captured was adjusted so that the number of resonance units (RU) was 35. Human C5 was injected at 0, 2, 4, 8, 16, and 32 nM at 10 micro L/min. Sensor surface was regenerated each cycle with 100 mM Glycine-HCl, pH2.0 followed by 25 mM NaOH, which were both injected at a flow rate of 30 micro L/min. $K_D$ values were obtained using Biacore T200 Evaluation software, version 2.0 (GE Healthcare). ka, kd, and $K_D$ are listed in Table 31.

TABLE 31

| Capture molecule | ka (1/Ms) | k(1/s) | $K_D$ (M) |
|---|---|---|---|
| SKA0016 | $6.33 \times 10^5$ | $1.13 \times 10^{-4}$ | $1.78 \times 10^{-10}$ |
| SKA0117 | $6.51 \times 10^5$ | $1.23 \times 10^{-4}$ | $1.88 \times 10^{-10}$ |

Example 13

Qualitative Analysis of pH-Dependent Interaction of Anti-hC5 Antibody Against Human C5 Using SKA0016 and SKA0117 as Immobilizing Molecules.

pH-dependent interaction between Anti-hC5 Antibody and human C5 at pH7.4 and pH6.0 was evaluated at 37 degrees C. using Biacore T200 instrument (GE Healthcare). Anti-hC5 Antibody was captured onto FC2 and FC4 of CM5 chip that was prepared in EXAMPLE 12. The amount of Anti-hC5 antibody to be captured was adjusted so that the number of resonance units (RU) was 35. To confirm the association between Anti-hC5 Antibody and human C5 at pH7.4, 32 nM of human C5 was injected to all FC in phosphate pH 7.4 buffer. Then dissociation phase was monitored in phosphate pH 7.4 buffer or phosphate pH6.0 buffer (50 mM phosphate buffer containing 150 mM NaCl and 0.05 w/v % P-20, pH 6.0) as running buffer. After monitoring the dissociation phase, the sensor chip was regenerated by injecting 100 mM Gly-HCl, pH2.0 followed by 25 mM NaOH, which were both injected at a flow rate of 30 micro L/min. The pH-dependent interaction of Anti-hC5 Antibody to human C5 was analyzed by comparing the dissociation phases of sensorgrams at pH 7.4 and pH 6.0 using Biacore T200 Evaluation Software Version 2.0. Sensorgram on FC2 was subtracted by FC1 and sensorgram of FC4 was subtracted by FC3, and each sensorgram was normalized by adjusting human C5 binding response, which was at 5 seconds before the end of human C5 injection, to the value '100'.

Figure 6:
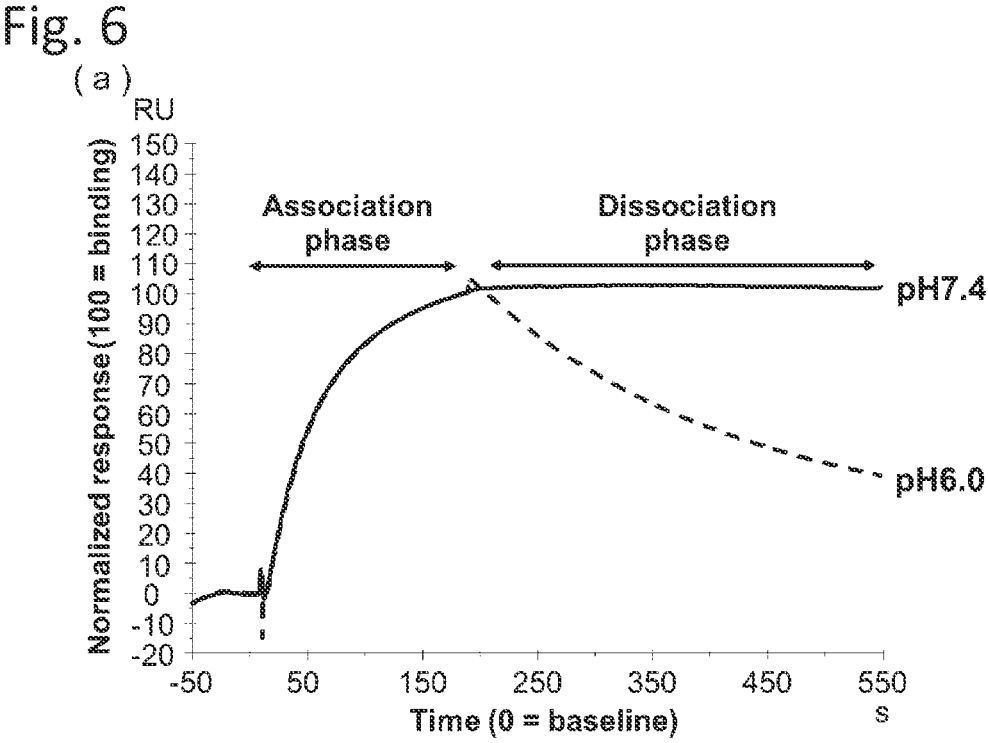
FIG. 6 illustrates the sensorgram of dissociation of human C5 from Anti-hC5 Antibody that was captured by SKA0016 and SKA0117 at pH7.4 and pH6.0. Both SKA0016 and SKA0117 did not disturb the pH-dependent interaction between Anti-hC5 Antibody and human C5.
Figure 6:
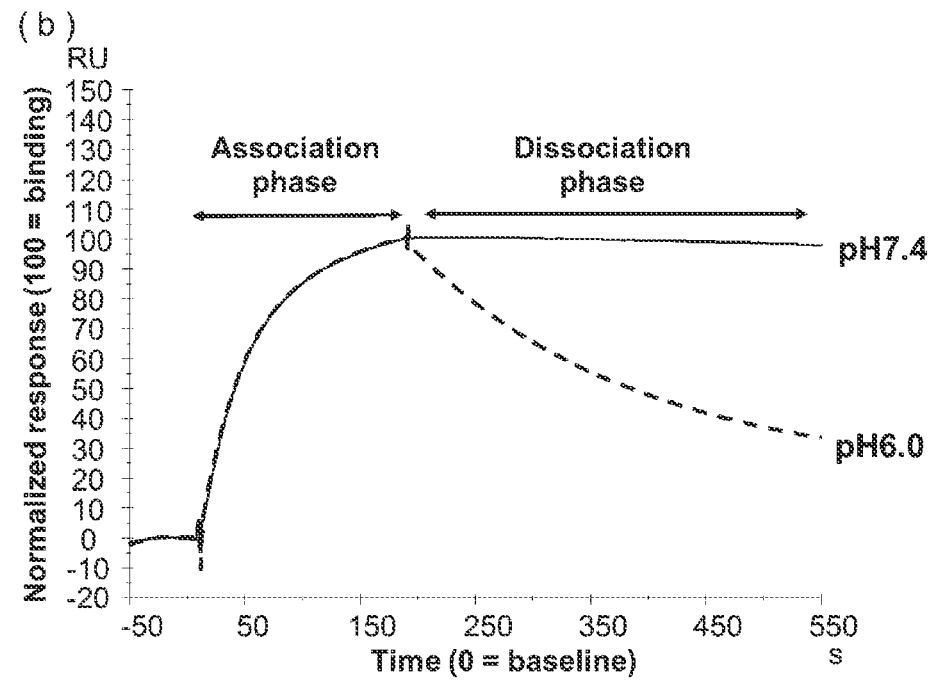

Regardless of the capture molecule, dissociation of human C5 from Anti-hC5 Antibody was more rapid on the condition with pH6.0 than with pH7.4 (FIG. 6; Anti-hC5 Antibody was immobilized by (a) SKA0016 and (b) SKA0117). Therefore, it is considered that both SKA0016 and SKA0117 are effective for monitoring pH-dependent interaction between Anti-hC5 Antibody and human C5.

Example 14

Evaluation of Binding Between Human Fc Receptor (hFcRn) and Anti-hC5 Antibody that was Captured by SKA0016.

Whether human FcRn could bind to Anti-hC5 Antibody that was captured by SKA0016 at pH 6.0 was evaluated using Biacore T200 instrument (GE Healthcare). Anti-hC5 Antibody was captured onto FC2 by SKA0016 that was immobilized to CM5 chip by the same procedure as in EXAMPLE 9. Phosphate pH6.0 buffer was used as running buffer. The amount of Anti-hC5 antibody to be captured was adjusted so that the number of resonance units (RU) was 400. hFcRn was injected at 0, 26.3, 52.5, 105, 210, and 420 nM at 10 micro L/min in single cycle kinetics manner. Sensor surface was regenerated with 100 mM Glycine-HCl, pH2.0 followed by 25 mM NaOH, which were both injected at a flow rate of 30 micro L/min. Increment of binding response of hFcRn was confirmed using Biacore T200 Evaluation software, version 2.0 (GE Healthcare).

Figure 7:
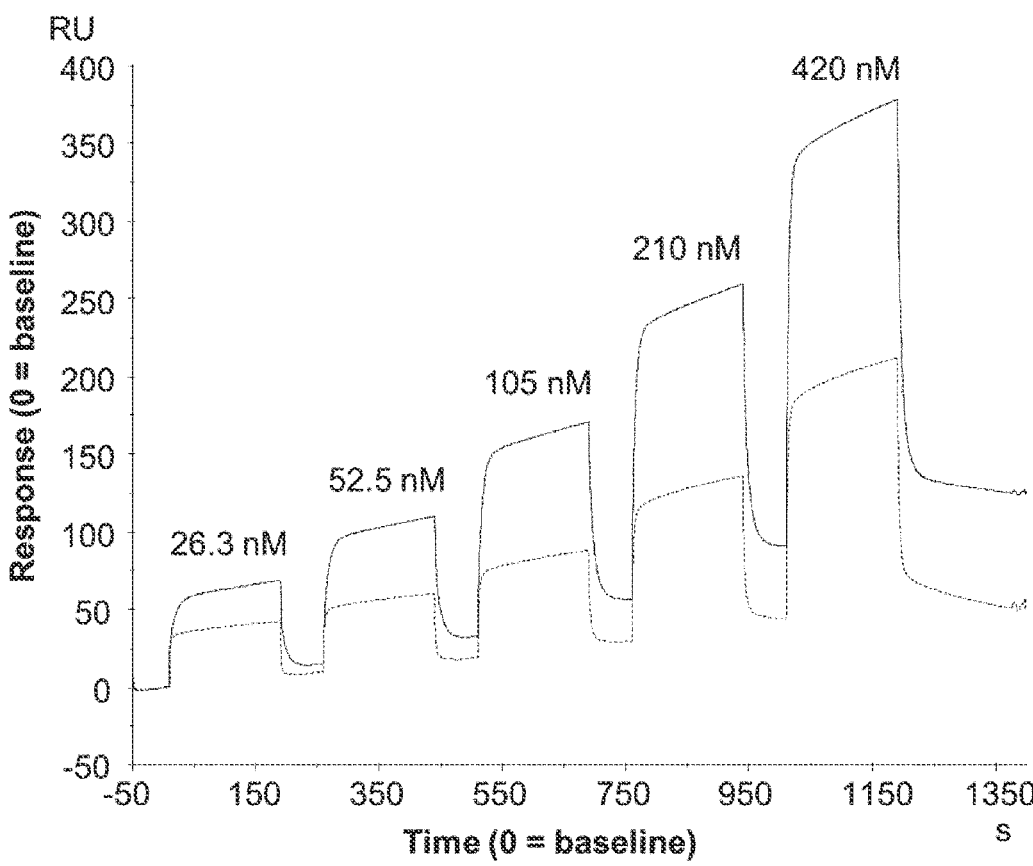
FIG. 7 illustrates the sensorgram of binding analysis of human Fc receptor to Anti-hC5 Antibody that was captured by SKA0016. SKA0016 did not interrupt the binding between hFcRn and Anti-hC5 Antibody.

FIG. 7 shows sensorgram of FC1 (dash line) and FC2 (solid line). From the FC2 sensorgram (solid line), it is recognized that the binding response of hFcRn increases concentration-dependent manner. SKA0016 did not interrupt the binding between hFcRn and Anti-hC5 Antibody. However, hFcRn seems to bind to Fc region of SKA0016 because the sensorgram of FC1 also showed the increment of binding response (dash line). This undesirable human FcRn binding to capture molecule can be solved by introducing the amino acid substitutions which abrogate the binding to human FcRn into SKA0016.

Sequence Listing

---

The invention claimed is:

1. An isolated antibody which specifically binds to a modified human IgG heavy chain constant region, wherein the antibody comprises any one of following (a) to (f):

(a) variable regions that comprise

HVR-H1 comprising the amino acid sequence of SEQ ID NO: 32,

HVR-H2 comprising the amino acid sequence of SEQ ID NO: 44,

HVR-H3 comprising the amino acid sequence of SEQ ID NO: 56,

HVR-L1 comprising the amino acid sequence of SEQ ID NO: 68,

HVR-L2 comprising the amino acid sequence of SEQ ID NO: 80, and

HVR-L3 comprising the amino acid sequence of SEQ ID NO: 92;

(b) variable region that comprise

HVR-H1 comprising the amino acid sequence of SEQ ID NO: 35,

HVR-H2 comprising the amino acid sequence of SEQ ID NO: 47,

HVR-H3 comprising the amino acid sequence of SEQ ID NO: 59,

HVR-L1 comprising the amino acid sequence of SEQ ID NO: 71,

HVR-L2 comprising the amino acid sequence of SEQ ID NO: 83, and

HVR-L3 comprising the amino acid sequence of SEQ ID NO: 95;

(c) variable region that comprise

HVR-H1 comprising the amino acid sequence of SEQ ID NO: 36,

HVR-H2 comprising the amino acid sequence of SEQ ID NO: 48,

HVR-H3 comprising the amino acid sequence of SEQ ID NO: 60,

HVR-L1 comprising the amino acid sequence of SEQ ID NO: 72,

HVR-L2 comprising the amino acid sequence of SEQ ID NO: 84, and

HVR-L3 comprising the amino acid sequence of SEQ ID NO: 96;

(d) variable region that comprise

HVR-H1 comprising the amino acid sequence of SEQ ID NO: 40,

HVR-H2 comprising the amino acid sequence of SEQ ID NO: 52,

HVR-H3 comprising the amino acid sequence of SEQ ID NO: 64,

HVR-L1 comprising the amino acid sequence of SEQ ID NO: 76,

HVR-L2 comprising the amino acid sequence of SEQ ID NO: 88, and

HVR-L3 comprising the amino acid sequence of SEQ ID NO: 100;

(e) variable region that comprise

HVR-H1 comprising the amino acid sequence of SEQ ID NO: 42,

HVR-H2 comprising the amino acid sequence of SEQ ID NO: 54,

HVR-H3 comprising the amino acid sequence of SEQ ID NO: 66,

HVR-L1 comprising the amino acid sequence of SEQ ID NO: 78,

HVR-L2 comprising the amino acid sequence of SEQ ID NO: 90, and

HVR-L3 comprising the amino acid sequence of SEQ ID NO: 102; and (f) variable region that comprise HVR-H1 comprising the amino acid sequence of SEQ ID NO: 43, HVR-H2 comprising the amino acid sequence of SEQ ID NO: 55, HVR-H3 comprising the amino acid sequence of SEQ ID NO: 67, HVR-L1 comprising the amino acid sequence of SEQ ID NO: 79, HVR-L2 comprising the amino acid sequence of SEQ ID NO: 91, and HVR-L3 comprising the amino acid sequence of SEQ ID NO: 103.

2. The antibody of claim 1, wherein the modified IgG heavy chain constant region is modified from an IgG1 constant region comprising the amino acid sequence of SEQ ID NO: 106, an IgG2 constant region comprising the amino acid sequence of SEQ ID NO: 107, an IgG3 constant region comprising the amino acid sequence of SEQ ID NO: 108, or an IgG4 constant region comprising the amino acid sequence of SEQ ID NO: 109.

3. The antibody of claim 1, wherein said modified IgG heavy chain constant region is derived from a chimeric constant region obtained from constant regions in human naturally occurring IgG1 and IgG4.

4. The antibody of claim 1, which binds to the modified IgG heavy chain constant region consisting of the amino acid sequence LHEALHAHYTRKE (SEQ ID NO: 105).

5. An isolated nucleic acid encoding the antibody of claim 1.

6. A host cell comprising a vector comprising the nucleic acid of claim 5.

7. A method of making an antibody wherein the method comprises culturing the host cell of claim 6 under conditions suitable for expression of the antibody, and optionally recovering the antibody from the host cell or host cell culture medium.

8. The antibody of claim 1, wherein the modified IgG heavy chain constant region comprises at least one amino acid selected from Arg at position 235, Arg at position 236, and Lys at position 239 (all positions according to the EU numbering system).

9. The antibody of claim 1, wherein the modified IgG heavy chain constant region comprises Arg at position 235, and either or both of Arg at position 236 and Lys at position 239 (all positions according to the EU numbering system).

* * * * *

SEQUENCE LISTING

<160> NUMBER OF SEQ ID NOS: 120

<210> SEQ ID NO 1
<211> LENGTH: 328
<212> TYPE: PRT
<213> ORGANISM: Artificial Sequence
<220> FEATURE:
<223> OTHER INFORMATION: SG115

<400> SEQUENCE: 1

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Arg Gly Pro Lys Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

-continued

```
Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ala His Tyr Thr
305                 310                 315                 320

Arg Lys Glu Leu Ser Leu Ser Pro
                325
```

```
<210> SEQ ID NO 2
<211> LENGTH: 328
<212> TYPE: PRT
<213> ORGANISM: Artificial Sequence
<220> FEATURE:
<223> OTHER INFORMATION: SG115v1

<400> SEQUENCE: 2
```

```
Ala Ser Thr Lys Gly Pro Ser Val Phe Pro Leu Ala Pro Ser Ser Lys
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Arg Arg Gly Pro Lys Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240
```

```
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 3
<211> LENGTH: 328
<212> TYPE: PRT
<213> ORGANISM: Artificial Sequence
<220> FEATURE:
<223> OTHER INFORMATION: SG115v2

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

-continued

```
Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Leu His Glu Ala Leu His Ala His Tyr Thr
305                 310                 315                 320

Arg Lys Glu Leu Ser Leu Ser Pro
                325

<210> SEQ ID NO 4
<211> LENGTH: 328
<212> TYPE: PRT
<213> ORGANISM: Artificial Sequence
<220> FEATURE:
<223> OTHER INFORMATION: G1m

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
        20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
        100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300
```

-continued

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 5
<211> LENGTH: 325
<212> TYPE: PRT
<213> ORGANISM: Artificial Sequence
<220> FEATURE:
<223> OTHER INFORMATION: G4d

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
                325

<210> SEQ ID NO 6
<211> LENGTH: 323
<212> TYPE: PRT
<213> ORGANISM: Artificial Sequence
<220> FEATURE:
<223> OTHER INFORMATION: rbIgGv2

<400> SEQUENCE: 6

```
Gly Gln Pro Lys Ala Pro Ser Val Phe Pro Leu Ala Pro Cys Cys Gly
1               5                   10                  15

Asp Thr Pro Ser Ser Thr Val Thr Leu Gly Cys Leu Val Lys Gly Tyr
                20                  25                  30

Leu Pro Glu Pro Val Thr Val Thr Trp Asn Ser Gly Thr Leu Thr Asn
            35                  40                  45

Gly Val Arg Thr Phe Pro Ser Val Arg Gln Ser Ser Gly Leu Tyr Ser
        50                  55                  60

Leu Ser Ser Val Val Ser Val Thr Ser Ser Ser Gln Pro Val Thr Cys
65                  70                  75                  80

Asn Val Ala His Pro Ala Thr Asn Thr Lys Val Asp Lys Thr Val Ala
                85                  90                  95

Pro Ser Thr Cys Ser Lys Pro Thr Cys Pro Pro Pro Glu Leu Leu Gly
            100                 105                 110

Gly Pro Ser Val Phe Ile Phe Pro Pro Lys Pro Lys Asp Thr Leu Met
            115                 120                 125

Ile Ser Arg Thr Pro Glu Val Thr Cys Val Val Val Asp Val Ser Gln
        130                 135                 140

Asp Asp Pro Glu Val Gln Phe Thr Trp Tyr Ile Asn Asn Glu Gln Val
145                 150                 155                 160

Arg Thr Ala Arg Pro Pro Leu Arg Glu Gln Gln Phe Asn Ser Thr Ile
                165                 170                 175

Arg Val Val Ser Thr Leu Pro Ile Thr His Gln Asp Trp Leu Arg Gly
                180                 185                 190

Lys Glu Phe Lys Cys Lys Val His Asn Lys Ala Leu Pro Ala Pro Ile
            195                 200                 205

Glu Lys Thr Ile Ser Lys Ala Arg Gly Gln Pro Leu Glu Pro Lys Val
            210                 215                 220

Tyr Thr Met Gly Pro Pro Arg Glu Glu Leu Ser Ser Arg Ser Val Ser
225                 230                 235                 240

Leu Thr Cys Met Ile Asn Gly Phe Tyr Pro Ser Asp Ile Ser Val Glu
                245                 250                 255

Trp Glu Lys Asn Gly Lys Ala Glu Asp Asn Tyr Lys Thr Thr Pro Ala
                260                 265                 270

Val Leu Asp Ser Asp Gly Ser Tyr Phe Leu Tyr Asn Lys Leu Ser Val
                275                 280                 285

Pro Thr Ser Glu Trp Gln Arg Gly Asp Val Phe Thr Cys Ser Val Met
            290                 295                 300

His Glu Ala Leu His Asn His Tyr Thr Gln Lys Ser Ile Ser Arg Ser
305                 310                 315                 320

Pro Gly Lys
```

<210> SEQ ID NO 7
<211> LENGTH: 104
<212> TYPE: PRT
<213> ORGANISM: Artificial Sequence
<220> FEATURE:
<223> OTHER INFORMATION: rbIgk

<400> SEQUENCE: 7

Gly Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
            35                  40                  45

Thr Gly Ile Glu Asn Ser Lys Thr Pro Gln Asn Ser Ala Asp Cys Thr
        50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
                100

<210> SEQ ID NO 8
<211> LENGTH: 114
<212> TYPE: PRT
<213> ORGANISM: Artificial Sequence
<220> FEATURE:
<223> OTHER INFORMATION: SKA0001-VH

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Tyr Tyr Ala
            20                  25                  30

Met Asn Trp Val Arg Gln Ala Pro Gly Lys Gly Leu Glu Trp Ile Gly
        35                  40                  45

Ile Ile Gly Ile Ser Gly Gly Thr Tyr Tyr Ala Ser Trp Ala Lys Gly
        50                  55                  60

Arg Phe Thr Ile Ser Lys Ser Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Ser Ala Trp Gly Asp Leu Trp Gly Gln Gly Thr Leu Val Thr Val
            100                 105                 110

Ser Ser

<210> SEQ ID NO 9
<211> LENGTH: 115
<212> TYPE: PRT
<213> ORGANISM: Artificial Sequence
<220> FEATURE:
<223> OTHER INFORMATION: SKA0009-VH

<400> SEQUENCE: 9

Gln Ser Val Glu Glu Ser Gly Gly Arg Leu Val Thr Pro Gly Thr Ser
1               5                   10                  15

Leu Thr Leu Thr Cys Thr Val Ser Gly Ile Asp Leu Ser Ser Tyr Gly
            20                  25                  30

Met Gly Trp Val Arg Gln Ala Pro Gly Met Gly Leu Glu Tyr Ile Gly
        35                  40                  45

Ile Ile Tyr Ala Ala Gly Arg Thr Tyr Tyr Ala Ser Trp Val Lys Gly
        50                  55                  60

```
Arg Phe Ile Ile Ser Lys Thr Ser Thr Thr Val Asp Leu Glu Met Thr
65                  70                  75                  80

Ser Leu Thr Thr Glu Asp Thr Ala Thr Tyr Phe Cys Ala Arg His Gly
                85                  90                  95

Ser Trp Tyr Ala Gly Met Asp Leu Trp Gly Pro Gly Thr Leu Val Thr
                100                 105                 110

Val Ser Ser
        115

<210> SEQ ID NO 10
<211> LENGTH: 124
<212> TYPE: PRT
<213> ORGANISM: Artificial Sequence
<220> FEATURE:
<223> OTHER INFORMATION: SKA0016-VH

<400> SEQUENCE: 10

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
                20                  25                  30

Asp Tyr Met Cys Trp Val Arg Gln Ala Pro Gly Lys Gly Leu Glu Trp
        35                  40                  45

Ile Ala Cys Ile Tyr Ile Gly Ser Asn Gly Asp Thr Phe Tyr Ala Ser
        50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Asp Ser Arg Arg Ala Asp Asp Tyr Gly Thr Arg Leu Asp
                100                 105                 110

Leu Trp Gly Gln Gly Thr Leu Val Thr Val Ser Ser
        115                 120

<210> SEQ ID NO 11
<211> LENGTH: 121
<212> TYPE: PRT
<213> ORGANISM: Artificial Sequence
<220> FEATURE:
<223> OTHER INFORMATION: SKA0027-VH

<400> SEQUENCE: 11

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
                20                  25                  30

Asp Tyr Met Cys Trp Val Arg Gln Ala Pro Gly Lys Gly Leu Glu Trp
        35                  40                  45

Ile Gly Cys Ile Tyr Thr Gly Ser Gly Ser Thr Tyr Tyr Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Phe Phe Cys
                85                  90                  95

Ala Arg Arg Gly Asp Ser Tyr Ser Asn Tyr Ser Phe Lys Leu Trp Gly
                100                 105                 110

Pro Gly Thr Leu Val Thr Val Ser Ser
        115                 120
```

-continued

```
<210> SEQ ID NO 12
<211> LENGTH: 119
<212> TYPE: PRT
<213> ORGANISM: Artificial Sequence
<220> FEATURE:
<223> OTHER INFORMATION: SKA0028-VH

<400> SEQUENCE: 12

Gln Ser Val Glu Glu Ser Gly Gly Arg Leu Val Thr Pro Gly Thr Pro
1               5                   10                  15

Leu Thr Leu Thr Cys Thr Ala Ser Gly Phe Thr Ile Ser Ser Tyr His
            20                  25                  30

Met Ser Trp Val Arg Gln Ala Pro Gly Lys Gly Leu Glu Trp Ile Gly
        35                  40                  45

Ile Ile His Gly Ser Gly Asn Met Trp Tyr Ala Ser Trp Ala Lys Gly
    50                  55                  60

Arg Phe Thr Ile Ser Arg Thr Ser Thr Thr Val Asp Leu Glu Ile Thr
65                  70                  75                  80

Ser Pro Thr Thr Glu Asp Thr Ala Thr Tyr Phe Cys Ala Arg Ile Arg
                85                  90                  95

Phe Trp Ala Ser Ser Asn Tyr Tyr Tyr Phe Tyr Leu Trp Gly Gln Gly
            100                 105                 110

Thr Leu Val Thr Val Ser Ser
        115

<210> SEQ ID NO 13
<211> LENGTH: 128
<212> TYPE: PRT
<213> ORGANISM: Artificial Sequence
<220> FEATURE:
<223> OTHER INFORMATION: SKA0046-VH

<400> SEQUENCE: 13

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Leu Ser Ser Ser
            20                  25                  30

Asn Tyr Met Trp Trp Val Arg Gln Ala Pro Gly Lys Gly Leu Glu Trp
        35                  40                  45

Ile Ala Cys Ile His Ala Ser Ser Ser Gly Asp Thr Tyr Tyr Ala Asn
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Gly Gly Tyr Ile Tyr Gly Asp Gly Gly Tyr Asn Gly Val
            100                 105                 110

Ala Gly Phe Ser Leu Trp Gly Pro Gly Thr Leu Val Thr Val Ser Ser
        115                 120                 125

<210> SEQ ID NO 14
<211> LENGTH: 123
<212> TYPE: PRT
<213> ORGANISM: Artificial Sequence
<220> FEATURE:
<223> OTHER INFORMATION: SKA0052-VH

<400> SEQUENCE: 14
```

```
Gln Ser Leu Glu Glu Ser Gly Gly Asp Leu Val Lys Ser Gly Ala Ser
1               5                   10                  15

Leu Thr Leu Thr Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Thr Gly Ser Asn Gly Asp Thr Tyr Tyr Ala Ser Trp
        50                  55                  60

Ala Asn Gly Arg Phe Thr Ile Ser Lys Ala Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Tyr Thr Tyr Asp Asp Asp Gly Asp Tyr Thr Ser Phe Asn Leu
            100                 105                 110

Trp Gly Pro Gly Thr Leu Val Thr Val Ser Ser
        115                 120

<210> SEQ ID NO 15
<211> LENGTH: 127
<212> TYPE: PRT
<213> ORGANISM: Artificial Sequence
<220> FEATURE:
<223> OTHER INFORMATION: SKA0054-VH

<400> SEQUENCE: 15

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Ser Ser Phe
            20                  25                  30

Trp Ile Cys Trp Val Arg Gln Ala Pro Gly Lys Gly Leu Glu Trp Leu
        35                  40                  45

Ala Cys Ile Asp Ala Gly Ser Ser Asp Asn Thr Tyr Tyr Ala Asn Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Asp Ala Asp Thr Ala Thr Tyr Phe Cys
                85                  90                  95

Ala Arg Asp Arg Asp Ala Ala Gly Asp Ala Gly Tyr Gly Tyr Ala Thr
            100                 105                 110

Ser Phe Asn Leu Trp Gly Pro Gly Thr Leu Val Thr Val Ser Ser
        115                 120                 125

<210> SEQ ID NO 16
<211> LENGTH: 126
<212> TYPE: PRT
<213> ORGANISM: Artificial Sequence
<220> FEATURE:
<223> OTHER INFORMATION: SKA0117-VH

<400> SEQUENCE: 16

Gln Ser Leu Glu Glu Ser Gly Gly Asp Leu Val Lys Pro Glu Gly Ser
1               5                   10                  15

Leu Thr Leu Thr Cys Thr Ala Ser Gly Phe Ser Phe Ser Ser Ser His
            20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Asp Asn Thr Tyr Tyr Ala Ser Trp
        50                  55                  60
```

```
Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Thr Tyr Gly Tyr Val Gly Tyr Ala Ser Ala Gly Gly Phe
            100                 105                 110

Phe Asn Leu Trp Gly Pro Gly Thr Leu Val Thr Val Ser Ser
        115                 120                 125

<210> SEQ ID NO 17
<211> LENGTH: 114
<212> TYPE: PRT
<213> ORGANISM: Artificial Sequence
<220> FEATURE:
<223> OTHER INFORMATION: SKA0127-VH

<400> SEQUENCE: 17

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Thr Tyr Ala
                20                  25                  30

Met Thr Trp Val Arg Gln Ala Pro Gly Lys Gly Leu Glu Tyr Ile Gly
            35                  40                  45

Tyr Ile Asn Gly Gly Gly Ser Ala Tyr Tyr Ala Ser Trp Val Asn Gly
        50                  55                  60

Arg Phe Thr Ile Ser Lys Thr Ser Thr Thr Ala Asp Leu Lys Ile Thr
65                  70                  75                  80

Ser Pro Thr Thr Glu Asp Thr Ala Thr Tyr Phe Cys Ala Arg Gly Pro
                85                  90                  95

Val Gly Ser Tyr His Arg Ile Trp Gly Pro Gly Thr Leu Val Thr Val
            100                 105                 110

Ser Ser

<210> SEQ ID NO 18
<211> LENGTH: 123
<212> TYPE: PRT
<213> ORGANISM: Artificial Sequence
<220> FEATURE:
<223> OTHER INFORMATION: SKA0141-VH

<400> SEQUENCE: 18

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Ser Ser Tyr
                20                  25                  30

Tyr Met Cys Trp Val Arg Gln Ala Pro Gly Lys Gly Leu Glu Trp Ile
            35                  40                  45

Ala Cys Ile Tyr Ala Gly Ser Ser Gly Ser Thr Tyr Tyr Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Asp Gly Asp Glu Asn Met Leu Val Gly Gly Tyr Phe Asn Leu
            100                 105                 110

Trp Gly Pro Gly Thr Leu Val Thr Val Ser Ser
        115                 120
```

```
<210> SEQ ID NO 19
<211> LENGTH: 125
<212> TYPE: PRT
<213> ORGANISM: Artificial Sequence
<220> FEATURE:
<223> OTHER INFORMATION: SKA0171-VH

<400> SEQUENCE: 19

Gln Ser Leu Glu Glu Ser Gly Gly Gly Leu Val Gln Pro Glu Gly Ser
1               5                   10                  15

Leu Thr Leu Ser Cys Thr Ala Ser Gly Phe Ser Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Gly Gly Asn Ser Val Ile Thr Tyr Tyr Ala Asn Trp
    50                  55                  60

Ala Lys Gly Arg Phe Thr Ile Ser Glu Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Glu Val His Tyr Asp Tyr Leu Tyr Thr Thr Tyr Gly Tyr Ala
            100                 105                 110

Asn Leu Trp Gly Pro Gly Thr Leu Val Thr Val Ser Ser
        115                 120                 125

<210> SEQ ID NO 20
<211> LENGTH: 112
<212> TYPE: PRT
<213> ORGANISM: Artificial Sequence
<220> FEATURE:
<223> OTHER INFORMATION: SKA0001-VL

<400> SEQUENCE: 20

Asp Ile Val Met Thr Gln Thr Pro Ser Ser Val Ser Ala Ala Val Gly
1               5                   10                  15

Gly Thr Val Thr Ile Asn Cys Gln Ala Ser Gln Ser Ile Ser Arg Leu
            20                  25                  30

Leu Ala Trp Tyr Gln Gln Lys Pro Gly Gln Pro Pro Lys Val Leu Met
        35                  40                  45

His Asp Ala Ser Asp Leu Ala Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Ser Tyr Tyr Trp Gly Ser Ser
                85                  90                  95

Gly Asp Ile Gly Tyr Pro Phe Gly Gly Gly Thr Glu Val Val Val Lys
            100                 105                 110

<210> SEQ ID NO 21
<211> LENGTH: 110
<212> TYPE: PRT
<213> ORGANISM: Artificial Sequence
<220> FEATURE:
<223> OTHER INFORMATION: SKA0009-VL

<400> SEQUENCE: 21

Ala Ile Glu Met Thr Gln Thr Pro Ser Pro Val Ser Ala Ala Val Gly
1               5                   10                  15
```

-continued

```
Gly Thr Val Ser Ile Asn Cys Gln Ala Ser Glu Asp Ile Glu Asn Tyr
            20                  25                  30

Phe Ala Trp Tyr Gln Gln Lys Pro Gly Gln Pro Pro Lys Leu Leu Ile
            35                  40                  45

Tyr Asp Ala Ser Glu Leu Ala Ser Gly Val Pro Ser Arg Phe Ser Gly
    50                  55                  60

Ser Gly Ser Gly Thr Asp Phe Thr Leu Thr Ile Ser Gly Val Gln Cys
65                  70                  75                  80

Asp Asp Ala Ala Thr Tyr Tyr Cys Gln His Ala Asp Tyr Ala Ala Ser
                85                  90                  95

Ser Glu Asn Thr Phe Gly Gly Gly Thr Glu Val Val Val Lys
            100                 105                 110
```

<210> SEQ ID NO 22
<211> LENGTH: 114
<212> TYPE: PRT
<213> ORGANISM: Artificial Sequence
<220> FEATURE:
<223> OTHER INFORMATION: SKA0016-VL

<400> SEQUENCE: 22

```
Ala Asp Ile Val Met Thr Gln Thr Pro Ser Ser Val Ser Ala Ala Val
1               5                   10                  15

Gly Gly Thr Val Thr Ile Lys Cys Gln Ala Ser Gln Asn Ile Tyr Arg
            20                  25                  30

Asn Leu Ala Trp Tyr Gln Gln Lys Pro Gly Gln Pro Pro Lys Leu Leu
            35                  40                  45

Ile Tyr Gln Ala Ser Lys Leu Glu Ser Gly Val Pro Ser Arg Phe Lys
    50                  55                  60

Gly Ser Gly Ser Gly Thr Glu Phe Thr Leu Thr Ile Ser Asp Leu Asp
65                  70                  75                  80

Cys Asp Asp Ala Ala Ser Tyr Tyr Cys Gln Ser Ile Ser Tyr Ile Ser
                85                  90                  95

Ser Gly Asp Thr Phe Phe Trp Ala Phe Gly Gly Gly Thr Glu Val Val
            100                 105                 110

Val Lys
```

<210> SEQ ID NO 23
<211> LENGTH: 110
<212> TYPE: PRT
<213> ORGANISM: Artificial Sequence
<220> FEATURE:
<223> OTHER INFORMATION: SKA0027-VL

<400> SEQUENCE: 23

```
Ala Phe Glu Leu Thr Gln Thr Pro Ala Ser Val Glu Ala Ala Val Gly
1               5                   10                  15

Gly Thr Val Thr Ile Lys Cys Gln Ala Ser Gln Asn Ile Tyr Ser Asn
            20                  25                  30

Leu Ala Trp Tyr Gln Gln Lys Pro Gly Gln Pro Pro Lys Leu Leu Ile
            35                  40                  45

Tyr Thr Ala Ser Ser Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Cys Thr Tyr Ile Asn Asn Gly
                85                  90                  95
```

-continued

```
Tyr Gly Asn Thr Phe Gly Gly Gly Thr Glu Val Val Val Lys
            100             105             110

<210> SEQ ID NO 24
<211> LENGTH: 110
<212> TYPE: PRT
<213> ORGANISM: Artificial Sequence
<220> FEATURE:
<223> OTHER INFORMATION: SKA0028-VL

<400> SEQUENCE: 24

Ala Leu Val Met Thr Gln Thr Pro Ala Ser Val Ser Glu Pro Val Gly
1               5                   10                  15

Gly Thr Val Thr Ile Asn Cys Gln Ala Ser Gln Asn Ile Tyr Ser Asn
            20                  25                  30

Leu Ala Trp Tyr Gln Gln Lys Pro Gly Gln Arg Pro Arg Leu Leu Ile
        35                  40                  45

Tyr Gly Ala Ser Asn Leu Glu Ser Gly Val Pro Ser Arg Phe Arg Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Ala Tyr Trp Gly Asn Asn
                85                  90                  95

Asn Asp Gly Ala Phe Gly Gly Gly Thr Glu Val Val Val Lys
            100             105             110

<210> SEQ ID NO 25
<211> LENGTH: 113
<212> TYPE: PRT
<213> ORGANISM: Artificial Sequence
<220> FEATURE:
<223> OTHER INFORMATION: SKA0046-VL

<400> SEQUENCE: 25

Asp Val Val Met Thr Gln Thr Pro Ala Ser Val Ser Glu Pro Val Gly
1               5                   10                  15

Gly Thr Val Thr Ile Lys Cys Gln Ala Ser Glu Thr Ile Gly Asn Ala
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Glu Phe Thr Leu Thr Ile Ser Asp Val Gln Cys
65                  70                  75                  80

Asp Asp Ala Ala Thr Tyr Tyr Cys Gln Ser Ile Tyr Tyr Ser Ser Ser
                85                  90                  95

Ala Asp Thr Phe Phe Phe Pro Phe Gly Gly Gly Thr Glu Val Val Val
            100             105             110

Lys

<210> SEQ ID NO 26
<211> LENGTH: 113
<212> TYPE: PRT
<213> ORGANISM: Artificial Sequence
<220> FEATURE:
<223> OTHER INFORMATION: SKA0052-VL

<400> SEQUENCE: 26

Ala Leu Val Met Thr Gln Thr Pro Ser Ser Val Ser Ala Asp Val Gly
1               5                   10                  15
```

-continued

```
Gly Thr Val Thr Ile Asn Cys Gln Ala Ser Gln Asn Ile Tyr Arg Asn
            20                  25                  30

Leu Ala Trp Tyr Gln Gln Lys Pro Gly Gln Arg Pro Lys Leu Leu Ile
            35                  40                  45

Tyr Gly Ala Ser Asn Leu Glu Pro Gly Val Pro Ser Arg Phe Lys Gly
        50                  55                  60

Ser Gly Ser Gly Thr Glu Phe Thr Leu Thr Ile Ser Asp Leu Glu Cys
65                  70                  75                  80

Asp Asp Ala Ala Thr Tyr Tyr Cys Gln Ser Val Gly Tyr Ser Gly Ser
                85                  90                  95

Val Asp Thr Phe Phe Tyr Ala Phe Gly Gly Gly Thr Glu Val Val Val
            100                 105                 110

Lys
```

<210> SEQ ID NO 27
<211> LENGTH: 113
<212> TYPE: PRT
<213> ORGANISM: Artificial Sequence
<220> FEATURE:
<223> OTHER INFORMATION: SKA0054-VL

<400> SEQUENCE: 27

```
Ala Ile Asp Met Thr Gln Thr Pro Ser Ser Val Ser Ala Ala Val Gly
1               5                   10                  15

Gly Thr Val Thr Ile Asn Cys Gln Ala Ser Glu Ser Ile Tyr Ser Asn
            20                  25                  30

Leu Ala Trp Tyr Gln Gln Lys Pro Gly Gln Arg Pro Lys Leu Leu Ile
            35                  40                  45

Tyr Leu Ala Ser Thr Leu Ala Ser Gly Val Pro Ser Arg Phe Lys Gly
        50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Ser Val Tyr Tyr Asp Ser Arg
                85                  90                  95

Gly Asp Thr Phe Phe Trp Ala Phe Gly Gly Gly Thr Glu Val Val Val
            100                 105                 110

Lys
```

<210> SEQ ID NO 28
<211> LENGTH: 111
<212> TYPE: PRT
<213> ORGANISM: Artificial Sequence
<220> FEATURE:
<223> OTHER INFORMATION: SKA0117-VL

<400> SEQUENCE: 28

```
Ala Leu Val Met Thr Gln Thr Pro Ala Ser Val Ser Ala Ala Val Gly
1               5                   10                  15

Gly Thr Val Thr Ile Asn Cys Gln Ala Ser His Asn Ile Tyr Ser Val
            20                  25                  30

Leu Ala Trp Tyr Gln Gln Lys Pro Gly Gln Arg Pro Arg Leu Leu Ile
            35                  40                  45

Tyr Gly Ala Ser Asn Leu Glu Ser Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80
```

```
Asp Asp Ala Ala Thr Tyr Tyr Cys Gln Ser Ala Tyr Tyr Ser Ser Ser
            85                  90                  95

Thr Gly Asp Asn Ala Phe Gly Gly Gly Thr Glu Val Val Val Lys
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: SKA0127-VL

<400> SEQUENCE: 29

Ala Leu Val Met Thr Gln Thr Pro Ser Ser Val Ser Glu Pro Val Gly
1               5                   10                  15

Gly Thr Val Thr Ile Asn Cys Arg Ala Ser Glu Asp Ile Glu Ser Tyr
            20                  25                  30

Leu Ala Trp Tyr Gln Gln Lys Pro Gly Gln Pro Pro Lys Leu Leu Ile
        35                  40                  45

Tyr Ala Thr Ser Asn Leu Glu Thr Gly Val Pro Ser Arg Phe Lys Gly
        50                  55                  60

Ser Gly Ser Gly Thr Asp Tyr Thr Leu Thr Ile Ser Gly Val Gln Cys
65                  70                  75                  80

Ala Asp Ala Ala Thr Tyr Tyr Cys Gln Gly Tyr Tyr Glu Leu Ser Ser
            85                  90                  95

Ile Asp Asn Asn Ala Phe Gly Gly Gly Thr Glu Val Val Val Lys
            100                 105                 110

<210> SEQ ID NO 30
<211> LENGTH: 111
<212> TYPE: PRT
<213> ORGANISM: Artificial Sequence
<220> FEATURE:
<223> OTHER INFORMATION: SKA0141-VL

<400> SEQUENCE: 30

Ala Leu Val Met Thr Gln Thr Pro Ser Ser Val Ser Ala Ala Val Gly
1               5                   10                  15

Gly Thr Val Thr Ile Asn Cys Gln Ala Ser His Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
        50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Ala Tyr Tyr Ser Ser Asn
            85                  90                  95

Ala Gly Tyr Asn Ala Phe Gly Gly Gly Thr Glu Val Val Val Lys
            100                 105                 110

<210> SEQ ID NO 31
<211> LENGTH: 111
<212> TYPE: PRT
<213> ORGANISM: Artificial Sequence
<220> FEATURE:
<223> OTHER INFORMATION: SKA0171-VL

<400> SEQUENCE: 31

Ala Ile Lys Met Thr Gln Thr Pro Ala Ser Val Ser Ala Val Val Gly
```

-continued

```
1               5               10              15

Gly Thr Val Thr Ile Asn Cys Gln Ala Ser Glu Thr Ile Tyr Ser Gly
            20              25              30

Leu Ala Trp Tyr Gln Gln Lys Pro Gly Gln Pro Pro Lys Leu Leu Ile
        35              40              45

Tyr Asp Thr Ala Asn Leu Glu Thr Gly Val Ser Ser Arg Phe Lys Gly
    50              55              60

Ser Gly Ser Gly Thr Glu Tyr Thr Leu Thr Ile Ser Asp Leu Glu Cys
65              70              75              80

Asp Asp Ala Ala Thr Tyr Phe Cys Leu Tyr Ala Tyr Tyr Ser Gly Gly
                85              90              95

Ser Ala Asp Asn Ala Phe Gly Gly Gly Thr Glu Val Val Val Lys
            100             105             110

<210> SEQ ID NO 32
<211> LENGTH: 5
<212> TYPE: PRT
<213> ORGANISM: Artificial Sequence
<220> FEATURE:
<223> OTHER INFORMATION: SKA0001-HCDR1

<400> SEQUENCE: 32

Tyr Tyr Ala Met Asn
1               5

<210> SEQ ID NO 33
<211> LENGTH: 5
<212> TYPE: PRT
<213> ORGANISM: Artificial Sequence
<220> FEATURE:
<223> OTHER INFORMATION: SKA0009-HCDR1

<400> SEQUENCE: 33

Ser Tyr Gly Met Gly
1               5

<210> SEQ ID NO 34
<211> LENGTH: 6
<212> TYPE: PRT
<213> ORGANISM: Artificial Sequence
<220> FEATURE:
<223> OTHER INFORMATION: SKA0016-HCDR1

<400> SEQUENCE: 34

Ser Ser Asp Tyr Met Cys
1               5

<210> SEQ ID NO 35
<211> LENGTH: 6
<212> TYPE: PRT
<213> ORGANISM: Artificial Sequence
<220> FEATURE:
<223> OTHER INFORMATION: SKA0027-HCDR1

<400> SEQUENCE: 35

Ser Ser Asp Tyr Met Cys
1               5

<210> SEQ ID NO 36
<211> LENGTH: 5
<212> TYPE: PRT
<213> ORGANISM: Artificial Sequence
<220> FEATURE:
<223> OTHER INFORMATION: SKA0028-HCDR1
```

<400> SEQUENCE: 36

Ser Tyr His Met Ser
1               5

<210> SEQ ID NO 37
<211> LENGTH: 6
<212> TYPE: PRT
<213> ORGANISM: Artificial Sequence
<220> FEATURE:
<223> OTHER INFORMATION: SKA0046-HCDR1

<400> SEQUENCE: 37

Ser Ser Asn Tyr Met Trp
1               5

<210> SEQ ID NO 38
<211> LENGTH: 6
<212> TYPE: PRT
<213> ORGANISM: Artificial Sequence
<220> FEATURE:
<223> OTHER INFORMATION: SKA0052-HCDR1

<400> SEQUENCE: 38

Ser Ser Tyr Tyr Met Cys
1               5

<210> SEQ ID NO 39
<211> LENGTH: 6
<212> TYPE: PRT
<213> ORGANISM: Artificial Sequence
<220> FEATURE:
<223> OTHER INFORMATION: SKA0054-HCDR1

<400> SEQUENCE: 39

Ser Ser Phe Trp Ile Cys
1               5

<210> SEQ ID NO 40
<211> LENGTH: 6
<212> TYPE: PRT
<213> ORGANISM: Artificial Sequence
<220> FEATURE:
<223> OTHER INFORMATION: SKA0117-HCDR1

<400> SEQUENCE: 40

Ser Ser His Tyr Met Cys
1               5

<210> SEQ ID NO 41
<211> LENGTH: 5
<212> TYPE: PRT
<213> ORGANISM: Artificial Sequence
<220> FEATURE:
<223> OTHER INFORMATION: SKA0127-HCDR1

<400> SEQUENCE: 41

Thr Tyr Ala Met Thr
1               5

<210> SEQ ID NO 42
<211> LENGTH: 6
<212> TYPE: PRT
<213> ORGANISM: Artificial Sequence
<220> FEATURE:
<223> OTHER INFORMATION: SKA0141-HCDR1

```
<400> SEQUENCE: 42

Ser Ser Tyr Tyr Met Cys
1               5

<210> SEQ ID NO 43
<211> LENGTH: 6
<212> TYPE: PRT
<213> ORGANISM: Artificial Sequence
<220> FEATURE:
<223> OTHER INFORMATION: SKA0171-HCDR1

<400> SEQUENCE: 43

Ser Ser Tyr Tyr Met Cys
1               5

<210> SEQ ID NO 44
<211> LENGTH: 16
<212> TYPE: PRT
<213> ORGANISM: Artificial Sequence
<220> FEATURE:
<223> OTHER INFORMATION: SKA0001-HCDR2

<400> SEQUENCE: 44

Ile Ile Gly Ile Ser Gly Gly Thr Tyr Tyr Ala Ser Trp Ala Lys Gly
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: SKA0009-HCDR2

<400> SEQUENCE: 45

Ile Ile Tyr Ala Ala Gly Arg Thr Tyr Tyr Ala Ser Trp Val Lys Gly
1               5                   10                  15

<210> SEQ ID NO 46
<211> LENGTH: 18
<212> TYPE: PRT
<213> ORGANISM: Artificial Sequence
<220> FEATURE:
<223> OTHER INFORMATION: SKA0016-HCDR2

<400> SEQUENCE: 46

Cys Ile Tyr Ile Gly Ser Asn Gly Asp Thr Phe Tyr Ala Ser Trp Ala
1               5                   10                  15

Lys Gly

<210> SEQ ID NO 47
<211> LENGTH: 17
<212> TYPE: PRT
<213> ORGANISM: Artificial Sequence
<220> FEATURE:
<223> OTHER INFORMATION: SKA0027-HCDR2

<400> SEQUENCE: 47

Cys Ile Tyr Thr Gly Ser Gly Ser Thr Tyr Tyr Ala Ser Trp Ala Lys
1               5                   10                  15

Gly

<210> SEQ ID NO 48
<211> LENGTH: 16
<212> TYPE: PRT
<213> ORGANISM: Artificial Sequence
```

```
<220> FEATURE:
<223> OTHER INFORMATION: SKA0028-HCDR2

<400> SEQUENCE: 48

Ile Ile His Gly Ser Gly Asn Met Trp Tyr Ala Ser Trp Ala Lys Gly
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: SKA0046-HCDR2

<400> SEQUENCE: 49

Cys Ile His Ala Ser Ser Ser Gly Asp Thr Tyr Tyr Ala Asn Trp Ala
1               5                   10                  15

Lys Gly

<210> SEQ ID NO 50
<211> LENGTH: 18
<212> TYPE: PRT
<213> ORGANISM: Artificial Sequence
<220> FEATURE:
<223> OTHER INFORMATION: SKA0052-HCDR2

<400> SEQUENCE: 50

Cys Ile Tyr Thr Gly Ser Asn Gly Asp Thr Tyr Tyr Ala Ser Trp Ala
1               5                   10                  15

Asn Gly

<210> SEQ ID NO 51
<211> LENGTH: 18
<212> TYPE: PRT
<213> ORGANISM: Artificial Sequence
<220> FEATURE:
<223> OTHER INFORMATION: SKA0054-HCDR2

<400> SEQUENCE: 51

Cys Ile Asp Ala Gly Ser Ser Asp Asn Thr Tyr Tyr Ala Asn Trp Ala
1               5                   10                  15

Lys Gly

<210> SEQ ID NO 52
<211> LENGTH: 18
<212> TYPE: PRT
<213> ORGANISM: Artificial Sequence
<220> FEATURE:
<223> OTHER INFORMATION: SKA0117-HCDR2

<400> SEQUENCE: 52

Cys Ile Tyr Ala Gly Ser Ser Asp Asn Thr Tyr Tyr Ala Ser Trp Ala
1               5                   10                  15

Lys Gly

<210> SEQ ID NO 53
<211> LENGTH: 16
<212> TYPE: PRT
<213> ORGANISM: Artificial Sequence
<220> FEATURE:
<223> OTHER INFORMATION: SKA0127-HCDR2

<400> SEQUENCE: 53

Tyr Ile Asn Gly Gly Gly Ser Ala Tyr Tyr Ala Ser Trp Val Asn Gly
```

-continued

```
1               5               10              15

<210> SEQ ID NO 54
<211> LENGTH: 18
<212> TYPE: PRT
<213> ORGANISM: Artificial Sequence
<220> FEATURE:
<223> OTHER INFORMATION: SKA0141-HCDR2

<400> SEQUENCE: 54

Cys Ile Tyr Ala Gly Ser Ser Gly Ser Thr Tyr Tyr Ala Ser Trp Ala
1               5               10              15

Lys Gly

<210> SEQ ID NO 55
<211> LENGTH: 18
<212> TYPE: PRT
<213> ORGANISM: Artificial Sequence
<220> FEATURE:
<223> OTHER INFORMATION: SKA0171-HCDR2

<400> SEQUENCE: 55

Cys Ile Tyr Gly Gly Asn Ser Val Ile Thr Tyr Tyr Ala Asn Trp Ala
1               5               10              15

Lys Gly

<210> SEQ ID NO 56
<211> LENGTH: 8
<212> TYPE: PRT
<213> ORGANISM: Artificial Sequence
<220> FEATURE:
<223> OTHER INFORMATION: SKA0001-HCDR3

<400> SEQUENCE: 56

Gly Gly Ser Ala Trp Gly Asp Leu
1               5

<210> SEQ ID NO 57
<211> LENGTH: 10
<212> TYPE: PRT
<213> ORGANISM: Artificial Sequence
<220> FEATURE:
<223> OTHER INFORMATION: SKA0009-HCDR3

<400> SEQUENCE: 57

His Gly Ser Trp Tyr Ala Gly Met Asp Leu
1               5               10

<210> SEQ ID NO 58
<211> LENGTH: 14
<212> TYPE: PRT
<213> ORGANISM: Artificial Sequence
<220> FEATURE:
<223> OTHER INFORMATION: SKA0016-HCDR3

<400> SEQUENCE: 58

Asp Ser Arg Arg Ala Asp Asp Tyr Gly Thr Arg Leu Asp Leu
1               5               10

<210> SEQ ID NO 59
<211> LENGTH: 12
<212> TYPE: PRT
<213> ORGANISM: Artificial Sequence
<220> FEATURE:
<223> OTHER INFORMATION: SKA0027-HCDR3
```

<400> SEQUENCE: 59

Arg Gly Asp Ser Tyr Ser Asn Tyr Ser Phe Lys Leu
1               5                   10

<210> SEQ ID NO 60
<211> LENGTH: 14
<212> TYPE: PRT
<213> ORGANISM: Artificial Sequence
<220> FEATURE:
<223> OTHER INFORMATION: SKA0028-HCDR3

<400> SEQUENCE: 60

Ile Arg Phe Trp Ala Ser Ser Asn Tyr Tyr Tyr Phe Tyr Leu
1               5                   10

<210> SEQ ID NO 61
<211> LENGTH: 18
<212> TYPE: PRT
<213> ORGANISM: Artificial Sequence
<220> FEATURE:
<223> OTHER INFORMATION: SKA0046-HCDR3

<400> SEQUENCE: 61

Gly Gly Tyr Ile Tyr Gly Asp Gly Gly Tyr Asn Gly Val Ala Gly Phe
1               5                   10                  15

Ser Leu

<210> SEQ ID NO 62
<211> LENGTH: 14
<212> TYPE: PRT
<213> ORGANISM: Artificial Sequence
<220> FEATURE:
<223> OTHER INFORMATION: SKA0052-HCDR3

<400> SEQUENCE: 62

Tyr Thr Tyr Asp Asp Asp Gly Asp Tyr Thr Ser Phe Asn Leu
1               5                   10

<210> SEQ ID NO 63
<211> LENGTH: 18
<212> TYPE: PRT
<213> ORGANISM: Artificial Sequence
<220> FEATURE:
<223> OTHER INFORMATION: SKA0054-HCDR3

<400> SEQUENCE: 63

Asp Arg Asp Ala Ala Gly Asp Ala Gly Tyr Gly Tyr Ala Thr Ser Phe
1               5                   10                  15

Asn Leu

<210> SEQ ID NO 64
<211> LENGTH: 17
<212> TYPE: PRT
<213> ORGANISM: Artificial Sequence
<220> FEATURE:
<223> OTHER INFORMATION: SKA0117-HCDR3

<400> SEQUENCE: 64

Asp Thr Tyr Gly Tyr Val Gly Tyr Ala Ser Ala Gly Gly Phe Phe Asn
1               5                   10                  15

Leu

<210> SEQ ID NO 65
<211> LENGTH: 9

```
<212> TYPE: PRT
<213> ORGANISM: Artificial Sequence
<220> FEATURE:
<223> OTHER INFORMATION: SKA0127-HCDR3

<400> SEQUENCE: 65

Gly Pro Val Gly Ser Tyr His Arg Ile
1               5

<210> SEQ ID NO 66
<211> LENGTH: 14
<212> TYPE: PRT
<213> ORGANISM: Artificial Sequence
<220> FEATURE:
<223> OTHER INFORMATION: SKA0141-HCDR3

<400> SEQUENCE: 66

Asp Gly Asp Glu Asn Met Leu Val Gly Gly Tyr Phe Asn Leu
1               5                   10

<210> SEQ ID NO 67
<211> LENGTH: 16
<212> TYPE: PRT
<213> ORGANISM: Artificial Sequence
<220> FEATURE:
<223> OTHER INFORMATION: SKA0171-HCDR3

<400> SEQUENCE: 67

Glu Val His Tyr Asp Tyr Leu Tyr Thr Thr Tyr Gly Tyr Ala Asn Leu
1               5                   10                  15

<210> SEQ ID NO 68
<211> LENGTH: 11
<212> TYPE: PRT
<213> ORGANISM: Artificial Sequence
<220> FEATURE:
<223> OTHER INFORMATION: SKA0001-LCDR1

<400> SEQUENCE: 68

Gln Ala Ser Gln Ser Ile Ser Arg Leu Leu Ala
1               5                   10

<210> SEQ ID NO 69
<211> LENGTH: 11
<212> TYPE: PRT
<213> ORGANISM: Artificial Sequence
<220> FEATURE:
<223> OTHER INFORMATION: SKA0009-LCDR1

<400> SEQUENCE: 69

Gln Ala Ser Glu Asp Ile Glu Asn Tyr Phe Ala
1               5                   10

<210> SEQ ID NO 70
<211> LENGTH: 11
<212> TYPE: PRT
<213> ORGANISM: Artificial Sequence
<220> FEATURE:
<223> OTHER INFORMATION: SKA0016-LCDR1

<400> SEQUENCE: 70

Gln Ala Ser Gln Asn Ile Tyr Arg Asn Leu Ala
1               5                   10

<210> SEQ ID NO 71
<211> LENGTH: 11
<212> TYPE: PRT
```

<213> ORGANISM: Artificial Sequence
<220> FEATURE:
<223> OTHER INFORMATION: SKA0027-LCDR1

<400> SEQUENCE: 71

Gln Ala Ser Gln Asn Ile Tyr Ser Asn Leu Ala
1               5                   10

<210> SEQ ID NO 72
<211> LENGTH: 11
<212> TYPE: PRT
<213> ORGANISM: Artificial Sequence
<220> FEATURE:
<223> OTHER INFORMATION: SKA0028-LCDR1

<400> SEQUENCE: 72

Gln Ala Ser Gln Asn Ile Tyr Ser Asn Leu Ala
1               5                   10

<210> SEQ ID NO 73
<211> LENGTH: 11
<212> TYPE: PRT
<213> ORGANISM: Artificial Sequence
<220> FEATURE:
<223> OTHER INFORMATION: SKA0046-LCDR1

<400> SEQUENCE: 73

Gln Ala Ser Glu Thr Ile Gly Asn Ala Leu Ala
1               5                   10

<210> SEQ ID NO 74
<211> LENGTH: 11
<212> TYPE: PRT
<213> ORGANISM: Artificial Sequence
<220> FEATURE:
<223> OTHER INFORMATION: SKA0052-LCDR1

<400> SEQUENCE: 74

Gln Ala Ser Gln Asn Ile Tyr Arg Asn Leu Ala
1               5                   10

<210> SEQ ID NO 75
<211> LENGTH: 11
<212> TYPE: PRT
<213> ORGANISM: Artificial Sequence
<220> FEATURE:
<223> OTHER INFORMATION: SKA0054-LCDR1

<400> SEQUENCE: 75

Gln Ala Ser Glu Ser Ile Tyr Ser Asn Leu Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: SKA0117-LCDR1

<400> SEQUENCE: 76

Gln Ala Ser His Asn Ile Tyr Ser Val Leu Ala
1               5                   10

<210> SEQ ID NO 77
<211> LENGTH: 11
<212> TYPE: PRT
<213> ORGANISM: Artificial Sequence -continued

```
<220> FEATURE:
<223> OTHER INFORMATION: SKA0127-LCDR1

<400> SEQUENCE: 77

Arg Ala Ser Glu Asp Ile Glu Ser Tyr Leu Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: SKA0141-LCDR1

<400> SEQUENCE: 78

Gln Ala Ser His Asn Ile Tyr Ser Asn Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: SKA0171-LCDR1

<400> SEQUENCE: 79

Gln Ala Ser Glu Thr Ile Tyr Ser Gly Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: SKA0001-LCDR2

<400> SEQUENCE: 80

Asp Ala Ser Asp Leu Ala Ser
1               5

<210> SEQ ID NO 81
<211> LENGTH: 7
<212> TYPE: PRT
<213> ORGANISM: Artificial Sequence
<220> FEATURE:
<223> OTHER INFORMATION: SKA0009-LCDR2

<400> SEQUENCE: 81

Asp Ala Ser Glu Leu Ala Ser
1               5

<210> SEQ ID NO 82
<211> LENGTH: 7
<212> TYPE: PRT
<213> ORGANISM: Artificial Sequence
<220> FEATURE:
<223> OTHER INFORMATION: SKA0016-LCDR2

<400> SEQUENCE: 82

Gln Ala Ser Lys Leu Glu Ser
1               5

<210> SEQ ID NO 83
<211> LENGTH: 7
<212> TYPE: PRT
<213> ORGANISM: Artificial Sequence
<220> FEATURE:
```

<223> OTHER INFORMATION: SKA0027-LCDR2

<400> SEQUENCE: 83

Thr Ala Ser Ser Leu Ala Ser
1               5

<210> SEQ ID NO 84
<211> LENGTH: 7
<212> TYPE: PRT
<213> ORGANISM: Artificial Sequence
<220> FEATURE:
<223> OTHER INFORMATION: SKA0028-LCDR2

<400> SEQUENCE: 84

Gly Ala Ser Asn Leu Glu Ser
1               5

<210> SEQ ID NO 85
<211> LENGTH: 7
<212> TYPE: PRT
<213> ORGANISM: Artificial Sequence
<220> FEATURE:
<223> OTHER INFORMATION: SKA0046-LCDR2

<400> SEQUENCE: 85

Gly Ala Ser Asn Leu Glu Ser
1               5

<210> SEQ ID NO 86
<211> LENGTH: 7
<212> TYPE: PRT
<213> ORGANISM: Artificial Sequence
<220> FEATURE:
<223> OTHER INFORMATION: SKA0052-LCDR2

<400> SEQUENCE: 86

Gly Ala Ser Asn Leu Glu Pro
1               5

<210> SEQ ID NO 87
<211> LENGTH: 7
<212> TYPE: PRT
<213> ORGANISM: Artificial Sequence
<220> FEATURE:
<223> OTHER INFORMATION: SKA0054-LCDR2

<400> SEQUENCE: 87

Leu Ala Ser Thr Leu Ala Ser
1               5

<210> SEQ ID NO 88
<211> LENGTH: 7
<212> TYPE: PRT
<213> ORGANISM: Artificial Sequence
<220> FEATURE:
<223> OTHER INFORMATION: SKA0117-LCDR2

<400> SEQUENCE: 88

Gly Ala Ser Asn Leu Glu Ser
1               5

<210> SEQ ID NO 89
<211> LENGTH: 7
<212> TYPE: PRT
<213> ORGANISM: Artificial Sequence
<220> FEATURE:
<223> OTHER INFORMATION: SKA0127-LCDR2

<400> SEQUENCE: 89

Ala Thr Ser Asn Leu Glu Thr
1               5

<210> SEQ ID NO 90
<211> LENGTH: 7
<212> TYPE: PRT
<213> ORGANISM: Artificial Sequence
<220> FEATURE:
<223> OTHER INFORMATION: SKA0141-LCDR2

<400> SEQUENCE: 90

Gly Ala Ser Asn Leu Glu Ser
1               5

<210> SEQ ID NO 91
<211> LENGTH: 7
<212> TYPE: PRT
<213> ORGANISM: Artificial Sequence
<220> FEATURE:
<223> OTHER INFORMATION: SKA0171-LCDR2

<400> SEQUENCE: 91

Asp Thr Ala Asn Leu Glu Thr
1               5

<210> SEQ ID NO 92
<211> LENGTH: 14
<212> TYPE: PRT
<213> ORGANISM: Artificial Sequence
<220> FEATURE:
<223> OTHER INFORMATION: SKA0001-LCDR3

<400> SEQUENCE: 92

Gln Ser Tyr Tyr Trp Gly Ser Ser Gly Asp Ile Gly Tyr Pro
1               5                   10

<210> SEQ ID NO 93
<211> LENGTH: 12
<212> TYPE: PRT
<213> ORGANISM: Artificial Sequence
<220> FEATURE:
<223> OTHER INFORMATION: SKA0009-LCDR3

<400> SEQUENCE: 93

Gln His Ala Asp Tyr Ala Ala Ser Ser Glu Asn Thr
1               5                   10

<210> SEQ ID NO 94
<211> LENGTH: 15
<212> TYPE: PRT
<213> ORGANISM: Artificial Sequence
<220> FEATURE:
<223> OTHER INFORMATION: SKA0016-LCDR3

<400> SEQUENCE: 94

Gln Ser Ile Ser Tyr Ile Ser Ser Gly Asp Thr Phe Phe Trp Ala
1               5                   10                  15

<210> SEQ ID NO 95
<211> LENGTH: 12
<212> TYPE: PRT
<213> ORGANISM: Artificial Sequence
<220> FEATURE:
<223> OTHER INFORMATION: SKA0027-LCDR3

```
<400> SEQUENCE: 95

Gln Cys Thr Tyr Ile Asn Asn Gly Tyr Gly Asn Thr
1               5                   10

<210> SEQ ID NO 96
<211> LENGTH: 12
<212> TYPE: PRT
<213> ORGANISM: Artificial Sequence
<220> FEATURE:
<223> OTHER INFORMATION: SKA0028-LCDR3

<400> SEQUENCE: 96

Gln Ser Ala Tyr Trp Gly Asn Asn Asn Asp Gly Ala
1               5                   10

<210> SEQ ID NO 97
<211> LENGTH: 15
<212> TYPE: PRT
<213> ORGANISM: Artificial Sequence
<220> FEATURE:
<223> OTHER INFORMATION: SKA0046-LCDR3

<400> SEQUENCE: 97

Gln Ser Ile Tyr Tyr Ser Ser Ser Ala Asp Thr Phe Phe Phe Pro
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: SKA0052-LCDR3

<400> SEQUENCE: 98

Gln Ser Val Gly Tyr Ser Gly Ser Val Asp Thr Phe Phe Tyr Ala
1               5                   10                  15

<210> SEQ ID NO 99
<211> LENGTH: 15
<212> TYPE: PRT
<213> ORGANISM: Artificial Sequence
<220> FEATURE:
<223> OTHER INFORMATION: SKA0054-LCDR3

<400> SEQUENCE: 99

Gln Ser Val Tyr Tyr Asp Ser Arg Gly Asp Thr Phe Phe Trp Ala
1               5                   10                  15

<210> SEQ ID NO 100
<211> LENGTH: 13
<212> TYPE: PRT
<213> ORGANISM: Artificial Sequence
<220> FEATURE:
<223> OTHER INFORMATION: SKA0117-LCDR3

<400> SEQUENCE: 100

Gln Ser Ala Tyr Tyr Ser Ser Ser Thr Gly Asp Asn Ala
1               5                   10

<210> SEQ ID NO 101
<211> LENGTH: 13
<212> TYPE: PRT
<213> ORGANISM: Artificial Sequence
<220> FEATURE:
<223> OTHER INFORMATION: SKA0127-LCDR3

<400> SEQUENCE: 101
```

-continued

```
Gln Gly Tyr Tyr Glu Leu Ser Ser Ile Asp Asn Asn Ala
1               5                   10

<210> SEQ ID NO 102
<211> LENGTH: 13
<212> TYPE: PRT
<213> ORGANISM: Artificial Sequence
<220> FEATURE:
<223> OTHER INFORMATION: SKA0141-LCDR3

<400> SEQUENCE: 102

Gln Ser Ala Tyr Tyr Ser Ser Asn Ala Gly Tyr Asn Ala
1               5                   10

<210> SEQ ID NO 103
<211> LENGTH: 13
<212> TYPE: PRT
<213> ORGANISM: Artificial Sequence
<220> FEATURE:
<223> OTHER INFORMATION: SKA0171-LCDR3

<400> SEQUENCE: 103

Leu Tyr Ala Tyr Tyr Ser Gly Gly Ser Ala Asp Asn Ala
1               5                   10

<210> SEQ ID NO 104
<211> LENGTH: 5
<212> TYPE: PRT
<213> ORGANISM: Artificial Sequence
<220> FEATURE:
<223> OTHER INFORMATION: g-silent

<400> SEQUENCE: 104

Arg Arg Gly Pro Lys
1               5

<210> SEQ ID NO 105
<211> LENGTH: 13
<212> TYPE: PRT
<213> ORGANISM: Artificial Sequence
<220> FEATURE:
<223> OTHER INFORMATION: ACT-5

<400> SEQUENCE: 105

Leu His Glu Ala Leu His Ala His Tyr Thr Arg Lys Glu
1               5                   10

<210> SEQ ID NO 106
<211> LENGTH: 330
<212> TYPE: PRT
<213> ORGANISM: Homo sapiens

<400> SEQUENCE: 106

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
           100                 105                 110

Pro Ala Pro Glu Leu Leu Gly Gly Pro Ser Val Phe Leu Phe Pro Pro
           115                 120                 125

Lys Pro Lys Asp Thr Leu Met Ile Ser Arg Thr Pro Glu Val Thr Cys
       130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
               165                 170                 175

Glu Gln Tyr Asn Ser Thr Tyr Arg Val Val Ser Val Leu Thr Val Leu
           180                 185                 190

His Gln Asp Trp Leu Asn Gly Lys Glu Tyr Lys Cys Lys Val Ser Asn
           195                 200                 205

Lys Ala Leu Pro Ala Pro Ile Glu Lys Thr Ile Ser Lys Ala Lys Gly
       210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
               245                 250                 255

Pro Ser Asp Ile Ala Val Glu Trp Glu Ser Asn Gly Gln Pro Glu Asn
           260                 265                 270

Asn Tyr Lys Thr Thr Pro Pro Val Leu Asp Ser Asp Gly Ser Phe Phe
           275                 280                 285

Leu Tyr Ser Lys Leu Thr Val Asp Lys Ser Arg Trp Gln Gln Gly Asn
       290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
               325                 330
```

```
<210> SEQ ID NO 107
<211> LENGTH: 326
<212> TYPE: PRT
<213> ORGANISM: Homo sapiens

<400> SEQUENCE: 107
```

```
Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
           20                  25                  30

Phe Pro Glu Pro Val Thr Val Ser Trp Asn Ser Gly Ala Leu Thr Ser
           35                  40                  45

Gly Val His Thr Phe Pro Ala Val Leu Gln Ser Ser Gly Leu Tyr Ser
       50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
           100                 105                 110

Pro Val Ala Gly Pro Ser Val Phe Leu Phe Pro Pro Lys Pro Lys Asp
           115                 120                 125
```

```
Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 108
<211> LENGTH: 377
<212> TYPE: PRT
<213> ORGANISM: Homo sapiens

<400> SEQUENCE: 108

Ala Ser Thr Lys Gly Pro Ser Val Phe Pro Leu Ala Pro Cys Ser Arg
1                   5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
```

-continued

```
                165                   170                   175
Pro Lys Asp Thr Leu Met Ile Ser Arg Thr Pro Glu Val Thr Cys Val
            180                   185                   190

Val Val Asp Val Ser His Glu Asp Pro Glu Val Gln Phe Lys Trp Tyr
            195                   200                   205

Val Asp Gly Val Glu Val His Asn Ala Lys Thr Lys Pro Arg Glu Glu
210                   215                   220

Gln Tyr Asn Ser Thr Phe Arg Val Val Ser Val Leu Thr Val Leu His
225                   230                   235                   240

Gln Asp Trp Leu Asn Gly Lys Glu Tyr Lys Cys Lys Val Ser Asn Lys
            245                   250                   255

Ala Leu Pro Ala Pro Ile Glu Lys Thr Ile Ser Lys Thr Lys Gly Gln
            260                   265                   270

Pro Arg Glu Pro Gln Val Tyr Thr Leu Pro Pro Ser Arg Glu Glu Met
            275                   280                   285

Thr Lys Asn Gln Val Ser Leu Thr Cys Leu Val Lys Gly Phe Tyr Pro
            290                   295                   300

Ser Asp Ile Ala Val Glu Trp Glu Ser Ser Gly Gln Pro Glu Asn Asn
305                   310                   315                   320

Tyr Asn Thr Thr Pro Pro Met Leu Asp Ser Asp Gly Ser Phe Phe Leu
            325                   330                   335

Tyr Ser Lys Leu Thr Val Asp Lys Ser Arg Trp Gln Gln Gly Asn Ile
            340                   345                   350

Phe Ser Cys Ser Val Met His Glu Ala Leu His Asn Arg Phe Thr Gln
            355                   360                   365

Lys Ser Leu Ser Leu Ser Pro Gly Lys
            370                   375

<210> SEQ ID NO 109
<211> LENGTH: 327
<212> TYPE: PRT
<213> ORGANISM: Homo sapiens

<400> SEQUENCE: 109

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160
```

```
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 110
<211> LENGTH: 328
<212> TYPE: PRT
<213> ORGANISM: Artificial Sequence
<220> FEATURE:
<223> OTHER INFORMATION: Anti-IL-8 Antibody_H_C

<400> SEQUENCE: 110

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Arg Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Leu His Glu Ala Leu His Ala His Thr Thr
305                 310                 315                 320

Arg Lys Glu Leu Ser Leu Ser Pro
                325

<210> SEQ ID NO 111
<211> LENGTH: 99
<212> TYPE: PRT
<213> ORGANISM: Homo sapiens

<400> SEQUENCE: 111

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 112
<211> LENGTH: 116
<212> TYPE: PRT
<213> ORGANISM: Artificial Sequence
<220> FEATURE:
<223> OTHER INFORMATION: Mouse anti-IL-8 mAb_VH

<400> SEQUENCE: 112

Gln Val Gln Leu Gln Gln Pro Gly Val Glu Leu Val Met Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
        35                  40                  45

Gly Glu Ile Asp Pro Ser Asp Ser Asn Thr Asn Tyr Asn Gln Lys Phe
        50                  55                  60

Lys Gly Lys Ala Thr Leu Thr Leu Asp Lys Ser Ser Ser Thr Ala Tyr
65                  70                  75                  80

-continued

```
Met Gln Leu Thr Ser Leu Thr Ser Glu Asp Ser Ala Val Tyr Tyr Cys
                85              90              95

Ala Arg Glu Leu Leu His Ala Val Tyr Trp Gly Gln Gly Thr Leu Val
            100             105             110

Thr Val Ser Ser
        115

<210> SEQ ID NO 113
<211> LENGTH: 106
<212> TYPE: PRT
<213> ORGANISM: Artificial Sequence
<220> FEATURE:
<223> OTHER INFORMATION: Mouse anti-IL-8 mAb_VL

<400> SEQUENCE: 113

Asp Ile Gln Met Thr Gln Ser Pro Ser Ser Leu Ser Ala Ser Leu Gly
1               5               10              15

Gly Lys Val Thr Ile Thr Cys Thr Ala Ser Gln Asp Ile His Lys Tyr
            20              25              30

Ile Ser Trp Phe Gln His Lys Pro Gly Lys Gly Pro Arg Leu Leu Ile
        35              40              45

His Tyr Thr Ser Thr Leu Gln Pro Gly Ile Pro Ser Arg Phe Ser Gly
    50              55              60

Ser Gly Ser Gly Arg Asp Tyr Ser Phe Ser Ile Ser Asn Leu Glu Pro
65              70              75              80

Glu Asp Val Ala Thr Tyr Tyr Cys Leu Gln Tyr Asp Asn Leu Trp Thr
            85              90              95

Phe Gly Gly Gly Thr Lys Leu Asp Ile Lys
            100             105

<210> SEQ ID NO 114
<211> LENGTH: 330
<212> TYPE: PRT
<213> ORGANISM: Artificial Sequence
<220> FEATURE:
<223> OTHER INFORMATION: Mouse anti-IL-8 mAb_CH

<400> SEQUENCE: 114

Ala Lys Thr Thr Ala Pro Ser Val Tyr Pro Leu Ala Pro Val Cys Gly
1               5               10              15

Asp Thr Thr Gly Ser Ser Val Thr Leu Gly Cys Leu Val Lys Gly Tyr
            20              25              30

Phe Pro Glu Pro Val Thr Leu Thr Trp Asn Ser Gly Ser Leu Ser Ser
        35              40              45

Gly Val His Thr Phe Pro Ala Val Leu Gln Ser Asp Leu Tyr Thr Leu
    50              55              60

Ser Ser Ser Val Thr Val Thr Ser Ser Thr Trp Pro Ser Gln Ser Ile
65              70              75              80

Thr Cys Asn Val Ala His Pro Ala Ser Ser Thr Lys Val Asp Lys Lys
            85              90              95

Ile Glu Pro Arg Gly Pro Thr Ile Lys Pro Cys Pro Pro Cys Lys Cys
            100             105             110

Pro Ala Pro Asn Leu Leu Gly Gly Pro Ser Val Phe Ile Phe Pro Pro
        115             120             125

Lys Ile Lys Asp Val Leu Met Ile Ser Leu Ser Pro Ile Val Thr Cys
    130             135             140

Val Val Val Asp Val Ser Glu Asp Asp Pro Asp Val Gln Ile Ser Trp
```

-continued

```
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
                180                 185                 190

His Gln Asp Trp Met Ser Gly Lys Glu Phe Lys Cys Lys Val Asn Asn
                195                 200                 205

Lys Asp Leu Pro Ala Pro Ile Glu Arg Thr Ile Ser Lys Pro Lys Gly
    210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
                260                 265                 270

Asn Tyr Lys Asn Thr Glu Pro Val Leu Asp Ser Asp Gly Ser Tyr Phe
                275                 280                 285

Met Tyr Ser Lys Leu Arg Val Glu Lys Lys Asn Trp Val Glu Arg Asn
    290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330

<210> SEQ ID NO 115
<211> LENGTH: 107
<212> TYPE: PRT
<213> ORGANISM: Artificial Sequence
<220> FEATURE:
<223> OTHER INFORMATION: Mouse anti-IL-8 mAb_CL

<400> SEQUENCE: 115

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
                20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
                100                 105

<210> SEQ ID NO 116
<211> LENGTH: 328
<212> TYPE: PRT
<213> ORGANISM: Artificial Sequence
<220> FEATURE:
<223> OTHER INFORMATION: SG1106

<400> SEQUENCE: 116

Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Ala Ala Leu Pro Ala Pro Ile Ser Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Leu His Glu Ala Leu His Ala His Tyr Thr
305                 310                 315                 320

Arg Lys Glu Leu Ser Leu Ser Pro
                325
```

```
<210> SEQ ID NO 117
<211> LENGTH: 5
<212> TYPE: PRT
<213> ORGANISM: Artificial Sequence
<220> FEATURE:
<223> OTHER INFORMATION: g-silent_IL-8

<400> SEQUENCE: 117

Arg Arg Gly Pro Ser
1               5

<210> SEQ ID NO 118
<211> LENGTH: 13
<212> TYPE: PRT
<213> ORGANISM: Artificial Sequence
<220> FEATURE:
```

<223> OTHER INFORMATION: ACT-5_IL-8

<400> SEQUENCE: 118

Leu His Glu Ala Leu His Ala His Thr Thr Arg Lys Glu
1               5                   10

<210> SEQ ID NO 119
<211> LENGTH: 330
<212> TYPE: PRT
<213> ORGANISM: Artificial Sequence
<220> FEATURE:
<223> OTHER INFORMATION: IGHG1*01(J00228)

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

```
<210> SEQ ID NO 120
<211> LENGTH: 327
<212> TYPE: PRT
<213> ORGANISM: Artificial Sequence
<220> FEATURE:
<223> OTHER INFORMATION: IGHG4*01(K01316)

<400> SEQUENCE: 120

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```